(12) United States Patent
Yu et al.

(10) Patent No.: US 10,604,529 B2
(45) Date of Patent: Mar. 31, 2020

(54) FUSED IMIDAZOLE COMPOUND HAVING INDOLEAMINE 2,3-DIOXYGENASE INHIBITORY ACTIVITY

(71) Applicant: SHENZHEN CHIPSCREEN BIOSCIENCES CO., LTD., Shenzhen, Guangdong (CN)

(72) Inventors: Jindi Yu, Guangdong (CN); Xianping Lu, Guangdong (CN); Zhibin Li, Guangdong (CN); Lijun Xin, Guangdong (CN); Jiangfei Zhu, Guangdong (CN); Chao Fu, Guangdong (CN)

(73) Assignee: SHENZHEN CHIPSCREEN BIOSCIENCES CO., LTD., Shenzhen, Guangdong (CN)

( * ) Notice: Subject to any disclaimer, the term of this patent is extended or adjusted under 35 U.S.C. 154(b) by 0 days.

(21) Appl. No.: 16/472,185

(22) PCT Filed: Dec. 18, 2017

(86) PCT No.: PCT/CN2017/116914
§ 371 (c)(1),
(2) Date: Jun. 20, 2019

(87) PCT Pub. No.: WO2018/113624
PCT Pub. Date: Jun. 28, 2018

(65) Prior Publication Data
US 2019/0352307 A1    Nov. 21, 2019

(30) Foreign Application Priority Data

Dec. 20, 2016  (CN) .......................... 2016 1 1186194

(51) Int. Cl.
*C07D 487/04* (2006.01)
*C07D 519/00* (2006.01)
*C07D 307/91* (2006.01)

(52) U.S. Cl.
CPC ......... *C07D 487/04* (2013.01); *C07D 307/91* (2013.01); *C07D 519/00* (2013.01)

(58) Field of Classification Search
CPC ... C07D 487/04; C07D 307/91; C07D 519/00
See application file for complete search history.

(56) References Cited

U.S. PATENT DOCUMENTS

| | | | |
|---|---|---|---|
| 10,233,190 B2 | 3/2019 | Mautino et al. | |
| 10,308,647 B2 * | 6/2019 | Askew | C07D 471/04 |
| 2016/0060266 A1 | 3/2016 | Kumar et al. | |

FOREIGN PATENT DOCUMENTS

| | | |
|---|---|---|
| CN | 1795187 A | 6/2006 |
| CN | 101932325 A | 12/2010 |
| CN | 103054870 A | 4/2013 |
| CN | 103547579 A | 1/2014 |
| CN | 101932325 B | 5/2014 |
| CN | 102579452 B | 5/2014 |
| CN | 105189466 A | 12/2015 |
| WO | 2016037026 A1 | 3/2016 |

OTHER PUBLICATIONS

International Search Report for PCT/CN2017/116914 dated Feb. 26, 2018, ISA/CN.
Leklem J. E., Quantitative aspects of tryptophan metabolism in humans and other species: a review, Am J Clin Nutr, 1971, 24 (6): 659-672.
Yamaoto S. et al., Tryptophan Pyrrolase of Rabbit Intestine D-and L-Tryptophan-Cleaving Enzyme or Enzymes, J Biol Chem, 1967, 242(22): 5260-5266.
MacKenzie, C. R. et al., Role of indoleamine 2,3-Dioxygenase in antimicrobial defence and immuno-regulation: tryptophan depletion versus production of toxic kynurenines, Current Drug Metabolism, 2007, 8: 237-244.
Fusao Hirta et al., Indoleamine 2,3-Dioxygenase Characterization and Properties of Enzyme O2-Complex, J Biol Chem, 1997 252(13): 4637-4642.
King N. J. et al., Molecules in focus: Indoleamine 2,3-diocygenase, The Int J Biochem Cell Biol, 2007 39(12): 2167-2172.
Munn D. H. et al., Inhibition of T Cell Proliferation by Macrophage Tryptophan Catabolism, J Exp Med, 1999,189(9): 1363-1372.
Munn D. H. et al.,Prevention of Allogeneic Fetal Rejection by Tryptophan Catabolism, Science, 1998, 281(5380): 1191-1193.
Friberg M. et al., Indoleamine 2,3-Dioxygenase Contributes to Tumor Cell Evasion of T Cell-Mediated Rejection, Int J Cancer, 2002,101(2): 151-155.
Terness P. et al., Regulation of human auto- and alloreactive T cells by indoleamine 2,3-dioxygenase (IDO)-producing dendritic cells: too much ado about IDO?, Blood, 2005,105(6): 2480-2486.
Roy E. J. et al., Neuronal localication of indoleamine 2,3-dioxygenase in mice, Neurosci Lett, 2005, 387(2): 95-99.

(Continued)

*Primary Examiner* — Timothy R Rozof
(74) *Attorney, Agent, or Firm* — Yue (Robert) Xu; Apex Attorneys at Law, LLP

(57) ABSTRACT

The invention discloses a type of fused imidazole compound, preparation method and application thereof. The structure of the compound is shown in general formula I. The definition of each group therein is as described in the specification. These compounds are capable of selectively inhibiting indoleamine 2,3-dioxygenase (IDO). The compounds can act as an IDO inhibitor for treating and/or preventing a disease having a pathological feature with IDO-mediated tryptophan metabolic pathways, for example, cancer, eye disease, autoimmune disease, psychological disorder, depression symptom, anxiety disorder and other diseases.

19 Claims, No Drawings

(56) References Cited

OTHER PUBLICATIONS

Takikawa et al., Regulation of Indoleamine 2,3-Dioxygenase, The First Enzyme in UV Filter Biosynthesis in the Human Lens, Adv. Exp. Med. Biol. 1999, 467, 241-245.

Takikawa O. et al. Indoleamine 2,3-dioxygenase in the Human Lens, the First Enzyme in the Synthesis of UV Filters, Exp. Eye Res. 2001, 72, 271-277.

* cited by examiner

FUSED IMIDAZOLE COMPOUND HAVING INDOLEAMINE 2,3-DIOXYGENASE INHIBITORY ACTIVITY

This application is the national phase of International Application No. PCT/CN2017/116914, titled "FUSED IMIDAZOLE COMPOUND HAVING INDOLEAMINE 2,3-DIOXYGENASE INHIBITORY ACTIVITY", filed on Dec. 18, 2017, which claims the priority of Chinese Patent Application No. 201611186194.4, filed on Dec. 20, 2016, filed with China National Intellectual Property Administration, and titled with "FUSED IMIDAZOLE COMPOUND HAVING INDOLEAMINE 2,3-DIOXYGENASE INHIBITORY ACTIVITY", and the disclosure of which is hereby incorporated by reference.

FIELD

The present invention relates to a fused imidazole compound having indoleamine 2,3-dioxygenase (IDO) inhibitory activity; a preparation method thereof, and an clinical application thereof in treating diseases associated with abnormal activity of indoleamine-2,3-dioxygenase.

BACKGROUND

Tryptophan (Trp) is an essential amino acid in the human body. Part of the tryptophan obtained from the diet is used to synthesize protein, niacin and the neurotransmitter serotonin, and the rest is mainly metabolized by the kynurenine pathway (Leklem J. E., Am J Clin Nutr, 1971, 24 (6): 659-672), Indoleamine 2,3-dioxygenase (IDO) is a key enzyme involved in this metabolic pathway.

Indoleamine 2,3-dioxygenase is an intracellular heme-containing enzyme that was first discovered in the intestine of rabbits in 1967 (Yamaoto S. et al., J Biol Chem, 1967, 242(22): 5260-5266), and is the only rate-limiting enzyme outside the liver that can catalyze the oxidative pyrolysis of indole ring in tryptophan molecules and catabolize along the kynurenine pathway (MacKenzie, C. R. et al. Current Drug Metabolism, 2007, 8: 237-244).

IDO is widely distributed in extrahepatic tissues, especially in fibroblasts, epithelial cells, macrophages, dendritic cells (DCs), and microglia on the surface of mucosal tissue (such as placenta, lung and small intestine), and in thymus medulla and secondary lymphoid organ T cell region, gastrointestinal tract mucosa, epididymis, placenta, anterior chamber, etc., but is less expressed in the spleen, lymph nodes, and thymus cortex (Fusao Hirata et al., J Biol Chem, 1977 252(13): 4637-4642).

TDO is primarily expressed in the liver and controls the flow of tryptophan uptake from food into the serotonin and kynurenine pathway.

INF-specific inflammatory factors, such as IFN-γ, stimulate and induce the expression of IDO at the level of transcription. Other inflammatory factors, such as IFN-α, IFN-β and LPS, may also induce IDO expression, but the inductive effect is not as good as IFN-γ (King N. J. et al., The Int J Biochem Cell Biol, 2007 39(12): 2167-2172). At the same time, the expression of IDO is also regulated by immunologically active molecules such as prostaglandins, cell surface protein cytotoxic T lymphoce-associated antigen (CTLA24), CD40, and Toll-like receptors.

Recent studies have shown that IDO is involved in the regulation of T cell regulation. IDO can cleave T cell activation by degrading tryptophan since T cells are particularly sensitive to tryptophan depletion, and when tryptophan concentration is low, T cell proliferation will be stationary in G1 phase (Munn D. H. et al., J Exp Med, 1999, 189(9): 1363-1372). Based on this mechanism, IDO expressed in the placenta protects the fetus front maternal rejection (Munn D. H. et al., Science, 1998, 281(5380): 1191-1193); however, IDO expressed in tumors mediates immune escape of tumors (Friberg M. et al., Int J Cancer, 2002, 101(2): 151-155). IDOs on antigen-presenting cells such as macrophages and dendritic cells (DCs) can induce T cell immune tolerance to tumor antigens by inhibiting T cell proliferation (Terness P. et al., Blood, 2005, 105(6): 2480-2486).

IDO is closely related to nervous system diseases, and can affect the function of the brain through at least two mechanisms: 1) reducing the circulating tryptophan concentration by metabolizing tryptophan in the inflammatory reaction, thereby lowering the level of serotonin, and leading to depression 2) catalyzing the metabolism of tryptophan kynurenine pathway to accumulate kynurenine and neurotoxic quinolinic acid (Roy E. J. et al., Neurosci Lett, 2005, 387(2): 95-99).

IDO also involves the development of age-related nuclear cataract. IDO is the first enzyme in the biosynthesis of ultraviolet filters in the crystalline lens and is a rate-limiting enzyme. Ultraviolet filter compounds (kynurine and 3-hydroxykynurenine glucoside) from tryptophan degradation modify proteins presented in the human crystalline lens. The amount of these ultraviolet filter compounds increases with age (Takikawa et al. Adv. Exp. Med. Biol. 1999, 467, 241-245). It has also been reported that these ultraviolet filter compounds cause the crystalline lens to become opaque gradually, and thereby leads to the so-called age-related. nuclear cataract. IDO inhibitors block this natural process (Takikawa O. et al. Exp. Eye Res. 2001, 72, 271-277).

It is known in the conventional art that IDO inhibitors can be used to treat or prevent diseases having a pathological feature of IDO-mediated tryptophan metabolism pathways, including viral infections such as AIDS, Lyme disease and bacterial infections such as streptococcal infections, neurodegenerative disorders (e.g. Alzheimer's disease, Huntington's disease and Parkinson's disease), depression, cancer (including T-cell leukemia and colon cancer), eye diseases (e.g. cataracts and age-related yellowing) and autoimmune diseases (CN1795187A, CN101932325A, CN103054870A).

There are currently three IDO inhibitors in different clinical phases, including: 1) Epacadostat of Incyte, which is in Phase II clinical trials for the treatment of myelodysplastic syndromes, melanoma and female reproductive system cancer; 2) Indoximod of Newlink, which is in Phase II clinical trials for the treatment of breast cancer, prostate cancer, malignant brain tumors, pancreatic cancer and melanoma; 3) GDC-0919 of Roche, which is in Phase I clinical trials for the treatment of advanced solid tumors.

IDO is closely related to a variety of disease pathogenesis, and has been confirmed to be a target for major diseases such as cancer, Alzheimer's disease, depression, cataract (CN101932325B, CN102579452B). Therefore, IDO inhibitors have broad application prospects as drugs. However, no suitable IDO inhibitors have been marketed so far. IDO inhibitors currently in clinical research have the disadvantages of relatively high dose and relatively severe side effects. Therefore, it is of great theoretical significance and application value to find IDO inhibitors with higher IDO inhibitory activity and lower toxicity.

SUMMARY

In order to overcome the deficiencies in the conventional art, the inventors conducted extensive research, and unexpectedly found through a large number of screening tests that compounds having the following General Formula I have unexpectedly good IDO inhibitory effect:

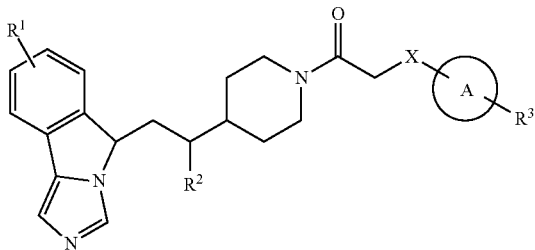

The compound of General Formula I of the present disclosure can selectively inhibit indoleamine 2,3-dioxygenase, and can be used to treat and/or prevent diseases having a pathological feature with IDO-mediated tryptophan metabolism pathways. Such diseases include, but are not limited to, cancer, eye diseases, autoimmune diseases, psychological disorders, depression, and anxiety.

In one aspect, the present disclosure provides a fused imidazole compound having indoleamine 2,3-dioxygenase inhibitory activity.

In another aspect, the present disclosure provides a method of preparing the compound of the present disclosure.

The compound of the present disclosure includes any suitable form thereof, including pharmaceutically acceptable salts, solvates, enantiomers and racemic mixtures thereof.

The present disclosure is further directed to a pharmaceutical composition comprising the compound of the present disclosure (including every suitable form thereof) as an active ingredient.

In another aspect, the present disclosure also provides use of the compound of the present disclosure in the preparation of a medicament for use as a indoleamine 2,3-dioxygenase (IDO) inhibitor. In one other aspect, the present disclosure also provides use of the compound of the present disclosure in the preparation of a medicament for the treatment or prevention of a disease or condition such as cancer, eye disease, autoimmune disease, psychological disorder, depression and anxiety.

The compound of the present disclosure has the chemical structure as shown in General Formula I:

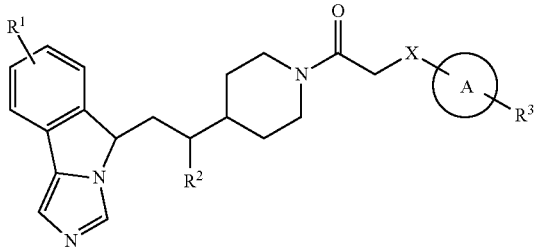

wherein,
$R^1$ is one or more substituents selected from the group consisting of hydrogen, hydroxyl, cyano, nitro, halogen, $C_{1-6}$ alkyl, $C_{1-6}$ alkoxy, $C_{1-6}$ haloalkyl, alkylcarbonyl and $C_{1-6}$ alkylamino;

$R^2$ is hydroxyl or amino;
$R^3$ is one or more substituents selected from the group consisting of hydrogen, hydroxyl, cyano, halogen, $C_{1-6}$ alkyl, $C_{1-6}$ alkoxy, $C_{1-6}$ haloalkyl, $C_{1-6}$ alkylcarbonyl and $C_{1-6}$ alkylamino;
X is $NR^4$ or O;
wherein $R^4$ is hydrogen or $C_{1-6}$ alkyl;
ring A is an optionally substituted group selected from the group consisting of: phenyl; 3- to 7-membered saturated or partially unsaturated carbocyclic ring; 8 to 10 membered saturated, partially unsaturated or aromatic bicyclic or tricyclic ring; 5- to 6-membered monocyclic heteroaryl ring having 1 to 4 heteroatoms independently selected from nitrogen, oxygen or sulfur; 4- to 7-membered saturated or partially unsaturated heterocyclic ring having 1 to 3 heteroatoms independently selected from nitrogen, oxygen or sulfur; 7- to 10-membered saturated or partially unsaturated heterocyclic bicyclic or tricyclic ring having 1 to 5 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

For the compound of the above-mentioned General Formula I, preferably,
$R^1$ is one or more substituents selected from the group consisting of hydrogen, hydroxyl, cyano, nitro, halogen, and $C_{1-6}$ haloalkyl;
$R^2$ is hydroxyl;
$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;
X is $NR^4$;
wherein $R^1$ is hydrogen, methyl or ethyl;
ring A is a group selected from the group consisting of phenyl; 3- to 6-membered saturated carbocyclic ring; 8- to 10-membered aromatic bicyclic or tricyclic ring; 5- to 6-membered monocyclic heteroaryl ring having 1 to 4 heteroatoms independently selected from nitrogen, oxygen or sulfur; 7- to 10-membered saturated or partially unsaturated heterocyclic bicyclic or tricyclic ring having 1 to 5 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

For the compound of the above-mentioned General Formula I, more preferably,
$R^1$ is one or more substituents selected from the group consisting of hydrogen, hydroxyl, cyano, nitro and halogen;
$R^2$ is hydroxyl;
$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;
X is $NR^4$;
wherein $R^1$ is hydrogen or methyl;
ring A is a group selected from the group consisting of: phenyl; 3- to 6-membered saturated carbocyclic ring; 8- to 10-membered aromatic bicyclic or tricyclic ring; 5- to 6-membered monocyclic heteroaryl ring having 1 to 4 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

For the compound of the above-mentioned General Formula I, further preferably,
$R^1$ is one or more substituents selected from the group consisting of hydrogen, hydroxyl, cyano and nitro;

R² is hydroxyl;

R³ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 8- to 10-membered aromatic bicyclic or tricyclic ring; 5- to 6-membered monocyclic heteroaryl ring having 1 to 4 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

For the compound of the above-mentioned General Formula (I), further more preferably, $R^1$ is one or more substituents selected from hydrogen, hydroxyl or cyano;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 5- to 6-membered monocyclic heteroaryl ring having 1 to 4 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

For the compound of the above-mentioned General Formula (I), most preferably, $R^1$ is hydrogen;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 5- to 6-membered monocyciic heteroaryl ring having 1 to 4 heteroatoms independently selected from nitrogen, oxygen or sulfur; or 8- to 10-membered heteroaryl bicyclic or tricyclic ring having 1 to 5 heteroatoms independently selected from nitrogen, oxygen or sulfur.

The "halogen" of the present disclosure refers to fluorine, chlorine, bromine, iodine.

The "alkyl" of the present disclosure refers to a straight-chain and branched-chain or cyclic alkyl having from 1 to about 20 carbon atoms, usually from 1 to 12 carbon atoms, preferably from 1 to 8, from 1 to 6, even further preferably from 1 to 4 carbon atoms. Examples of the linear alkyl include those having I to 8 carbon atoms such as methyl, ethyl, n-propyl, n-butyl, n-pentyl, n-hexyl, n-heptyl and n-octyl; examples of the branched alkyl include, but are not limited to, isopropyl, isobutyl, sec-butyl, tert-butyl, neopentyl, isopentyl, isohexyl, and 2,2-dimethylpropyl; examples of the cycloalkyl include, but are not limited to, cyclopropyl, cyclobutyl, cyclopentyl, cyclohexyl, cycloheptyl, and cyclooctyl.

The "haloalkyl" of the present disclosure includes mono-haloalkyl and polyhaloalkyl (wherein all halogen atoms may be the same or different). Partially halogenated alkyl is included in the "haloalkyl" of the present disclosure. Examples of the haloalkyl include trifluoromethyl, 1,1-dichloroethyl, 1,2-dichloroethyl, 1,3-dibromo-3,3-difluoropropyl, etc.

The "alkoxy" of the present disclosure refers to a group formed by linking the above-mentioned alky to an oxygen atom, wherein the oxygen atom has a free bonding ability, such as methoxy, ethoxy, propoxy, butoxy, pentyloxy, iso-propoxy, tort-butoxy, cyclopropoxy, cyclohexyloxy, etc.

The "pharmaceutically acceptable salt" or "medicinal salt" of the present disclosure refers to acid and base addition salt and solvate. Such pharmaceutically acceptable salts include those thrilled with acids. The acid includes hydrochloric acid, phosphoric acid, hydrobromic acid, sulfuric acid, sulfinic acid, formic acid, p-toluenesulfonic acid, methanesulfonic acid, nitric acid, benzoic acid, citric acid, tartaric acid, maleic acid, hydroiodic acid, chain carboxylic acid such as acetic acid, $HOOC-(CH_2)_n-COOH$ (n=0-4), etc.; also include salts formed with bases, the cations of the salts include ions of sodium, potassium, calcium, ammonium, etc.

The "substituted" of the present disclosure refers to the organic group (which contains one or more bonds bonded to a hydrogen atom) as defined herein which is substituted by one or more bonds bonded to a non-hydrogen atom or group of atoms, the non-hydrogen atom or atomic group is a substituent.

The substituent of the compound of the present disclosure includes such as halogen, alkyl (preferably $C_{1-8}$ alkyl, $C_{1-6}$ alkyl or $C_{1-4}$ alkoxy (preferably $C_{1-8}$ alkoxy, $C_{1-6}$ alkoxy or $C_{1-4}$ alkoxy), haloalkyl (preferably $C_{1-8}$ haloalkyl, $C_{1-6}$ haloalkyl or $C_{1-4}$ haloalkyl), haloalkoxy group (preferably $C_{1-8}$ haloalkoxy, $C_{1-6}$ haloalkoxy or $C_{1-4}$ haloalkoxy), hydroxyl, hydroxyalkyl (preferably hydroxy $C_{1-8}$ alkyl, hydroxy $C_{1-6}$ alkyl or hydroxy $C_{1-4}$ alkyl).

In another aspect, the present disclosure also directed to fluorescent labeled, spin labeled, heavy-metal or isotope labeled derivatives, which can be used not only in imaging, but also for in vivo and in vitro detection, localizing and quantifying the IDO enzyme in the tissue samples (including humans), and the IDO enzyme ligand is recognized by binding inhibition of the labeled compound. Therefore, the present disclosure further provides an IDO enzyme detection reagent or kit containing such labeled compounds.

The present disclosure further provides an isotopically labeled compound of the compound of the present disclosure. The "isotopically labeled compound" of the compound of the present disclosure or the "isotopically labeled" compound of the present disclosure refers to the compound described herein, wherein one or more atoms are replaced by an isotope atom, and the atomic mass or mass number of the isotope atom is different from the atomic mass or mass number of those normally found in nature (i.e., naturally occurring). Suitable radionuclides may include, but are not limited to, 2H (also written as D), 3H (also written as T), 11C, 13C, 14C, 13N, 15N, 15O, 17O, 18O, 18F, 35S, 36Cl, 82Br, 75Br, 76Br, 77Br, 123I, 124I, 125I and 131I. The type of radioisotope contained in the isotopically labeled compound will depend on the specific application of the isotopically labeled compound. For example, for labeling and competition assays of IDO enzymes in vitro, compounds comprising 3H, 14C, 82Br, 125I, 131I, 35S are generally most useful. For isotope imaging applications, 11C, 18F, 125I, 123I, 124I, 131I, 75Br, 76Br or 77Br are generally most useful.

The methods of labeling organic compounds with radioisotopes known in the conventional art are also applicable to the compound of the present disclosure.

In another aspect, the present disclosure provides a method of preparing a compound of General Formula I of the present disclosure:

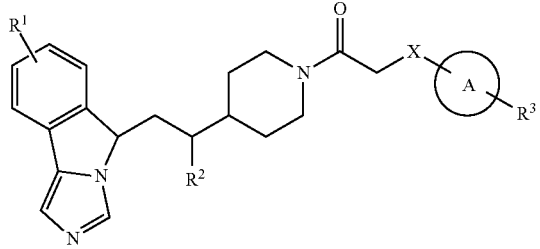

I the method comprises reacting a compound of Formula C

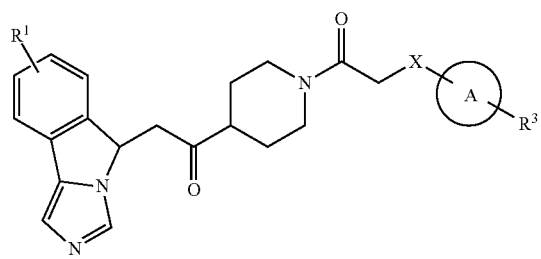

C under the action of an organic solvent and a reducing aunt to form a compound of General Formula I, wherein $R^1$, $R^2$, $R^3$, X and A are as defined above.

The present disclosure also provides a method of preparing a compound of Formula C:

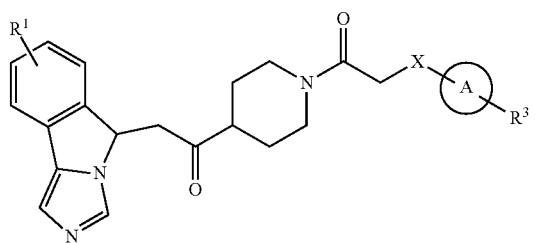

C including coupling a compound of Formula A

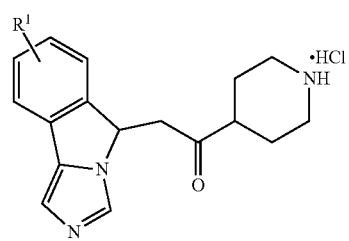

A with a compound of Formula B

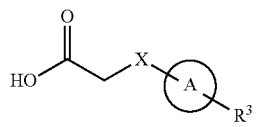

B under the action of an organic solvent and a coupling reagent to form a compound of Formula C, wherein $R^1$, $R^3$, X and A are as defined above.

In particular, the present disclosure also provides a use of a compound of Formula C as an intermediate for the preparation of a compound of General Formula I of the present disclosure.

Preparation of Compound of Formula A

In addition, the present disclosure further provides a method of preparing a compound of the above-mentioned Formula A, includes the following steps (a)-(d):

(a) under palladium catalysis. Compound 1 and Compound 2 are subjected to Suzuki cross-coupling to obtain Compound 3;

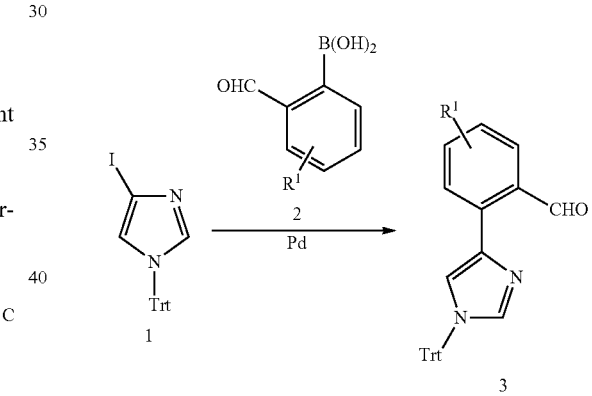

(b) under the action of a base, Compound 3 and Compound 4 are subjected to Claisen-Schimidt condensation to obtain Compound 5;

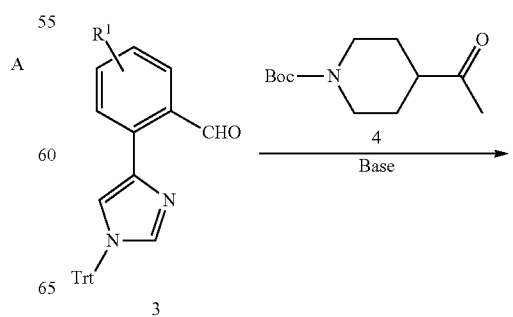

-continued

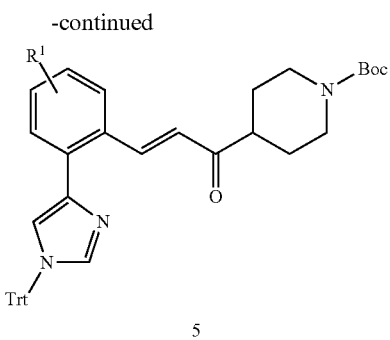

5

(c) Compound 5 loses tritylmethyl under acetic acid conditions and cyclizes to obtain Compound 6;

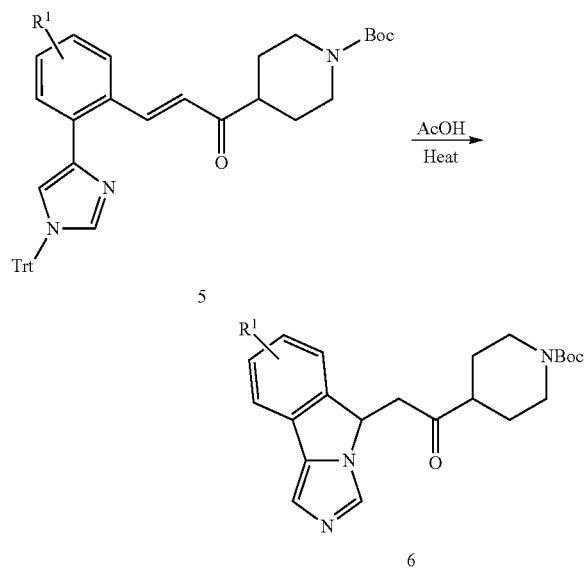

(d) Compound 6 is subjected to Boc Deprotection under acidic conditions to obtain intermediate A:

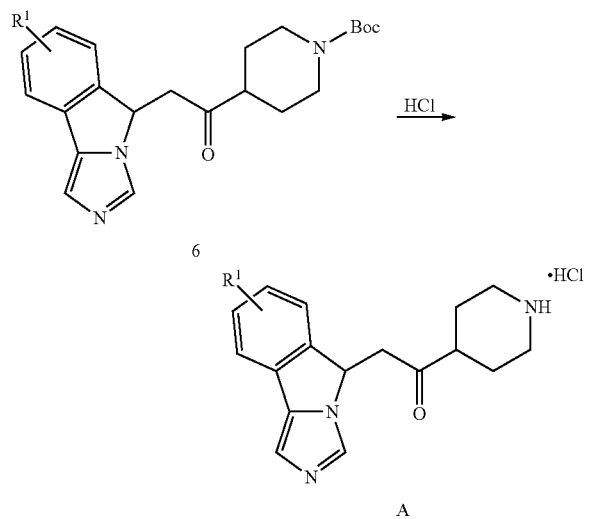

The above-mentioned Suzuki cross-coupling reaction (a) uses palladium as a catalyst, such as Pd(PPh$_3$)$_4$, Pd(dffp)Cl$_2$, Pd(OAc)$_2$, Pd(dba)$_3$/PCy$_3$, PdCl$_2$, Pd(PPh$_3$)$_4$Cl$_2$, etc. Or alternatively, it uses Ni as a catalyst, such as NiCl$_2$(dffp), NiCl$_2$(dffp)/Zn, NiCl$_2$(dffp)/BuLi, NiCl$_2$(PPh$_3$)$_2$/PPh$_3$, NiCl$_2$(NEt$_3$)$_2$, NiCl$_2$(NEt$_3$)$_2$, NiCl(bipy), Ni(TPPS)$_3$, Ni(COD)$_2$, NiCl$_2$(PPh$_3$)$_2$/n-BuLi, Ni{P(OMe)$_3$}$_2$Cl$_2$, NiCl$_2$(PCy$_3$)$_2$, etc. It uses KOAc, K$_3$PO$_4$, K$_2$CO$_3$, NaOH, Ba(OH)$_2$, Na$_2$CO$_3$, CsF or NaHCO$_3$ and the like as a base, the reaction temperature is 25 to 140° C. and the reaction duration is 4 to 72 hours. The solvent used in the reaction is a commonly used solvent such as ethanol, THF, isopropanol, DMSO, dioxane, toluene, water, DME, etc.

The above-mentioned Claisen-Schimidt condensation reaction (b) may use a base such as NaOH, NaOCH$_3$, NaOEt, etc., as a catalyst, or an acid as a catalyst such as sulfuric acid, hydrochloric acid, acetic acid, etc. The reaction temperature is 0 to 80° C., and the reaction duration is 1 to 24 hours. The solvent used in the reaction may be a commonly used solvent such as THF, ethanol, water, etc.

The above-mentioned reaction (c) uses acetic acid, hydrochloric acid and trifluoroacetic acid as de-protection and cyclization reagents, the reaction temperature is 0 to 90° C., and the reaction duration is 2 to 72 hours. The solvent used in the reaction is a commonly used solvent such as water, methanol, ethanol, isopropanol, tetrahydrofuran, dichloromethane, acetone, etc.

The above-mentioned de-protection reaction (d) uses hydrochloric acid, trifluoroacetic acid, p-toluenesulfonic acid, sulfuric acid, methanesulfonic acid, boron trifluoride diethyl etherate, etc., as a de-protection reagent. The reaction temperature is 25 to 100° C., and the reaction duration is 20 minutes to 24 hours. The solvent used in the reaction is a commonly used solvent, such as water, methanol, ethanol, ethyl acetate, dichloromethane, tetrahydrofuran, 1,4-dioxane, N,N-dimethylformamide, etc.

Preparation of Compound of Formula B

According to the difference in X in the structure of the compound of Formula B, it is divided into two conditions: X is O; X is NR$^4$.

When X is O, the compound of Formula B is Compound B(1):

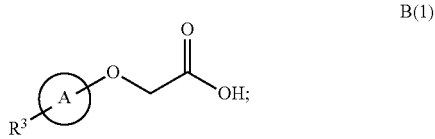

when X is NR$^4$, the compound of Formula B is Compound B(2):

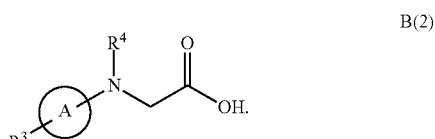

The compound of Formula B(1) may be purchased directly from the market or prepared by the following synthetic methods:

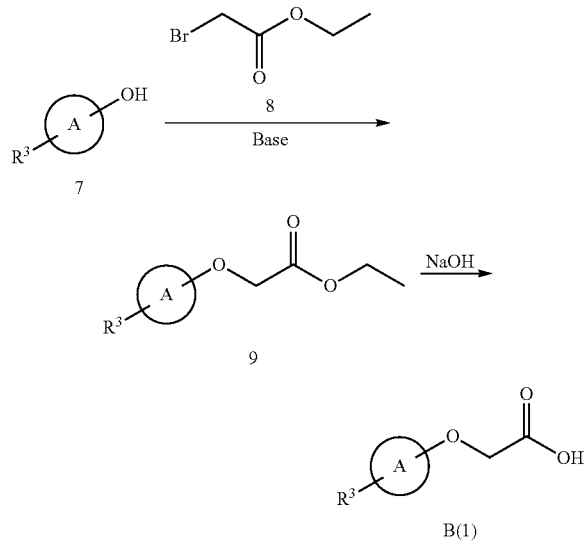

Commercially available Phenol 7 and commercially available Compound 8 undergo a nucleophilic substitution reaction under alkaline conditions to obtain Compound 9. The nucleophilic substitution reaction uses a base such as NaOH, Na$_2$CO$_3$, K$_2$CO$_3$, etc., as a deacidification agent. The reaction temperature is 25 to 140° C., and the reaction duration is 2 to 72 hours. The solvent used in the reaction is a commonly used solvent such as water, methanol, ethanol, acetonitrile, benzene, xylene, acetone, N,N'-dimethylformamide, DMSO, etc.

The obtained Compound 9 is deethylated under the action of a base such as NaOH or LiOH to obtain Compound B (1). The reaction temperature is 0 to 60° C., and the reaction duration is 0.5 to 2 hours. The commonly used solvent in the reaction is water, methanol, ethanol, tetrahydrofuran, N,N'-dimethylformamide, etc.

The compound of Formula B(2) may be purchased directly from the market or prepared by the following synthetic methods:

Commercially available Amine 10 and commercially available Compound 8 undergo a nucleophilic substitution reaction under alkaline conditions to obtain Compound 11. The nucleophilic substitution reaction uses a base such as NaOH, Na$_2$CO$_3$, K$_2$CO$_3$, etc., as a deacidification agent. The reaction temperature is 25 to 140° C., and the reaction duration is 2 to 72 hours. The solvent used in the reaction is a commonly used solvent such as water, methanol, ethanol, acetonitrile, benzene, tetrahydrofuran, xylene, acetone, N,N'-dimethylformamide, DMSO, etc.

The obtained Compound 11 is deethylated under the action of a base such as NaOH or LiOH to obtain Compound B(2). The reaction temperature is 0 to 60° C., and the reaction duration is 0.5 to 2 hours. The commonly used solvent in the reaction is water, methanol, ethanol, tetrahydrofuran, N,N'-dimethylformamide, etc.

In a preferred embodiment, the compound of General Formula I of the present disclosure can be prepared by the following synthetic methods:

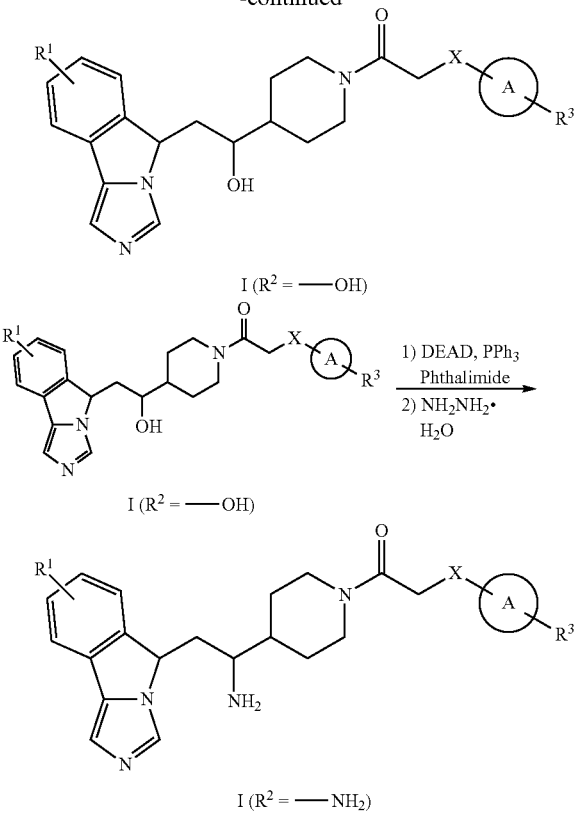

The compound of Formula A is condensed with a compound of Formula B to obtain a compound of Formula C. The condensation reaction uses a peptide condensing agent as a catalyst, such as 1-ethyl-3-(3-dimethylaminopropyl) carbodiimide (EDC), N,N'-dicyclohexylcarbodiimide (DCC), N,N'-carbonyldiimidazole (CDI), O-(7-azabenzotriazole)-N,N,N',N'-tetramethylurea hexafluorophosphate (HATU), etc. The reaction temperature is 0 to 60° C., and the reaction duration is 2 to 72 hours. The solvent used in the reaction is a commonly used solvent such as benzene, toluene, tetrahydrofuran, dioxane, dichloromethane, chloroform, NY-dimethylformamide, etc. If necessary, a base may also be added, such as sodium hydroxide, triethylamine or pyridine.

The intermediate of Formula C is reduced to obtain Compound I ($R^2$=—OH) with a reducing agent such as $NaBH_4$, $KBH_4$, $NaBH(OAc)_3$, $KBH(OAc)_3$, $NaBH_3CN$, etc. The reaction temperature is 0 to 60° C., and the reaction duration is 2 to 72 hours. The solvent used in the reaction is a commonly used solvent such as methanol, ethanol, tetrahydrofuran, etc.

The compound as shown in General Formula I ($R^2$=—OH) is converted to the compound as shown in General Formula I ($R^2$=—$NH_2$) by a Mitsunobu reaction. Diethyl azodicarboxylate (DEAD) and triphenylphosphine are used as activating reagent, phthalimide is used as a nucleophilic reagent, and they are subjected to hydrazinolysis to obtain a compound as shown in General Formula I ($R^2$=—$NH_2$). The reaction temperature is 0 to 25° C., and the reaction duration is 0.5 to 16 hours. The solvent used in the reaction is a commonly used solvent such as tetrahydrothran, diethyl ether, dichloromethane, toluene, ethyl acetate, acetonitrile, N,N'-dimethylformamide, etc.

The compound of General Formula (I) may be purified by a common separation method such as extraction, recrystallization, column chromatography, etc.

The representative compounds of the present disclosure are shown in Table 1 below, in which the number of the compound is the same as the "Example Number" in the embodiment section.

TABLE 1

The Representative Compounds of the Present Disclosure

| Number | Structure | Name |
|---|---|---|
| 7 | 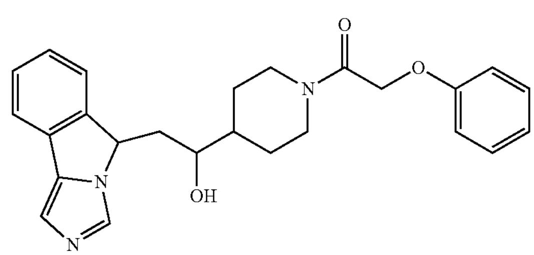 [SMILES: O=C(COc1ccccc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-phenoxyethyl-1-one |
| 11 | 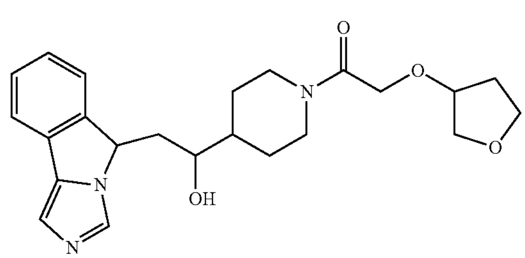 [SMILES: O=C(COC1CCOC1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-((tetrahydrofuran-3-yl)oxy)ethyl-1-one |

TABLE 1-continued

The Representative Compounds of the Present Disclosure

| Number | Structure | Name |
|---|---|---|
| 17 | 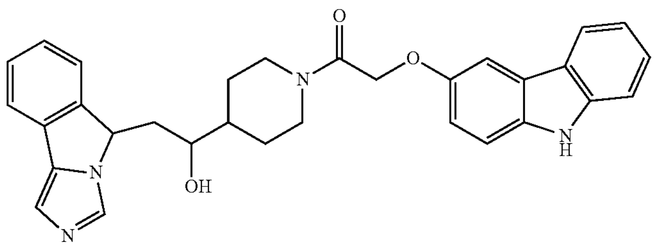 [SMILES: O=C(COc1ccc2[nH]c3ccccc3c2c1)N1CCC(C(O)CC2c3ccccc3-c3cncn32)CC1] | 2-((9H-carbazol-3-yl)oxy)-1-(4-(1-hydroxy-2-(5H-imidazo[5,1-a]isoindol-5-yl)ethyl)piperidin-1-yl)ethyl-1-one |
| 21 | 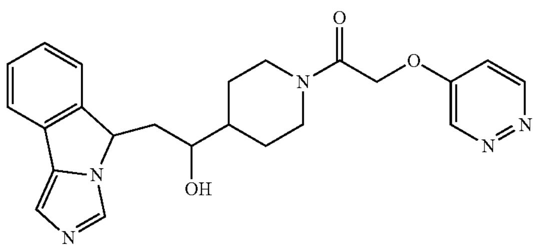 [SMILES: O=C(COc1ccnnc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyridazine-4-yloxy)ethyl-1-one |
| 23 | 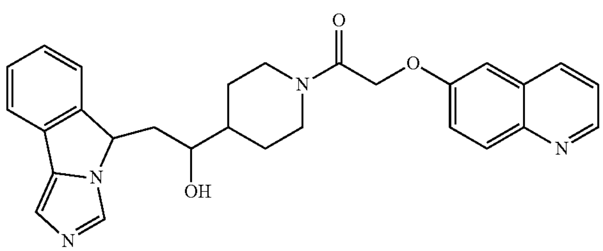 [SMILES: O=C(COc1ccc2ncccc2c1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(quinolin-6-yloxy)ethyl-1-one |
| 26 | 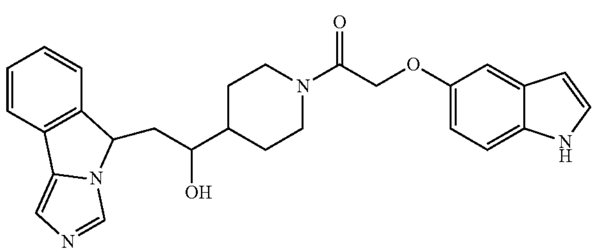 [SMILES: O=C(COc1ccc2[nH]ccc2c1)N1CCC(C(O)CC2c3ccccc3-c3cncn32)CC1] | 2-((1H-indol-5-yl)oxy)-1-(4-(1-hydroxy-2-(5H-imidazo[5,1-a]isoindol-5-yl)ethyl)piperidin-1-yl)-ethyl-1-one |
| 29 | 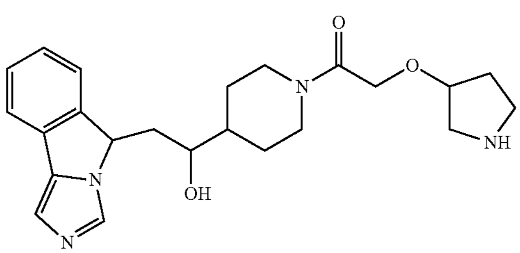 [SMILES: O=C(COC1CCNC1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(pyrrolidine-3-yloxy)ethyl-1-one |
| 33 | 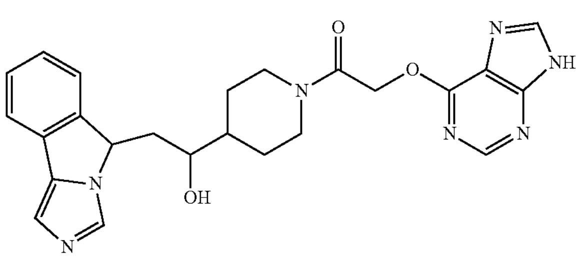 [SMILES: O=C(COc1ncnc2[nH]cnc12)N1CCC(C(O)CC2c3ccccc3-c3cncn32)CC1] | 2-((7H-purin-6-yl)oxy)-1-(4-(1-hydroxy-2-(5H-imidazo[5,1-a]isoindol-5-yl)ethyl)piperidin-1-yl)ethyl-1-one |

TABLE 1-continued

The Representative Compounds of the Present Disclosure

| Number | Structure | Name |
|---|---|---|
| 37 | 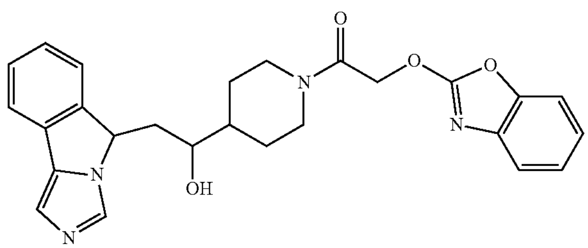 [SMILES: O=C(COc1nc2ccccc2o1)N1CCC(C(O)CC2c3ccccc3-c3cncn32)CC1] | 2-(benzo[d]oxazolin-2-yloxy)-1-(4-(1-hydroxy-2-(5H-imidazo[5,1-a]isoindol-5-yl)ethyl)piperidin-1-yl)ethyl-1-one |
| 39 | 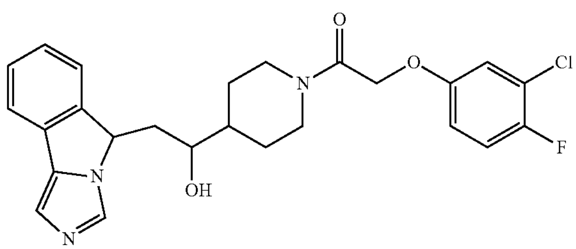 [SMILES: O=C(COc1ccc(F)c(Cl)c1)N1CCC(C(O)CC2c3ccccc3-c3cncn32)CC1] | 2-(3-chloro-4-fluorophenoxy)-1-(4-(1-hydroxy-2-(5H-imidazo[5,1-a]isoindol-5-yl)ethyl)piperidin-1-yl)ethyl-1-one |
| 41 | 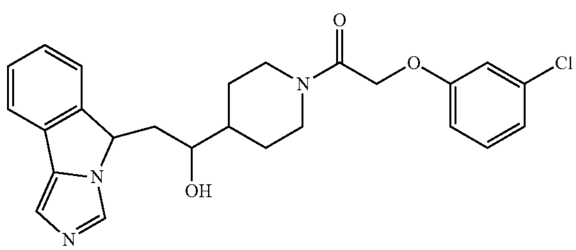 [SMILES: O=C(COc1cccc(Cl)c1)N1CCC(C(O)CC2c3ccccc3-c3cncn32)CC1] | 2-(3-chlorophenoxy)-1-(4-(1-hydroxy-2-(5H-imidazo[5,1-a]isoindol-5-yl)ethyl)piperidin-1-yl)ethyl-1-one |
| 43 | 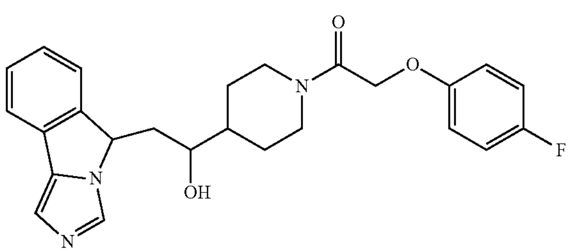 [SMILES: O=C(COc1ccc(F)cc1)N1CCC(C(O)CC2c3ccccc3-c3cncn32)CC1] | 2-(4-fluorophenoxy)-1-(4-(1-hydroxy-2-(5H-imidazo[5,1-a]isoindol-5-yl)ethyl)piperidin-1-yl)ethyl-1-one |
| 46 | 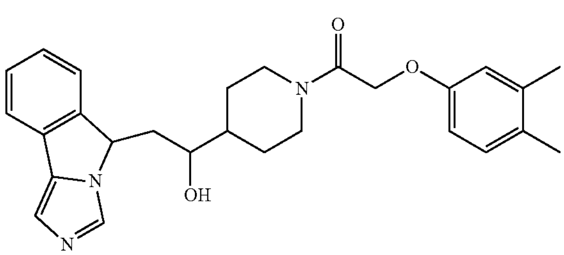 [SMILES: Cc1ccc(OCC(=O)N2CCC(C(O)CC3c4ccccc4-c4cncn43)CC2)cc1C] | 2-(3,4-dimethylphenoxy)-1-(4-(1-hydroxy-2-(5H-imidazo[5,1-a]isoindol-5-yl)ethyl)piperidin-1-yl)ethyl-1-one |
| 48 | 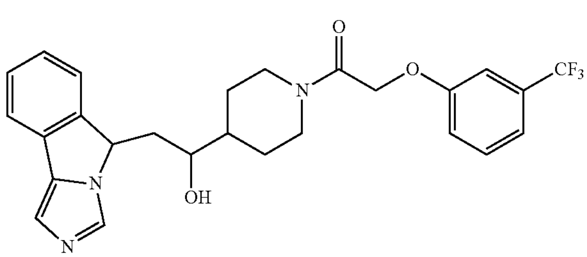 [SMILES: O=C(COc1cccc(C(F)(F)F)c1)N1CCC(C(O)CC2c3ccccc3-c3cncn32)CC1] | 2-(3-trifluoromethylphenoxy)-1-(4-(1-hydroxy-2-(5H-imidazo[5,1-a]isoindol-5-yl)ethyl)piperidin-1-yl)ethyl-1-one |

TABLE 1-continued

The Representative Compounds of the Present Disclosure

| Number | Structure | Name |
|---|---|---|
| 50 | 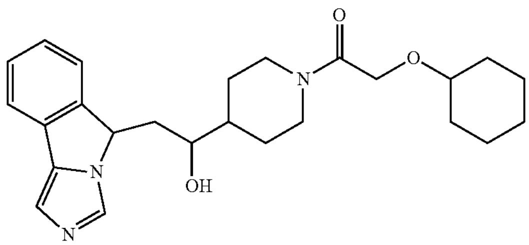 [SMILES: O=C(COC1CCCCC1)N1CCC(C(O)CC2c3ccccc3-c3cncn32)CC1] | 2-(cyclohexyloxy)-1-(4-(1-hydroxy-2-(5H-imidazo[5,1-a]isoindol-5-yl)ethyl)piperidin-1-yl)ethyl-1-one |
| 57 | 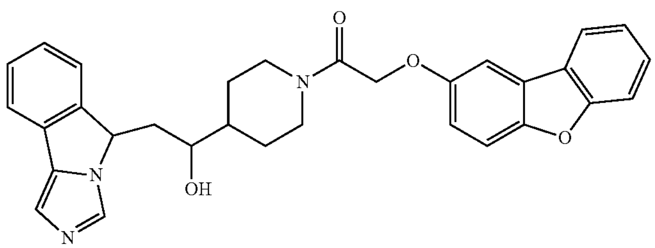 [SMILES: O=C(COc1ccc2oc3ccccc3c2c1)N1CCC(C(O)CC2c3ccccc3-c3cncn32)CC1] | 2-(dibenzo[b,d]furan-2-yloxy)-1-(4-(1-hydroxy-2-(5H-imidazo[5,1-a]isoindol-5-yl)ethyl)piperidin-1-yl)ethyl-1-one |
| 59 | 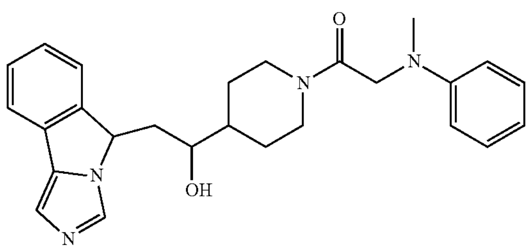 [SMILES: CN(CC(=O)N1CCC(C(O)CC2c3ccccc3-c3cncn32)CC1)c1ccccc1] | 1-(4-(1-hydroxy-2-(5H-imidazo[5,1-a]isoindol-5-yl)ethyl)piperidin-1-yl)-2-(methyl(phenyl)amino)ethyl-1-one |
| 63 | 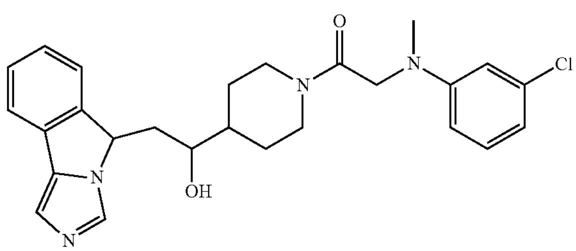 [SMILES: CN(CC(=O)N1CCC(C(O)CC2c3ccccc3-c3cncn32)CC1)c1cccc(Cl)c1] | 2-((3-chlorophenyl)(methyl)amino)-1-(4-(2-(5H-imidazo[5,1-a]isoindol-5-yl)ethyl)piperidin-1-yl)-ethyl-1-one |
| 68 | 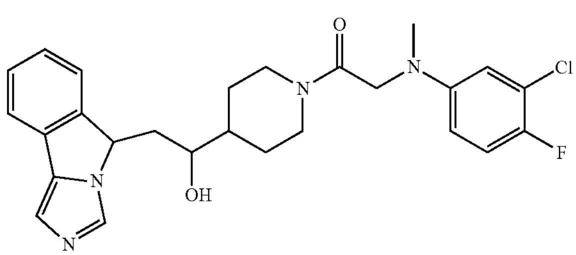 [SMILES: CN(CC(=O)N1CCC(C(O)CC2c3ccccc3-c3cncn32)CC1)c1ccc(F)c(Cl)c1] | 2-((3-chloro-4-fluorophenyl)(methyl)amino)-1-(4-(1-hydroxy-2-(5H-imidazo[5,1-a]isoindol-5-yl)ethyl)piperidin-1-yl)ethyl-1-one |
| 72 | 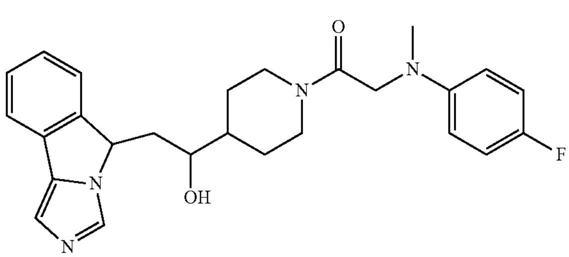 [SMILES: CN(CC(=O)N1CCC(C(O)CC2c3ccccc3-c3cncn32)CC1)c1ccc(F)cc1] | 2-((4-fluorophenyl)(methyl)amino)-1-(4-(1-hydroxy-2-(5H-imidazo[5,1-a]isoindol-5-yl)ethyl)piperidin-1-yl)ethyl-1-one |

TABLE 1-continued

The Representative Compounds of the Present Disclosure

| Number | Structure | Name |
|---|---|---|
| 77 | 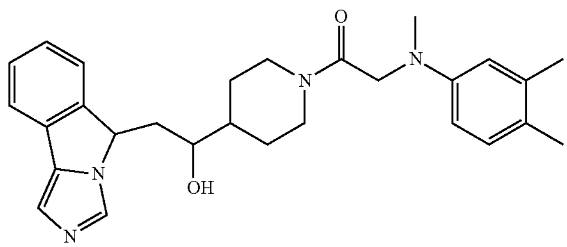 [SMILES: Cc1ccc(N(C)CC(=O)N2CCC(C(O)CC3c4ccccc4-c4cncn43)CC2)cc1C] | 2-((3,4-dimethylphenyl)(methyl)amino)-1-(4-(1-hydroxy-2-(5H-imidazo[5,1-a]isoindol-5-yl)ethyl)piperidin-1-yl)ethyl-1-one |
| 81 | 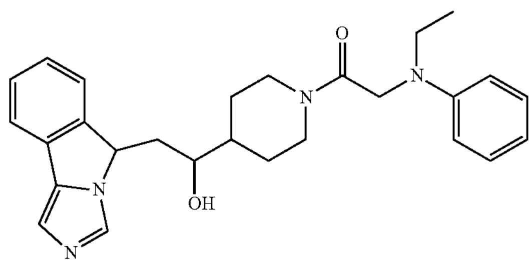 [SMILES: CCN(CC(=O)N1CCC(C(O)CC2c3ccccc3-c3cncn32)CC1)c1ccccc1] | 2-(ethyl(phenyl)amino)-1-(4-(1-hydroxy-2-(5H-imidazo[5,1-a]isoindol-5-yl)ethyl)piperidin-1-yl)ethyl-1-one |
| 85 | 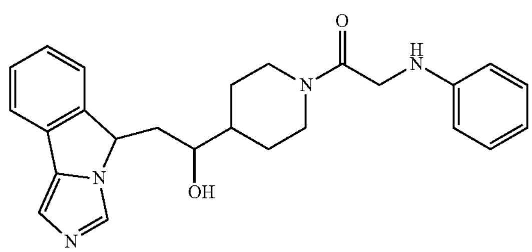 [SMILES: O=C(CNc1ccccc1)N1CCC(C(O)CC2c3ccccc3-c3cncn32)CC1] | 1-(4-(1-hydroxy-2-(5H-imidazo[5,1-a]isoindol-5-yl)ethyl)piperidin-1-yl)-2-(phenylamino)ethyl-1-one |
| 89 | 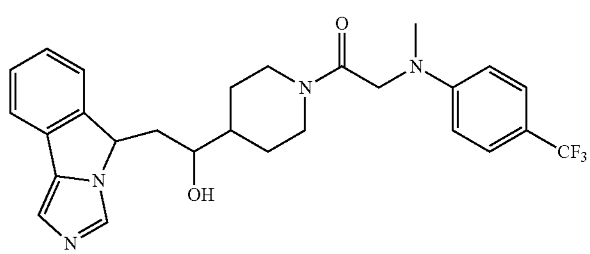 [SMILES: CN(CC(=O)N1CCC(C(O)CC2c3ccccc3-c3cncn32)CC1)c1ccc(C(F)(F)F)cc1] | 1-(4-(1-hydroxy-2-(5H-imidazo[5,1-a]isoindol-5-yl)ethyl)piperidin-1-yl)-2-(methyl(4-trifluoromethylphenyl)amino)ethyl-1-one |
| 94 | 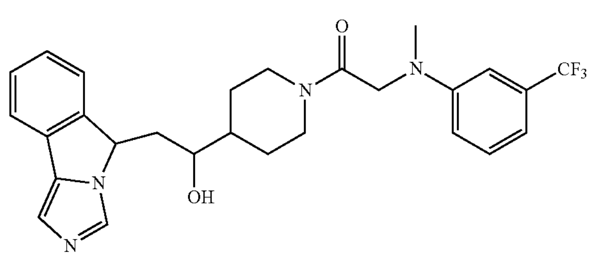 [SMILES: CN(CC(=O)N1CCC(C(O)CC2c3ccccc3-c3cncn32)CC1)c1cccc(C(F)(F)F)c1] | 1-(4-(1-hydroxy-2-(5H-imidazo[5,1-a]isoindol-5-yl)ethyl)piperidin-1-yl)-2-(methyl(3-trifluoromethylphenyl)amino)ethyl-1-one |
| 98 | 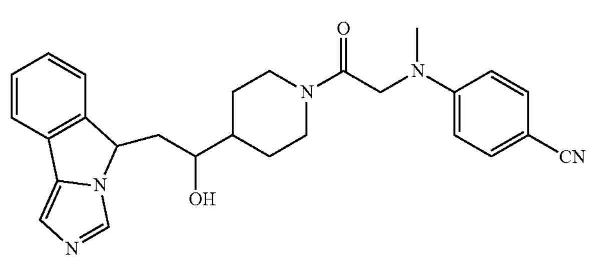 [SMILES: CN(CC(=O)N1CCC(C(O)CC2c3ccccc3-c3cncn32)CC1)c1ccc(C#N)cc1] | 2-((4-cyanophenyl)(methyl)amino)-1-4-(1-hydroxy-2-(5H-imidazo[5,1-a]isoindol-5-yl)ethyl)piperidin-1-yl)ethyl-1-one |

TABLE 1-continued

The Representative Compounds of the Present Disclosure

| Number | Structure | Name |
|---|---|---|
| 102 | 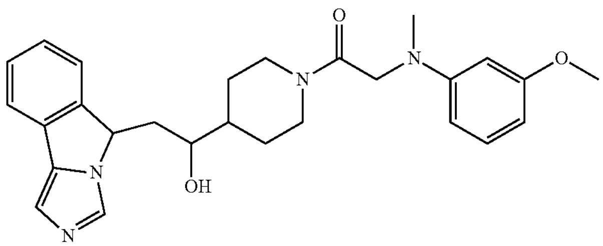 [SMILES: COc1cccc(N(C)CC(=O)N2CCC(C(O)CC3c4ccccc4-c4cncn43)CC2)c1] | 2-((3-methoxyphenyl)(methyl)amino)-1-(4-(1-hydroxy-2-(5H-imidazo[5,1-a]isoindol-5-yl)ethyl)piperidin-1-yl)ethyl-1-one |
| 105 | 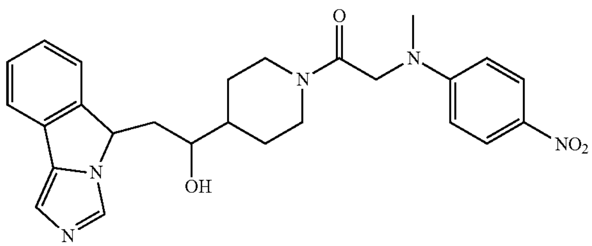 [SMILES: CN(CC(=O)N1CCC(C(O)CC2c3ccccc3-c3cncn32)CC1)c1ccc([N+](=O)[O-])cc1] | 1-(4-(1-hydroxy-2-(5H-imidazo[5,1-a]isoindol-5-yl)ethyl)piperidin-1-yl)-2-(methyl(4-nitrophenyl)atnino)ethyl-1-one |
| 109 | 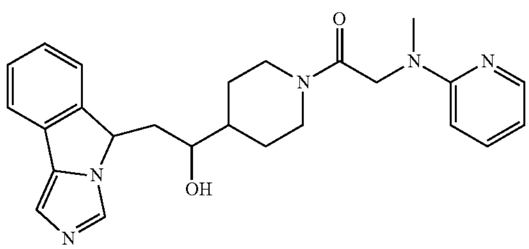 [SMILES: CN(CC(=O)N1CCC(C(O)CC2c3ccccc3-c3cncn32)CC1)c1ccccn1] | 1-(4-(1-hydroxy-2-(5H-imidazo[5,1-a]isoindol-5-yl)ethyl)piperidin-1-yl)-2-(methyl(pyridin-2-yl)amino)ethyl-1-one |
| 113 | 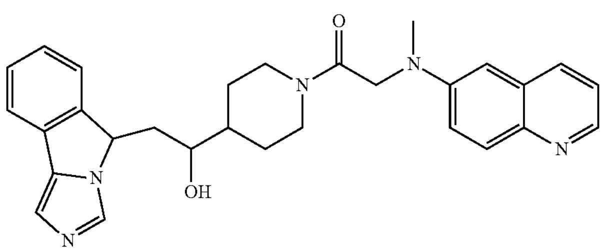 [SMILES: CN(CC(=O)N1CCC(C(O)CC2c3ccccc3-c3cncn32)CC1)c1ccc2ncccc2c1] | 1-(4-(1-hydroxy-2-(5H-imidazo[5,1-a]isoindol-5-yl)ethyl)piperidin-1-yl)-2-(methyl(quinolin-6-yl)amino)ethyl-1-one |
| 119 | 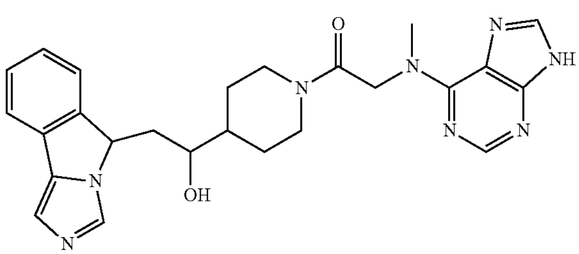 [SMILES: CN(CC(=O)N1CCC(C(O)CC2c3ccccc3-c3cncn32)CC1)c1ncnc2[nH]cnc12] | 1-(4-(1-hydroxy-2-(5H-imidazo[5,1-a]isoindol-5-yl)ethyl)piperidin-1-yl)-2-(methyl(7H-purin-6-yl)amino)ethyl-1-one |
| 124 | 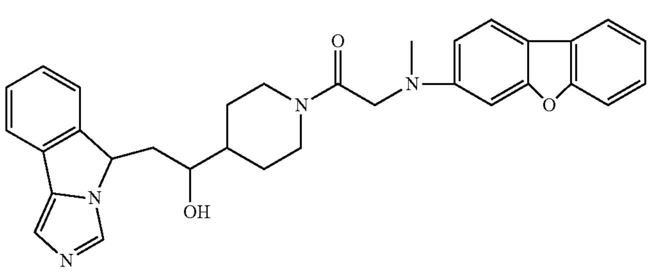 [SMILES: CN(CC(=O)N1CCC(C(O)CC2c3ccccc3-c3cncn32)CC1)c1ccc2c(c1)oc1ccccc12] | 2-(dibenzo[b,d]furan-3-yl(methyl)amino)-1-(4-(1-hydroxy-2(5H-imidazo[5,1-a]isoindol-5-yl)ethyl)piperidin-1-yl)ethyl-1-one |

DETAILED DESCRIPTION

The content of the present disclosure will be further illustrated below with reference to examples, but the scope of protection of the present disclosure is not limited to these examples. The percentages stated in the present disclosure are all percentages by weight unless otherwise specified. The range of values described in the specification, such as units of measurement, reaction conditions, physical state of the compound or percentage, are intended to provide an unambiguous written reference. Those having ordinary skill in the art will still be able to obtain desired results when practicing the present patent, using temperatures, concentrations, amounts, number of carbon atoms, etc. outside of this range or different front a single value.

The full names of the reagent abbreviations used in the examples are as follows:

HATU 2-(7-oxybenzotriazole)-N,N,N',N'-tetramethylurea hexafluorophosphate

DIPEA diisopropylethylamine

DABCO 1,4-diazabicyclo[2.2.2]octane

HOBt 1-hydroxyberizotriazole

EDCI.HCl 1-ethyl-(3-dimethylaminopropyl)carbonyldiimide hydrochloride

DNF NN-dimethylformamide

THF tetrahydrofuran

EA ethyl acetate

DCM dichloromethane

EXAMPLE 1

Preparation of 4-iodo-1-trityl-1H-imidazole

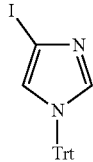

4-Iodo-1H-imidazole (20 g, 103 mmoles) was dissolved in DMF (100 ml), then triethylamine (15.1 mL, 108 mmoles) and triphenylmethyl chloride (27.8 g, 100 mmoles) were added, stirred at room temperature for 48 hours to react, then was poured into iced water (500 mL), and a large amount of solid was precipitated, filtered and dried to obtain a white solid 4-iodo-1-trityl-1H-imidazole (40 g, 91.7 mmol, 88.9%).

LC-MS (m/z): 437 (M+1).

EXAMPLE 2

Preparation of 2-(1-trityl-1H-imidazol-4-yl)benzaldehyde

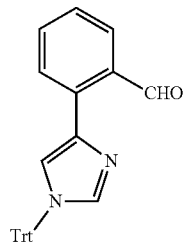

4-Indo-1-trityl-1H-imidazole (38.7 g, 88.8 mmol), (2-formylphenyl)boronic acid (20.0 g, 133 mmol) and $K_3PO_4$ (56.4 g, 266 mmol) were dissolved in 1.4-dioxane (300 ml) and water (60 ml). Nitrogen gas was bubbled through the reaction solution for 5 minutes, then Pd(PPh$_3$)$_4$ (5.12 g, 4.44 mmol) was added, then nitrogen gas was bubbled through the reaction solution for another 5 minutes. The reaction was heated to 90° C. for 16 hours under the protection of nitrogen gas. After the completion of the reaction, the temperature was lowered, it was filtered on diatomite. The filtrate was diluted with water (100 ml) and EA (300 ml), allowed to stand for stratification. The aqueous phase was extracted with EA (300 ml×2). The organic phases were combined and washed with water (100 ml) and saturated brine (100 ml×3). The organic phase was concentrated under reduced pressure to obtain a residue, and was purified by passing through column with PE/EA=3/1 to obtain a light brown ropiness oily substance 2-(1-trityl-1H-imidazol-4-yl)benzaldehyde (15.0 g, 40.8%), LC-MS (m/z): 415 (M+1).

EXAMPLE 3

Preparation of tert-butyl (E)-4-(3-(2-(1-trimethyl-1H-imidazol-4-yl)phenyl)acryloyl)piperidine-1-formate

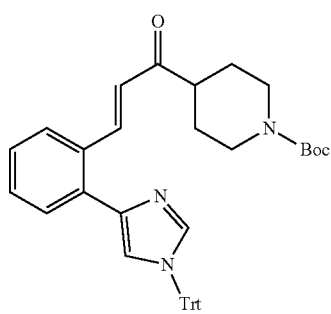

2-(1-Trityl-1H-imidazol-4-yl)benzaldehyde (4.0 g, 9.66 mmol) was dissolved in a mixture of anhydrous THF (20 ml) and anhydrous EtOH (20 ml). The temperature was lowered to 0° C., then EtONa (986 mg, 14.5 mmol) and tert-butyl 4-acetylpiperidine-1-formate (2.29 g, 10.1 mmol) were added. The reaction mixture was then stirred at room temperature overnight. After the reaction was completed and detected by LCMS, the mixture was diluted with iced water (30 ml), THF was evaporated under reduced pressure, and subjected to suction filtration, and the filter cake was drained as much as possible to obtain a white crude solid tert-butyl (E-4-(3-(2-(1-tritylmethyl-1H-imidazol-4-yl)phenyl)acryloyl)piperidine-1-formate (6.0 g), which would be directly used in the next step.

LC-MS (m/z): 624 (M+1).

EXAMPLE 4

Preparation of tert-butyl 4-2-(5H-imidazo[5,1-a])isoindole-5-yl)acetyl)piperidine-1-formate

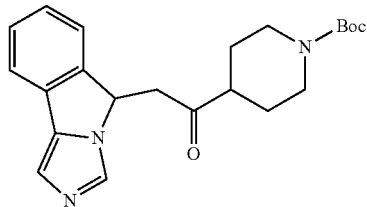 [SMILES: CC(C)(C)OC(=O)N1CCC(C(=O)CC2c3ccccc3-c3cncn32)CC1]

The crude product tert-butyl (E)-4-(3-(2-(1-tritylmethyl-1H-imidazol-4-yl)phenyl)acryloyl)piperidine-1-formate (6.0 g, crude) obtained in the above-mentioned step was dissolved in MeOH (80 ml), glacial acetic acid (15 ml) was added, the temperature was heated to 90° C., and stirred overnight. After the completion of the reaction, the temperature was lowered to room temperature, and the pH was adjusted to 10 with a saturated potassium carbonate solution (30 ml). The reaction mixture was extracted with ethyl acetate (100 ml×3). The organic phases were combined, and washed with water (50 ml) and saturated brine (50 ml×3). The organic phase was dried over anhydrous sodium sulfate, filtered, the solvent was recovered under reduced pressure, and the residue was purified by passing through column (eluent: CH$_2$Cl$_2$/MeOH=50/1) to obtain a light yellow solid tert-butyl 4-(2-(5H-imidazo[5,1-a])isoindole-5-yl)acetyl)piperidine-1-formate (2.7 g, 73.4%, overall yield of two steps).

LC-MS (m/z): 382 (M+1).

EXAMPLE 5

Preparation of 2-(5H-imidazo[5,1-a])isoindol-5-yl-1-(piperidin-4-yl)ethyl-1-one hydrochloride

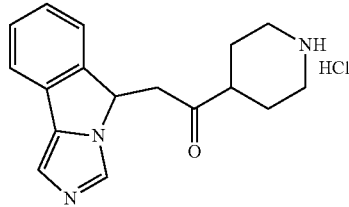 [SMILES: O=C(CC1c2ccccc2-c2cncn21)C1CCNCC1 ; Cl]

tert-butyl 4-(2-(5H-Imidazo[5,1-a]isoindol-5-yl)acetyl)piperidine-1-formate (1.2 g, 3.15 mmol) was dissolved in 1,4-dioxane (20 ml). Then 4N HCl/1,4-dioxane (4 ml) was added. The reaction was allowed to react at room temperature overnight and concentrated under reduced pressure to obtain a light yellow crude solid 2-(5H-imidazo[5,1-a])isoindol-5-yl)-1-(piperidin-4-yl)ethyl-1-one hydrochloride (1.2 g), which would be directly used in the next step.

LC-MS (m/z): 282 (M+1).

EXAMPLE 6

Preparation of 1-(4-(2-(5H-imidazo[5,1-a]isoindol-5-yl)acetyl)piperidin-1-yl)-2-phenoxyethyl-1-one

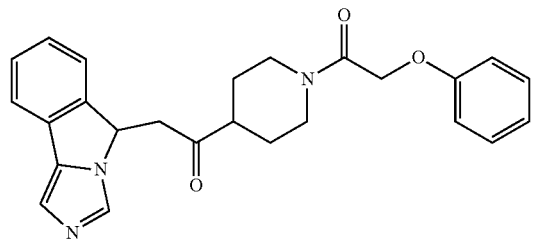 [SMILES: O=C(CC1c2ccccc2-c2cncn21)C1CCN(C(=O)COc2ccccc2)CC1]

2-(5H-Imidazo[5,1-a])isoindol-5-yl)-1-(piperidin-4-yl)ethyl-1-one hydrochloride (360 mg, 1.14 mmol) and DIPEA (0.4 mL, 2.28 mmol) were dissolved in DCM (15 ml), stirred in an ice bath, 2-phenoxyacetic anhydride (340 mg, 1.18 mmol) was added batchwise, the temperature was slowly heated to room temperature, and reacted for 6 hours. Saturated sodium hydrogen carbonate was added and the pH was adjusted to 8 to 10, extracted with ethyl acetate (50 ml), washed with saturated brine (20 ml) and 20 ml of water. The organic phase was dried over anhydrous Na$_2$SO$_4$, filtered and concentrated under reduced pressure. The residue was dissolved in 5 ml of methanol, added dropwise into 50 ml of water, a solid was precipitated, filtered to obtain a compound 1-(4-(2-(5H-imidazo[5,1-a]isoindol-5-yl)acetyl)piperidin-1-yl)-2-phenoxyethyl-1-one (250 mg, the yield was 52.9%).

LC-MS (m/z): 416 (M+1).

EXAMPLE 7

Preparation of 1-(4-(1-hydroxy-2-(5H-imidazo[5,1-a]isoindol-5-yl)ethyl)piperidin-1-yl)-2-phenoxyethyl-1-one

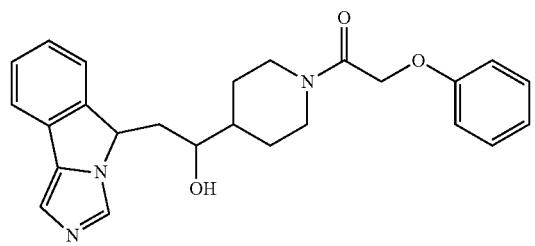 [SMILES: O=C(COc1ccccc1)N1CCC(C(O)CC2c3ccccc3-c3cncn32)CC1]

1-(4-(2-(5H-Imidazo[5,1-a]isoindol-5-yl)acetyl)piperidin-1-yl)-2-phenoxyethyl-1-one (250 mg, 0.60 mmol) was dissolved in 20 ml of methanol, the temperature was lowered to 0° C., NaBH$_4$ (68 mg, 1.8 mmol) was added batchwise. The reaction was allowed to react at room temperature overnight. The mixture was quenched with water, poured into water, a solid was precipitated, filtered, and the obtained solid was dissolved in 5 ml of methanol, and poured into aqueous sodium hydrogen carbonate solution (50 ml). A solid was precipitated, filtered to obtain 1750 (87 mg, yield: 34.7%).

$^1$H NMR (400 MHz, DMSO-d$_6$): δ 7.95 (s, 1H), 7.60 (d, J=7.5 Hz, 1H), 7.57 (d, J=7.5 Hz, 1H), 7.38 (t, J=7.5 Hz. 1H), 7.29-7.25 (m, 3H), 7.12 (s, 1H), 6.94-6.89 (m, 3H), 5.41 (t, J=6.2 Hz, 1H), 5.02 (d, J=5.2 Hz, 1H), 4.81-4.73 (m, 2H), 4.37 (t, J=13.0 Hz, 1H), 3.87 (t, J=13.0 Hz, 1H), 3.71-3.66 (m, 1H), 2.96 (t, J=13.0 Hz, 1H), 2.55 (t, J=13.0 Hz, 1H), 2.10-2.02 (m, 1H), 1.90-1.85 (m, 1H) 1.80-1.77 (m, 1H), 1.61-1.51 (m, 2H), 1.34-1.10 (m, 2H).

LC-MS (m/z): 418 (M+1).

EXAMPLE 8

Preparation of ethyl 2-((tetrahydrofuran-3-yl)oxy)acetate

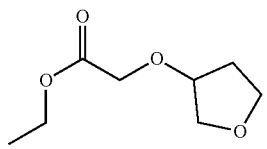

At 0° C., NaH (6.81 g, 170 mmol) was added into THF (60 ml). Then after 3-hydroxytetrahydrofuran (5.00 g, 56.8 mmol) was added, the mixture was stirred at 0° C. for 0.5 hours to react, and ethyl 2-bromopropionate (19.0 g, 114 mmol) was added. The reaction solution was stirred at room temperature overnight and concentrated. The residue was diluted with EA (100 ml), washed with water (50 ml) and saturated brine (50 ml). The organic phase was dried over anhydrous sodium sulfate, filtered and concentrated under reduced pressure. The residue was purified by passing through column with PE/EA=20/1-10/1 to obtain a yellow oily substance ethyl 2-((tetrahydrofuran-3-yl)oxy)acetate (3.50 g, 20.1 mmol, 35.4%).

LC-MS (m/z): 175 (M+1).

EXAMPLE 9

Preparation of 2-((tetrahydrofuran-3-yl)acetic acid

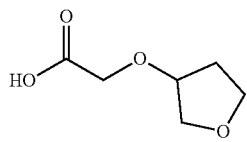

Ethyl 2-((tetrahydrofuran-3-yl)oxy)acetate (1.20 g, 6.90 mmol) and KOH (10.4 ml, 20.7 mmol, 2.0 M in water) were dissolved in MeOH (30 ml), stirred at 80° C. for 6 hours to react. After a portion of the reaction solution was concentrated, the pH was adjusted to 5.0 using concentrated hydrochloric acid. The mixture was extracted with DCM/MeOH (v/v, 5/1, 100 ml). The organic phase was dried over anhydrous sodium sulfate, filtered and concentrated under reduced pressure to obtain 2-((tetrahydrofuran-3-yl)oxy) acetic acid (350 mg), which would be directly used in the next step.

LC-MS (m/z): 147 (M+1).

EXAMPLE 10

Preparation of 1-(4-(2-(5H-imidazo[5,1-a]isoindol-5-yl)acetyl)piperidin-tetrahydrofuran-3-yl)oxy)ethyl-1-one

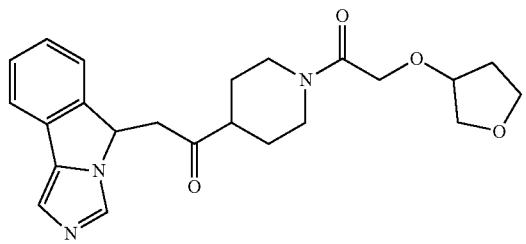 [SMILES: O=C(CC1c2ccccc2-c2cncn21)C1CCN(C(=O)COC2CCOC2)CC1]

2-((Tetrahydrofuran-3-yl)oxy)acetic acid (50 mg, 0.158 mmol), 2-(5H-imidazo[5,1-a]isoindol-5-yl)-1-(piperidin-4-yl)ethyl-1-one hydrochloride (50 mg, crude), HATU (120 mg, 0.316 mmol) and DIPEA (61.1 mg, 0.474 mmol) were dissolved in DMF (5 ml), stirred at room temperature overnight to react, diluted with ethyl acetate (50 ml), washed with water (10 ml) and saturated brine (10 ml×3). The organic phase was dried over anhydrous sodium sulfate, filtered and concentrated to obtain a residue, purified by passing through column with DCM/MeOH=10/1 to obtain 1-(4-(2-(5H-imidazo[5,1-a]isoindol-5-yl)acetyl)piperidin-1-yl)-2-((tetrahydrofuran-3-yl)oxy)ethyl-1-1-one (100 mg), which would be directly used in the next step.

LC-MS (m/z): 410 (M+1).

EXAMPLE 11

Preparation of 1-(4-(1-hydroxy-2-(5H-imidazo[5,1-a]isoindol-5-yl)ethyl)piperidin-1-yl)-2-((tetrahydrofuran-3-yl) oxy)ethyl-1-one

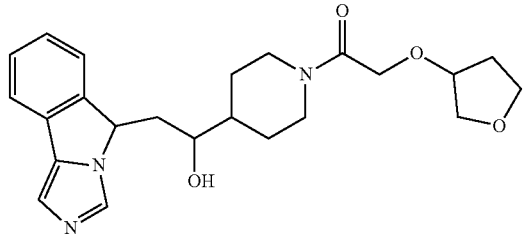 [SMILES: O=C(COC1CCOC1)N1CCC(C(O)CC2c3ccccc3-c3cncn32)CC1]

1-(4-(2-(5H-Imidazo[5,1-a]isoindol-5-yl)acetyl)piperidin-1-yl)-2-((tetrahydrofuran-3-yl) oxy)ethyl-1one (100 mg, crude) was dissolved in methanol (10 ml). The temperature was lowered to 0° C., sodium borohydride (18.0 mg, 0.474 mmol) was slowly added, and the mixture was stirred at the temperature for 1 hour to react, and the reaction was quenched with water (10 ml). The reaction solution was concentrated to obtain a residue. Preparative chromatography was used to prepare a white solid compound 1-(4-(1-hydroxy-2-(5H-imidazo[5,1-a]isoindol-5-yl)ethyl)piperidin-1-yl)-2-((tetrahydrofuran-3-yl)oxy)ethyl-1one (10.0 mg, 0.024 mmols, overall yield 2.47% of the three steps).

¹H NMR (500 MHz, DMSO-d6) δ 7.94 and 7.91 (s, 1H), 7.60 (d, J=7.5 Hz, 1H), 7.56 and 7.50 (d, J=7.7 Hz, 1H), 7.38 (t, J=7.5 Hz, 1H), 7.27 (t, J=7.4 Hz, 1H), 7.14 and 7.12 (s, 1H), 5.48-5.34 (m, 1H), 5.14 and 5.02 (d, J=4.9 Hz, 1H), 4.45-4.29 (m, 1H), 4,19-4.00 (m, 3H), 3.88-3.75 (m, 1H), 3.75-3.56 (m, 5H), 2.88 (t, J=12.9 Hz, 1H), 2.45 (t, J=12.2 Hz, 1H), 2.26-2.02 (m, 1), 1.97-1.83 (m, 3H), 1.82-1.71 (m, 1H), 1.61-1.47 (m, 2H), 1.28-1.19 (m, 1H), 1.18-1.04 (m, 1H) ppm.

LC-MS (m/z): 412 (M+1).

EXAMPLE 12

Preparation of 3-methoxy-9H-carbazole

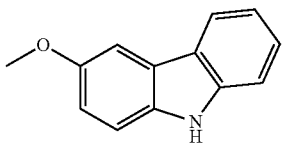

6-Methoxy-2,3,4,9-tetrahydro-1H-carbazole (3.00 g, 14.9 mmol) and 12 (948 mg, 3.73 mmol) were dissolved in DMSO (30 ml), the temperature was heated to 90° C., and reacted overnight. After completion of the reaction, it was diluted with ethyl acetate (300 ml). The organic phase was washed with saturated brine (50 ml×3), dried over anhydrous sodium sulfate, filtered and concentrated under reduced pressure. The residue was purified by passing through column with eluent PE/EA=10/1-5/1 to obtain a white solid 3-methoxy-9H-carbazole (345 mg, 1.75 mmol, 11.8%).

LC-MS (m/z): 198 (M+1).

EXAMPLE 13

Preparation of 3-hydroxy-9H-carbazole

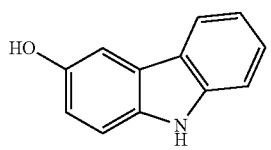 [SMILES: Oc1ccc2[nH]c3ccccc3c2c1]

3-Methoxy-9H-carbazole (345 mg, 1.75 mmol) was dissolved in a solution of hydrobromic acid (5 ml) and acetic acid (20 ml), heated under reflux for 2 hours to react. The temperature was lowered to room temperature, a portion of the solvent was concentrated, the pH was adjusted to pH=9.0 using saturated sodium hydrogen carbonate solution, and extracted with ethyl acetate (50 ml). The organic phase was washed with saturated brine, dried over anhydrous sodium sulfate, filtered and concentrated under reduced pressure to obtain 3-hydroxy-9H-carbazole (300 mg, 1.64 mmol, 93.7%).

LC-MS (m/z): 184 (M+1).

EXAMPLE 14

Preparation of ethyl 2((9H-carbazol-3-yl)oxy)acetate

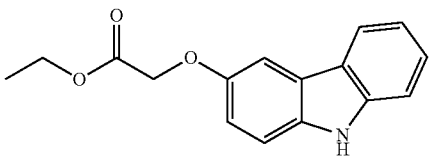 [SMILES: CCOC(=O)COc1ccc2[nH]c3ccccc3c2c1]

3-Hydroxy-9H-carbazole (300 mg, 1,64 mmol), ethyl 2-bromopropionate (329 mg, 1.97 mmol) and K₂CO₃ (272 mg, 1.97 mmol) were dissolved in DMF (10 ml), stirred at room temperature overnight. The reaction solution was diluted with ethyl acetate (80 ml) and washed with saturated brine (20 ml×3). The organic phase was dried over anhydrous sodium sulfate, filtered, and concentrated under reduced pressure. The residue was passed through column with eluent ethyl acetate/petroleum ether=1/10 to obtain ethyl 2-((9H-carbazol-3-yl)oxy)acetate (340 mg, 1.26mmol, 77%), which would be directly used in the next step.

LC-MS (m/z): 270 (M+1).

EXAMPLE 15

Preparation of 2((9H-carbazol-3-yl)oxy)acetic acid

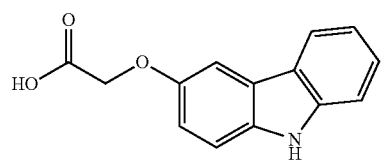 [SMILES: O=C(O)COc1ccc2[nH]c3ccccc3c2c1]

Ethyl 2-((9H-carbazol-3-yl)oxy)acetate (154 mg, 0.572 mmol) was dissolved in 2N sodium hydroxide solution (0.86 mL, 1.72 mmol), MeOH (5 ml) was added, stirred at room temperature for 4 hours to react. A portion of the solvent in the reaction mixture was concentrated, and the reaction mixture was adjusted to pH=5.0 using concentrated hydrochloric acid, and extracted with ethyl acetate (30 ml). The organic phase was washed with brine (15 ml), dried over anhydrous sodium sulfate, filtered and concentrated under reduced pressure to obtain crude 2-((9H-carbazol-3-yl)oxy) acetic acid (200 mg), which would be directly used in the next step.

LC-MS (m/z): 242 (M+1).

EXAMPLE 16

Preparation of 1-(4-(2-(5H-imidazo[5,1-a]isoindol-5-yl)acetyl)piperidin-1yl)-2-((9H-carbazol-3-yl)oxy)ethyl-1-one

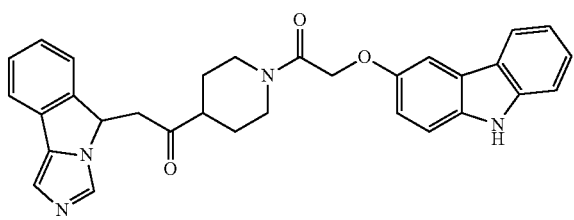

1-4-(2-(5H-imidazo[5,1-a]isoindol-5-yl)acetyl)piperidin-1-yl)-2-((9H-carbazol-3-yl)oxy)ethyl-1one (90 mg, crude) was prepared from 2-((9H-carbazol-3-yl)oxy)acetic acid (45.7 mg, 0.190 mmol) and 2-(5H-imidazo[5,1-a]isoindol-5-yl)-1-(piperidin-4-yl)ethyl-1-one hydrochloride (50 mg, 0.158 mmol) according to the steps similar to those in Example 10.

LC-MS (m/z): 505 (M+1).

EXAMPLE 17

Preparation of 2-((9H-carbazol-3-yl)oxy)-1-(4-(1-hydroxy-2-(5H-imidazo[5,1-a]isoindol-5-yl)ethyl)piperidin-1-yl)ethyl-1-one

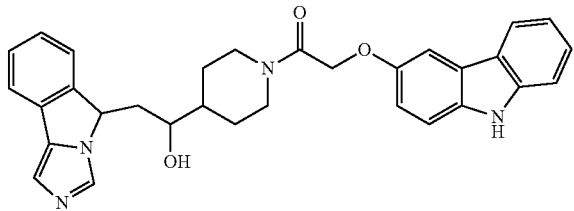 [SMILES: O=C(COc1ccc2[nH]c3ccccc3c2c1)N1CCC(C(O)CC2c3ccccc3-c3cncn32)CC1]

The white solid 2-((9H-carbazol-3-yl)oxy)-1-(4-(1-hydroxy-2-(5H-imidazo[5,1-a]isoindol-5-yl)ethyl)piperidin-1-yl)ethyl-1-one (21 mg, the overall yield of the two steps was 26.3%) was prepared from 1-(4-(2-(5H-imidazo[5,1-a]isoindol-5-yl)acetyl)piperidin-1yl)-2-((9H-carbazol-3-yl)oxy)ethyl-1-one (90 mg, crude) according to the steps similar to those in Example 11.

$^1$H NMR (500 MHz, DMSO-d6) δ 11.05 (s, 1H), 8.04 (d, J=7.6 Hz, 7.95 and 7.92 (s, 1H), 7.66 (s, 1H), 7.63-7.47 (m, 2H), 7.44 (d, J=8.1 Hz, 1H), 7.42-7.31 (m, 3H), 7.27 (t, J=7.5 Hz, 1H), 7.18-7.07 (m, 2H), 7.04 (d, J=8.8 Hz, 1H), 5.48-5.34 (m, 1H), 5.19-5.01 (m, 1H), 4.90-4.73 (m, 2H), 4.48-4.34 (m, 1H), 4.06-3.90 (m, 1H), 3.76-3.66 (m, 1H), 3.01 (t, J=13.2 Hz, 1H), 2.54 (t, J=12.7 Hz, 2.27-2.08 (m, 1H), 1.96-1.50 (m, 4H), 1.43 1.31 (m, 1H), 1.25-1.10 (m, 1H) ppm.

LC-MS (m/z): 507 (M+1).

EXAMPLE 18

Preparation of ethyl 2-(pyridazin-4-yloxy)acetate

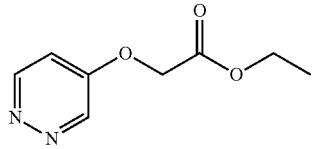

4-Hydroxypyridazine (2.00 g, 20.8 mmol), ethyl 2-bromoacetate (5.21 g, 31.2 mmol) and K$_2$CO$_3$ (4.31 g, 31.2 mmol) were added into acetonitrile (30 ml), heated under reflux for 4 hours to react. The reaction solution was concentrated under reduced pressure, purified by passing through column with ethyl acetate/petroleum ether=1/10 to obtain ethyl 2-(pyridazin-4-yloxy)acetate (1.40 g, 7.69 mmol, 37.0%).

LC-MS (m/z): 183 (M+1).

EXAMPLE 19

Preparation of 2-(pyridazin-4-yloxy)acetic acid

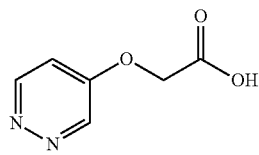 [SMILES: O=C(O)COc1ccnnc1]

2-(Pyridazin-4-yloxy)acetic acid (300 mg, crude) was prepared from ethyl 2-(pyridazin-4-yloxy)acetate (200 mg, 1.10 mmol) according to the steps similar to those in Example 15.

LC-MS (m/z): 155 (M+1).

EXAMPLE 20

Preparation of 1-(4-(2-(5H-imidazo[5,1-a]isoindol-5-yl)acetyl)piperidin-1-yl)-2-(pyridazin-4-yloxy)ethyl-1-one

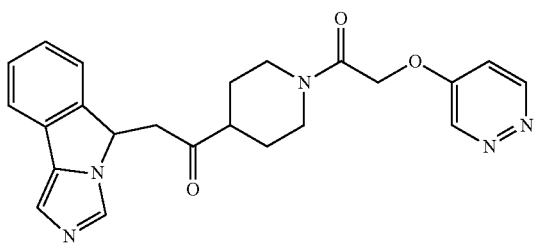 [SMILES: O=C(CC1c2ccccc2-c2cncn21)C1CCN(C(=O)COc2ccnnc2)CC1]

2-(Pyridazin-4-yloxy)acetic acid (50 mg, 0.158 mmol), 2-(5H-imidazo[5,1-a]isoindol-5-yl)-1-(piperidin-4-yl)ethyl-1-one hydrochloride (50 mg, crude), HATU (120 mg, 0.316 mmol) and DIPEA (61.1 mg, 0.474 mmol) were added into 5 ml of DMF, stirred at room temperature overnight. The reaction solution was diluted with 50 ml of ethyl acetate, and then washed with 10 ml of water and saturated brine (10 ml×3). The organic phase was dried over anhydrous Na₂SO₄, filtered and concentrated under reduced pressure. The residue was purified by passing through column with dichloromethane/methanol=10/1 to obtain a crude compound 1-(4-(2-(5H-imidazo[5,1-a]isoindol-5-yl)acetyl)piperidin-1-yl)-2-(pyridazin-4-yloxy)ethyl-1-one (75 mg, crude), which would be directly used in the next step.

LC-MS (m/z): 418 (M+1).

EXAMPLE 21

Preparation of 1-(4-(1-hydroxy-2-(5H-imidazo[5,1-a]isoindol-5-yl)ethyl)piperidin-1-yl)-2-(pyridazine-4-yloxy)ethyl-1one

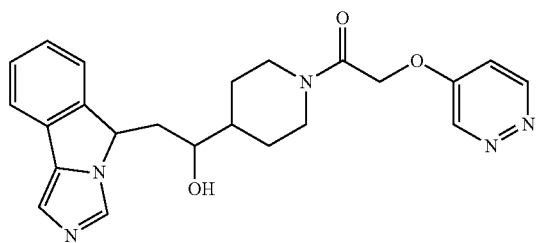 [SMILES: O=C(COc1ccnnc1)N1CCC(C(O)CC2c3ccccc3-c3cncn32)CC1]

1-(4-(2-(5H-Imidazo[5,1-a]isoindol-5-yl)acetyl)piperidin-1yl)-2-(pyridazin-4-yloxy)ethyl-1-one (75 mg, crude) obtained in Example 20 was dissolved in 10 ml of methanol. The temperature was lowered to 0° C., NaBH₄ (18.0 mg, 0.474 mmol) was added, reacted at the temperature for 1 hour. The reaction was quenched with water (10 ml), and concentrated under reduced pressure to obtain a residue. Preparative chromatography was used to prepare a white solid 1-(4-(1-hydroxy-2-(5H-imidazo[5,1-a]isoindol-5-yl)ethyl)piperidin-1-yl)-2-(pyridazine-4-yloxy)ethyl-1one (28.0 mg, 0.067 mmols, the overall yield of the two steps was 20.6%).

¹H NMR (500 MHz, DMSO-d6) δ 8.10 (dd, J=7.8, 1.5 Hz, 1H), 7.98-7.89 (m, 1H), 7.73 (d, J=3.1 Hz, 7.61 (d, J=7.6 Hz, 1H), 7.57 and 7.51 (d, J=7.9 Hz, 1H), 7.39 (t, J=7.5 Hz, 1H), 7.28 (t, J=7.5 Hz, 1H), 7.15 and 7.12 (s, 1H), 6.35 (dd, J=7.8, 3.1 Hz, 1H), 5.48-5.36 (m, 1H), 5.21-5.01 (m, 3H), 4.42-4.27 (m, 1H), 3.88-3.75 (m, 1H), 3.74-3.67 (m, 1H), 2.98 (t, J=13.1 Hz, 1H), 2.55 (t, J=12.6 Hz, 1H), 2.27-2.03 (m, 1H), 1.92-1.52 (m, 4H), 1.38-1.25 (m, 1H), 1.20-1.10 (m, 1H) ppm, LC-MS (m/z): 420 (M+1).

EXAMPLE 22

Preparation of 1-(4-(2-(5H-imidazo[5,1-a]isoindol-5-yl)acetyl)piperidin-1-yl)-2-(quinolin-6-yloxy)ethyl-1-one

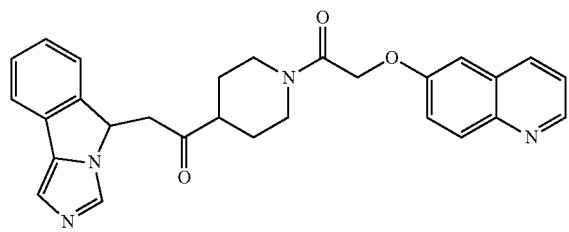 [SMILES: O=C(CC1c2ccccc2-c2cncn21)C1CCN(C(=O)COc2ccc3ncccc3c2)CC1]

1-(4-(2-(5H-imidazo[5,1-a]isoindol-5-yl)acetyl)piperidin-1yl)-2-(quinolin-6-yloxy)ethyl-1-1-one (50 mg, crude) was prepared from 2-(quinolin-6-yloxy)acetic acid (54 mg, 0.267 mmol) and 2-(5H-imidazo[5,1-a]isoindol-5-yl)-1-(piperidin-4-yl)ethyl-1-one hydrochloride (50 mg, 0.158 mmol) according to the steps similar to those in Example 20.

LC-MS (m/z): 467 (M+1).

EXAMPLE 23

Preparation of 1-(4-(1-hydroxy-2-(5H-imidazo[5,1-a]isoindol-5-yl)ethyl)piperidin-1yl)-2-(quinolin-6-yloxy)ethyl-1-one

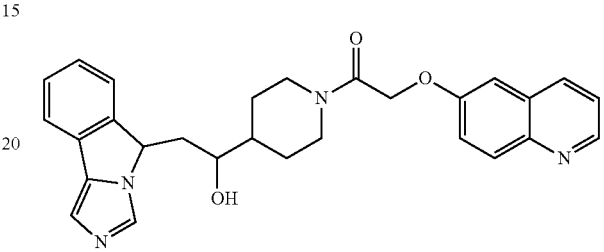

White solid 1-(4-(1-hydroxy-2-(5H-imidazo[5,1-a]isoindol-5-yl)ethyl)piperidin-1-yl)-2-(quinolin-6-yloxy)ethyl-1-one (30 mg, the overall yield of the two steps was 58%) was prepared from 1-(4-(2-(5H-imidazo[5,1-a]isoindol-5-yl)acetyl)piperidin-1-yl)-2-(quinolin-6-yloxy)ethyl-1-one (50 mg, crude) (50 mg, crude) according to the steps similar to those in Example 21.

¹H NMR (500 MHz, DMSO-d6) δ 9.32 and 9.30 (s, 1H), 8.85 (d, J=3.3 Hz, 1H), 8.39 (d, J=7.9 Hz, 1H), 8.00 (d, J=9.2 Hz, 1H), 7.94-7.92 (m, 1H), 7.87 (d, J=7.2 Hz, 1H), 7.74 and 7.67 (d, J=8.0 Hz, 1H), 7.61 (dd, J=8.3, 4.5 Hz, 1H), 7.58-7.52 (m, 3H), 7.41 (d, J=2.5 Hz, 1H), 5.79 (t, J=8.0 Hz, 1H), 5.06-4.89 (m, 2H), 4.40 (t, J=13.0 Hz, 1H), 4.01-3.86 (m, 3H), 3.03 (t, J=12.8 Hz, 1H), 2.65-2.53 (m, 1H), 2.23-2.12 (m, 1H), 2.12-1.99 (m, 1H), 1.81 (t, J=15.3 Hz, 1H), 1.69-1.53 (m, 2H), 1.43-1.24 (m, 1H), 1.22-1.06 (m, 1H) ppm.

LC-MS (m/z): 469 (M+1).

EXAMPLE 24

Preparation of 2-((1H-indol-5-yl)oxy)acetic acid

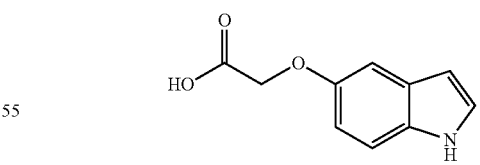

Ethyl 2-((1H-indol-5-yl)oxy acetate (200 mg, 0.913 mmol) was dissolved in methanol (10 ml). The temperature was lowered to 0° C., and then 2.0 M sodium hydroxide solution (0.915 ml, 1.83 mmol) was added. The reaction solution was reacted at room temperature for 2 hours, 20 ml of water was added, freeze-dried to obtain a white solid 2-((1H-indol-5-yl)oxy)acetic acid (200 mg, crude), which would be directly used in the next step.

LC-MS (m/z): 192 (M+1).

EXAMPLE 25

Preparation of 2-((1H-indol-5-yl)oxy)-1-(4-(2-(5H-imidazo[5,1-a]isoindol-5-yl)acetyl)piperidine-1-yl)-ethyl-1-one

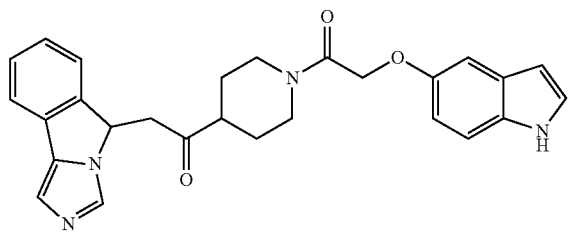

2-((1H-indol-5-yl)oxy)-1-(4-(2-(5H-imidazo[5,1-a]isoindol-5-yl)acetyl)piperidine-1-yl)-ethyl-1-one (70 mg, crude) was prepared from 2-((1H-indol-5-yl)oxy)acetic acid (90.4 mg, 0.473 mmol) and 2-(5H-imidazo[5,1-a]isoindol-5-yl)-1-(piperidin-4-yl)ethyl-1one hydrochloride (50 mg, 0.158 mmol) according to the steps similar to those in Example 20.

LC-MS (m/z): 455 (M+1).

EXAMPLE 26

Preparation of 2-((1H-indol-5-yl)oxy)-1-(4-(1-hydroxy-2-(5H-imidazo[5,1-a]isoindol-5-yl)ethyl)piperidin-1-yl)ethyl-1-one

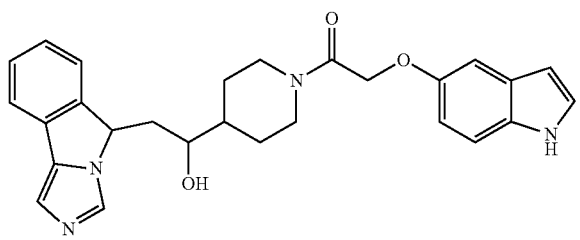 [SMILES: O=C(COc1ccc2[nH]ccc2c1)N1CCC(C(O)CC2c3ccccc3-c3cncn32)CC1]

White solid 2-(1H-indol-5-yl)oxy)-1-(4-(1-hydroxy-2-(5H-imidazo[5,1-a]isoindol-5-yl) ethyl)piperidin-1yl)-ethyl-1-one (22 mg, the overall yield of the two steps was 27%) was prepared from 2-((1H-indol-5-yl)oxy)-1-(4-(2-(5H-imidazo[5,1-a]isoindol-5-yl)acetyl)piperidine-1-yl)-ethyl-1one (70 mg, crude) according to the steps similar to those in Example 21.

$^1$H NMR (500 MHz, DMSO-d6) δ 10.91 (s, 1H), 7.94 and 7.92 (s, 1H), 7.66-7.45 (m, 2H), 7.38 (t, J=7.5 Hz, 1H), 7.28-7.25 (m, 3H), 7.14 and 7.12 (s, 1H), 7.03 (s, 1H), 6.74 (d, J=8.5 Hz, 1H), 6.31 (s, 1H), 5.38 (t, J=6.0 Hz, 1H), 5.12-5.00 (m, 1H), 4.77-4.57 (m, 2H), 4.47-4.28 (m, 1H), 4.01-3.85 (m, 1H), 3.72-3.68 (m, 1H), 2.97 (t, J=12.3 Hz, 1H), 2.26-1.98 (m, 1H), 1.94-1.72 (m, 2H), 1.67-1.48 (m, 2H), 1.34-1.08 (m, 2H) ppm.

LC-MS (m/z) 457 (M+1).

EXAMPLE 27

Preparation of tert-butyl 3-(2-(4-(2-(5H-imidazo[5,1-a]isoindol-5-yl)acetyl)piperidin-1-yl)2-oxoethoxy)pyrrolidine-1-formate

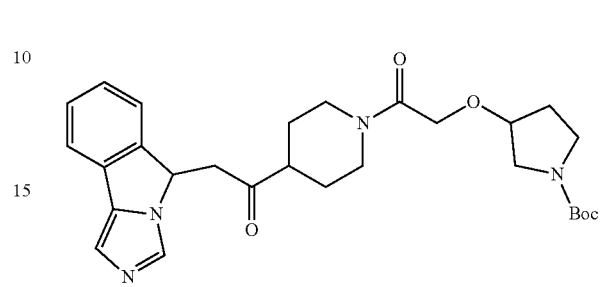

tert-butyl 3-(2-(4-(2-(5H-imidazo[5,1-a]isoindol-5-yl)acetyl)piperidin-1-yl)2-oxoethoxy)pyrrolidine-1-formate (60 mg, 53.6%) was prepared from 2-(1-(tert-butoxycarbonyl)pyrrolidin-3-yl)oxy)acetic acid (59.5 mg, 0.243 mmol) and 2-(5H-imidazo[5,1-a]isoindol-5-yl)-1-(piperidin-4-yl)ethyl-1-one hydrochloride (70 mg, 0.221 mmol) according to the steps similar to those in Example 10.

LC-MS (m/z): 509 (M+1).

EXAMPLE 28

Preparation of 1-(4-(2-(5H-imidazo[5,1-a]isoindol-5-yl)acetyl)piperidin-1yl)-2-(pyrrolidin-3-yloxy)ethyl-1-one

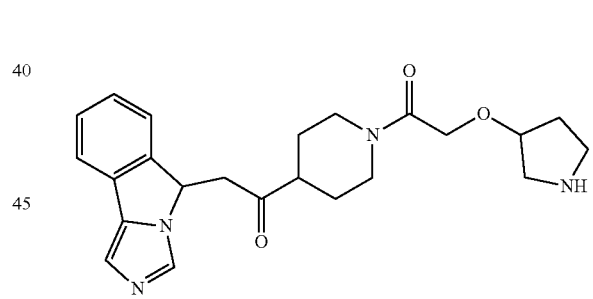

tert-butyl 3-(2-(4-(2-(5H-Imidazo[5,1-a]isoindol-5-yl)acetyl)piperidin-1-yl)2-oxoethoxy)pyrrolidine-1-formate (60 mg, 0.118 mmol) was dissolved in 1,4-dioxane (10 ml). The temperature was lowered to 0° C., 1,4-dioxane in hydrochloride solution (0.118 mL, 4 M, 0.472 mmol) was added. The reaction solution was stirred at room temperature for 2 hours, adjusted to pH=7 to 8 with saturated sodium bicarbonate. The reaction solution was extracted with ethyl acetate (30 ml×3). The organic phases were combined, washed with saturated brine, dried over anhydrous sodium sulfate, filtered, concentrated under reduced pressure to obtain a crude light yellow solid 1-(4-(2-(5H-imidazo[5,1-a]isoindol-5-yl)acetyl)piperidin-1yl)-2-(pyrrolidin-3-yloxy) ethyl-1-one (60 mg), which would he directly used in the next step.

LC-MS (m/z): 409 (M+1).

EXAMPLE 29

Preparation of 1-4-(1-hydroxy-2-(5H-imidazo[5,1-a]
isoindol-5-yl)ethyl)piperidin-1-yl)-2-(pyrrolidine-3-
yloxy) ethyl-1-one

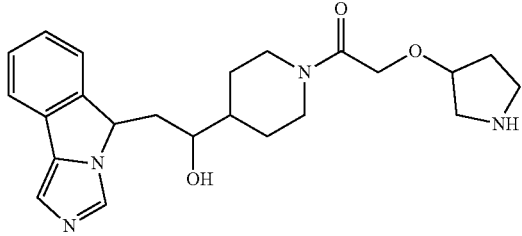 [SMILES: O=C(COC1CCNC1)N1CCC(C(O)CC2c3ccccc3-c3cncn32)CC1]

White solid 1(4-(1-hydroxy-2-(5H-imidazo[5,1-a]isoindol-5-yl)ethyl)piperidin-1-yl)-2-(pyrrolidine-3-yloxy) ethyl-1-one (19 mg, the overall yield of the two steps was 39.2%) was prepared from 1-(4-(2-(5H-imidazo[5,1-a]isoindol-5-yl)acetyl)piperidin-1yl)-2-(pyrrolidin-3-yloxy)ethyl-1-one (60 mg, crude) according to the steps similar to those in Example 21.

¹H NMR (500 MHz, DMSO-d6) δ 7.94 and 7.90 (s, 1H), 7.60 (d, J=7.5 Hz, 1H), 7.57 and 7.49 (d, J=7.5 Hz, 1H), 7.38 (t, J=7.5 Hz, 7.27 (t, J=7.6 Hz, 7.14 and 7.12 (s, 1H), 5.43 and 5.39 (d, J=7.0 Hz, 1H), 5.02 (brs, 1H), 4.43-4.23 (m, 1H), 4.17-3.94 (m, 3H), 3.90-3.74 (m, 1H), 3.72-3.63 (m, 1H), 3.30-3.12 (m, 3H), 2.94-2.59 (m, 3H), 2.48-2.34 (m, 1H), 2.08-2.07 (m, 1H), 1.97-1.62 (m, 4H), 1.58-1.53 (m, 2H), 1.24-1.10 (m, 2H).

LC-MS (m/z): 411 (M+1)

EXAMPLE 30

Preparation of ethyl 2-((9H-purin-6-yl)oxy)acetate

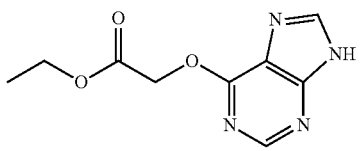 [SMILES: CCOC(=O)COc1ncnc2[nH]cnc12]

6-Chloro-9H-purine (3.08 g, 20.0 mmol) and DABCO (6.72 g, 60.0 mmol) were dissolved in DMSO (30 ml), stirred at 20° C. for 4 hours to react. Then the mixture was heated to 35° C. to react for 0.5 hours. The mixture was added into a reaction solution of 2-hydroxyethyl acetate (20.8 g, 200 mmol), NaH (6.40 g, 160 mmol) and DMSO (30 mL). The reaction solution was stirred at room temperature overnight and concentrated. The residue was diluted with 2-methyltetrahydrofuran (1 l) and washed with saturated brine (100 ml×3). The organic phase was dried over anhydrous sodium sulfate, filtered, and concentrated. The residue was purified by passing through column with EA/PE=1:1 to obtain a yellow solid compound ethyl 2-((9H-purin-6-yl)oxy)acetate (100 mg, 0.450 mmol, 2.25%).

LC-MS (m/z): 223 (M+1).

EXAMPLE 31

Preparation of 2-((9H-purin-6-yl)oxy) acetic acid

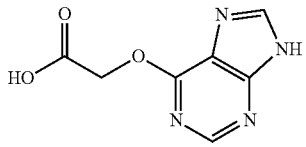 [SMILES: O=C(O)COc1ncnc2[nH]cnc12]

Ethyl 2-((9H-purin-6-yl)oxy acetate (100 mg, 0.450 mmol) and 2N sodium hydroxide solution (0.67 mL, 1.35 mmol) were added into methanol (5 ml), stirred at room temperature overnight and concentrated. The residue was adjusted to pH=5.0 with concentrated hydrochloric acid to obtain crude 2-((9H-purin-6-yl)oxy) acetic acid (200 mg), which would be directly used in the next step.

LC-MS (m/z): 195 (M+1).

EXAMPLE 32

Preparation of 1-(4-(2-(5H-imidazo[5,1-a]isoindol-
5-yl)acetyl)piperidin-1-yl)-2-((7H-purin-6-yloxy)
ethyl-1-one

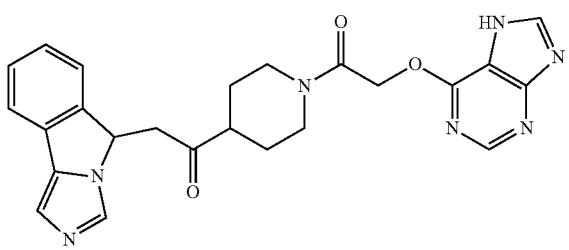 [SMILES: O=C(CC1c2ccccc2-c2cncn21)C1CCN(C(=O)COc2ncnc3nc[nH]c23)CC1]

1-(4-(2-(5H-Imidazo[5,1-a]isoindol-5-yl)acetyl)piperidin-1yl)-2-((7H-purin-6-yl)oxy)ethyl-1-one (90 mg, crude) was prepared from 2-((9H-purin-6-yl)oxy) acetic acid (36.7 mg, 0.189 mmol) and 2-(5H-imidazo[5,1-a]isoindol-5-yl)-1-(piperidin-4-yl)ethyl-1-one hydrochloride (50 mg, 0.158 mmol) according to the steps similar to those in Example 10.

LC-MS (m/z): 458 (M+1).

EXAMPLE 33

Preparation of 2-((7H-purin-6-yl)oxy)-1-(4-(1-hy-
droxy-2-(5H-imidazo[5,1-a]isoindol-5-yl)piperidin-
1yl) ethyl-1-one

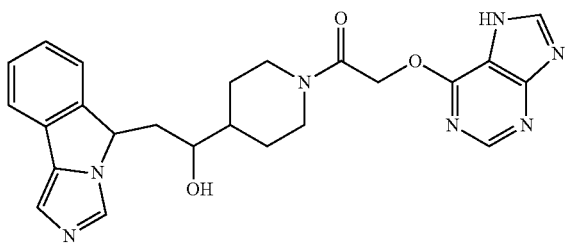 [SMILES: O=C(COc1ncnc2nc[nH]c12)N1CCC(C(O)CC2c3ccccc3-c3cncn32)CC1]

White solid 2-((7H-purin-6-yl)oxy)1-(4-hydroxy-2-(5H-imidazo[5,1-a]isoindol-5-yl)ethyl)piperidin-1-yl) ethyl-1-one (21 mg, the overall yield of the two steps was 29%) was prepared from 1-(4-(2-(5H-imidazo[5,1-a]isoindol-5-yl)acetyl)piperidin-1yl)-2-((7H-purin-6-yl)oxy)ethyl-1-one (90 mg, crude) according to the steps similar to those in Example 11.

$^1$H NMR (500 MHz, DMSO-d6) δ 13.44 (s, 1H), 8.42-8.37 (m, 2H), 8.01-7.91 (m, 1H), 7.68-7.47 (m, 2H), 7.39 (t, J=7.5 Hz, 1H), 7.28 (t, J=7.6 Hz, 1H), 7.15 and 7.12 (s, 1H), 5.49-5.37 (m, 1H), 5.37-5.23 (m, 2H), 5.17 and 5.06 (t, J=6.0 Hz, 1H), 4.38-4.24 (m, 1H), 3.94-3.80 (m, 1H), 3.78-3.66 (m, 1H), 3.01 (t, J=12.9 Hz, 1H), 2.25-2.05 (m, 1H), 1.95-1.50 (m, 4H), 1.44-1.31 (m, 1H), 1.21-1.08 (m, 1H) ppm.

LC-MS (m/z): 460 (M+1).

EXAMPLE 34

Preparation of ethyl 2-(benzo[d]oxazolin-2-yloxy)acetate

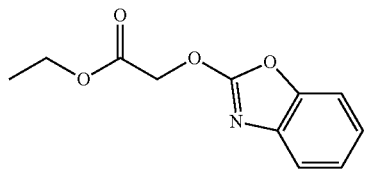 [SMILES: CCOC(=O)COc1nc2ccccc2o1]

At 0° C. NaH (1.00 g, 25.0 mmol) was added into THF (30 ml), and then 2-hydroxyethyl acetate (2.08 g, 20.0 mmol) was added. The reaction solution was stirred at 0° C. for 0.5 hours, then 2-chlorobenzo[d]oxazoline (1.53 g, 10.0 mmol) was added. The reaction solution was heated under reflux for 3 hours to react. After a portion of the solvent was recovered under reduced pressure, it was dilute with ethyl acetate EA (100 ml). The ethyl acetate phase was washed with water (50 ml) and saturated brine (50 ml). The organic phase was dried over anhydrous sodium sulfate, filtered and concentrated under reduced pressure. The residue was passed through column with eluent ethyl acetate/petroleum ether=1/20-1/10 to obtain an oily compound ethyl 2-(benzo[d]oxazolin-2-yloxy)acetate (1.11 g, 5.02 mmols, 50.2%).

LC-MS (m/z): 222 (M+1).

EXAMPLE 35

Preparation of 2-(benzo[d]oxazolin-2-yloxy)acetic acid

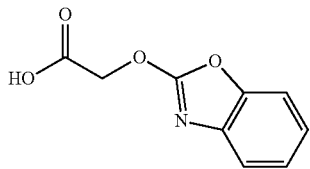 [SMILES: O=C(O)COc1nc2ccccc2o1]

A portion of ethyl 2-(benzo[d]oxazolin-2-yloxy)acetate (100 mg, 0.452 mmol) was taken and dissolved in sodium hydroxide solution (0.23 ml, 0.452 mmol, 2.0 M), methanol (5 ml) was added, stirred at room temperature overnight to react. The reaction solution was freeze-dried to obtain crude 2-(benzo[d]oxazolin-2-yloxy)acetic acid (200 mg, crude), which would be directly used in the next step.

LC-MS (m/z): 194 (M+1).

EXAMPLE 36

Preparation of 1-(4-(2-(5H-imidazo[5,1-a]isoindol-5-yl)acetyl)piperidin-1-yl)-2-(benzo[d]oxazolin-2-yloxy)ethyl-1-one

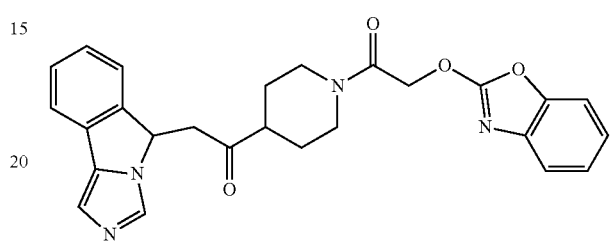

1-(4-(2-(5H-Imidazo[5,1-a]isoindol-5-yl)acetyl)piperidin-1yl)-2-(benzo[d]oxazolin-2-yloxy)ethyl-1-one (90 mg, crude) was prepared from 2-(benzo[d]oxazolin-2-yloxy)acetic acid (36.7 mg, 0.190 mmol) and 2-(5H-imidazo[5,1-a])isoindol-5-yl)-1-(piperidin-4-yl)ethyl-1-one hydrochloride (50 mg, 0.158 mmol) according to the steps similar to those in Example 10.

LC-MS (m/z): 457 (M+1).

EXAMPLE 37

Preparation of 2-(benzo[d]oxazolin-2-yloxy)-1-(4-(1-hydroxy-2-(5H-imidazo[5,1-a]isoindol-5-yl)ethyl)piperidin-1-yl)ethyl-1-one

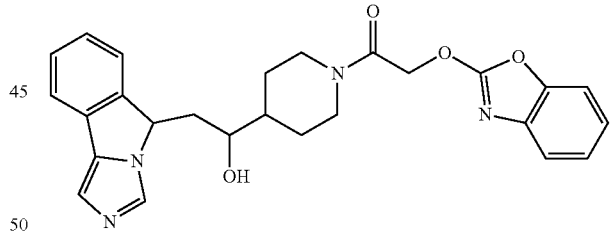

White solid 2-(benzo[d]oxazolin-2-yloxy)-1-(4-(1-hydroxy-2-(5H-imidazo[5,1-a]isoindol-5-yl)ethyl)piperidin-1-yl)ethyl-1one (14 mg, the overall yield of the two steps was 19.3%) was prepared from 1-(4-(2-(5H-imidazo[5,1-a]isoindol-5-yl)acetyl)piperidin-1yl)-2-(benzo[d]oxazolin-2-yloxy)ethyl-1-1-one (90 mg, crude) according to the steps similar to those in Example 11.

$^1$H NMR (500 MHz, DMSO-d$_6$) δ 7.96 and 7.93 (s, 1H), 7.62-7.50 (m, 3H), 7.45 (d, J=7.5 Hz, 1H), 7.39 (t, J=7.5 Hz, 1H), 7.32-7.19 (m, 3H), 7.15 and 7.13 (s, 1H), 5.48-5.37 (m, 1H), 5.36-5.24 (m, 2H), 5.16 and 5.05 (t, J=6.9 Hz, 1H), 4.37-4.27 (m, 1H), 3.81-3.66 (m, 2H), 2.99 (t, J=12.5 Hz, 1H), 2.54 (t, J=12.5 Hz, 1H), 2.26-1.74 (m, 3H), 1.68-1.50 (m, 2H), 1.42-1.28 (m, 1H), 1.19-1.11 (m, 1H) ppm.

LC-MS (m/z): 459 (M+1).

EXAMPLE 38

Preparation of 1-(4-(2-(5H-imidazo[5,1-a]isoindol-5-yl)acetyl)piperidin-1yl)-2-(3-chloro-4-fluorophenoxy)ethyl-1-1-one

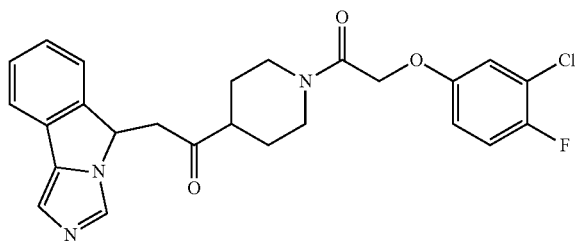 [SMILES: O=C(CC1c2ccccc2-c2cncn21)C1CCN(C(=O)COc2ccc(F)c(Cl)c2)CC1]

1-(4-(2-(5H-Imidazo[5,1-a]isoindol-5-yl)acetyl)piperidin-1-yl)-2-(3-chloro-4-fluorophenoxy)ethyl-1one (90 mg, crude) was prepared from 2-(3-chloro-4-fluorophenoxy)acetic acid (38.6 mg, 0.189 mmol) and 2-(5H-imidazo[5,1-a])isoindol-5-yl)-1-(piperidin-4-yl)ethyl-1-one hydrochloride (50 mg, 0.158 mmol) according to the steps similar to those in Example 20.

LC-MS (m/z): 468 (M+1).

EXAMPLE 39

Preparation of 2-(3-chloro-4-fluorophenoxy)-1-(4-(1-hydroxy-2-(5H-imidazo[5,1-a]isoindol-5-yl)ethyl)piperidin-1-yl)ethyl-1-one

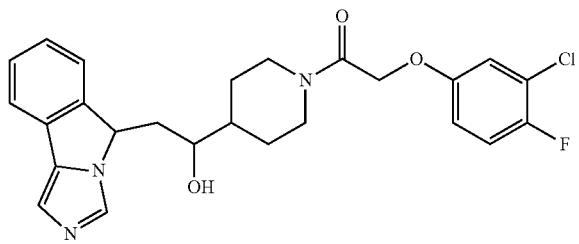 [SMILES: O=C(COc1ccc(F)c(Cl)c1)N1CCC(C(O)CC2c3ccccc3-c3cncn32)CC1]

White solid 2-(3-chloro-4-fluorophenoxy)-1-(4-(1-hydroxy-2-(5H-imidazo[5,1-a]isoindol-5-yl)ethyl)piperidin-1-yl)ethyl-1-one (10 mg, the overall yield of the two steps was 13.5%) was prepared from 1-(4-(2-(5H-imidazo[5,1-a]isoindol-5-yl)acetyl)piperidin-1yl)-2-(3-chloro-4-fluorophenoxy)ethyl-1-one (90 mg, crude) according to the steps similar to those in Example 21.

$^1$H NMR (500 MHz, DMSO-d6) δ 7.94 and 7.91 (s, 1H), 7.60 (d, J=7.6 Hz, 1H), 7.56 and 7.50 (d, J=7.5 Hz, 1H), 7.38 (t, J=7.4 Hz, 1H), 7.35-7.23 (m, 2H), 7.19-7.07 (m, 2H), 6.94-6.89 (m, 1H), 5.47-5.32 (m, 1H), 5.15-5.01 (m, 1H), 4.91-4.74 (m, 2H), 4.36 (t, J=16.6 Hz, 1H), 3.86-3.75 (m, 1H), 3.74-3.64 (m, 1H), 2.94 (t, J=12.4 Hz, 1H), 2.26-2.02 (m, 1H), 1.95-1.74 (m, 2H), 1.65-1.48 (m, 2H), 1.37-1.21 (m, 1H), 1.20-1.08 (m, 1H) ppm.

LC-MS (m/z): 470 (M+1).

EXAMPLE 40

Preparation of 1-(4-2-(5H-imidazo[5,1-a]isoindol-5-yl)acetyl)piperidin-1-yl)-2-(3-chlorophenoxy)ethyl-1-one

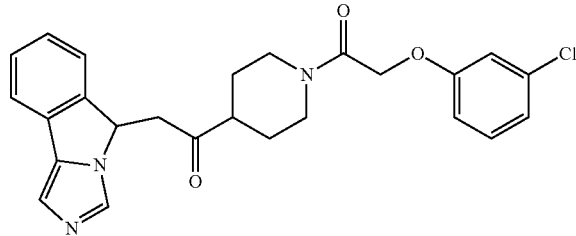 [SMILES: O=C(CC1c2ccccc2-c2cncn21)C1CCN(C(=O)COc2cccc(Cl)c2)CC1]

1-(4-(2-(5H-Imidazo[5,1-a]isoindol-5-yl)acetyl)piperidin-1yl)-2-(3-chlorophenoxy)ethyl-1-one (55 mg, 86%) was prepared from 2-(3-chlorophenoxy)acetic acid (32 mg, 0.17 mmol) and 2-(5H-imidazo[5,1-a])isoindol-5-yl)-1-(piperidin-4-yl)ethyl-1-one hydrochloride (40 mg, 0.142 mmol) according to the steps similar to those in Example 20.

LC-MS (m/z): 450 (M+1).

EXAMPLE 41

Preparation of 2-(3-chlorophenoxy)-1-(4 1-hydroxy-2-(5H-imidazo[5,1-a]isoindol-5-yl)ethyl)piperidin-1yl)ethyl-1-one

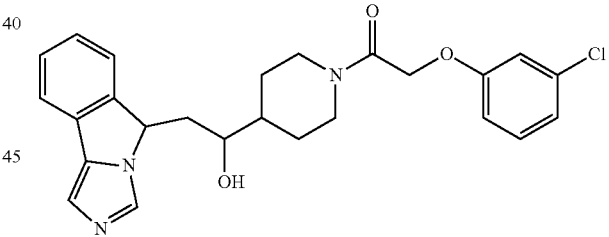

White solid 2-(3-chlorophenoxy)-1-(4-(1-hydroxy-2-(5H-imidazo[5,1-a]isoindol-5- yl)piperidin-1yl)ethyl-1-one (13 mg, 30%) was prepared from 1-(4-(2-(5H-imidazo[5,1-a]isoindol-5-yl)acetyl)piperidin-1yl)-2-(3-chlorophenoxy)ethyl-1one (50 mg, 0.11 mmol) according to the steps similar to those in Example 21.

$^1$H NMR (400 MHz, CDCl3) δ 7.808 (s, 1H) 7.543 (d, J=7.2 Hz, 1H), 7.319-7.418 (m, 2H), 7.238-7.275 (m, 1H), 7.164-7.205(m, 2H), 6.921-6.959 (m, 2H), 6.816 (d, J=8 Hz, 1H), 5.360-5.503 (m, 1H), 4.609-4.695 (m, 3H), 3.701-3.804 (m, 1H), 3.020 (t, J=12.8 Hz, 1H), 2.558 (t, J=12.8 Hz, 1H), 2.057-2.292 (m, 2H), 1.845-1.883 (m, 1H), 1.52-1.714 (m, 2H), 1.26-1.338 (m, 2H).

LC-MS (m/z): 452 (M+1).

EXAMPLE 42

Preparation of 1-(4-(2-(5H-imidazo[5,1-a]isoindol-5-yl)acetyl)piperidin-1-yl)-2-(4-fluorophenoxy)ethyl-1-one

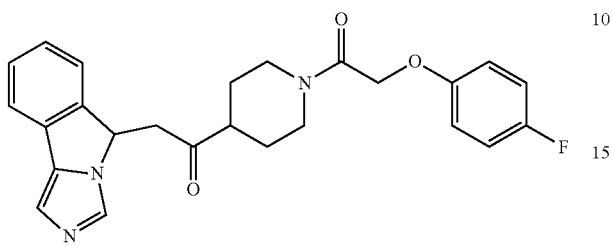

1-(4-(2-(5H-Imidazo[5,1-a]isoindol-5-yl)acetyl)piperidin-1yl)-2-(4-fluorophenoxy)ethyl-1-one (180 mg, crude) was prepared from 2-(4-fluorophenoxy)acetic acid (40.8 mg, 0.24 mmol) and 2-(5H-imidazo[5,1-a]isoindol-5-yl)-1-(piperidin-4-yl)ethyl-1-one hydrochloride (63.4 mg, 0.2 mmol) according to the steps similar to those in Example 20.

LC-MS (m/z): 434 (M+1).

EXAMPLE 43

Preparation of 2-(4-fluorophenoxy)-1-(4-(1-hydroxy-2-(5H-imidazo[5,1-a]isoindol-5-yl)ethyl)piperidin-1yl)ethyl-1-one

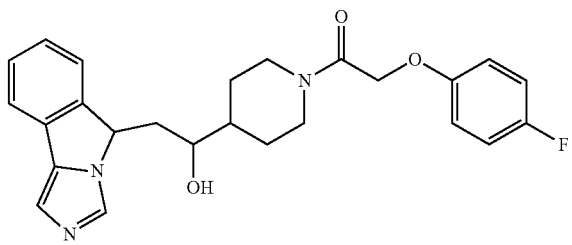 [SMILES: O=C(COc1ccc(F)cc1)N1CCC(C(O)CC2c3ccccc3-c3cncn32)CC1]

White solid 2-(4-fluorophenoxy)-1-(4-(1-hydroxy-2-(5H-imidazo[5,1-a]isoindol-5-yl)ethyl)piperidin-1-yl)ethyl-1-one (20 mg, the overall yield of the two steps was 23%) was prepared from 1-(4-(2-(5H-imidazo[5,1-a]isoindol-5-yl)acetyl)piperidin-1-yl)-2-(4-fluorophenoxy)ethyl-1-one (100 mg, crude) according to the steps similar to those in Example 21.

$^1$H NMR (500 MHz, DMSO-d6) δ 7.94 and 7.91 (s, 1H), 7.60 (d, J=7.5 Hz, 1H), 7.56 and 7.50 (d, J=7.5 Hz, 1H), 7.38 (t, J=7.5 Hz, 1H), 7.27 (t, J=7.4 Hz, 1H), 7.16-7.03 (m, 6.92 (dd, J=8.3, 4.2 Hz, 2H), 5.47-5.33 (m, 1H), 5.17-4.98 (m, 1H), 4.85-4.67 (m, 2H), 4.45-4.31 (m, 1H), 3.92-3.77 (m, 1H), 3.75-3.63 (m, 1H), 2.95 (t, J=13.0 Hz, 1H), 2.25-1.99 (m, 1H), 1.93-1.83 (m, 1H), 1.79 (d, J=12.9 Hz, 1H), 1.64-1.48 (m, 2H), 1.36-1.22 (m, 1H), 1.20-1.05 (m, 1H) ppm.

LC-MS (m/z): 436 (M+1).

EXAMPLE 44

Preparation of tert-butyl 4-(1-hydroxy-2-(5H-imidazo[5,1-a])isoindol-5-yl)ethyl)piperidine-1-formate

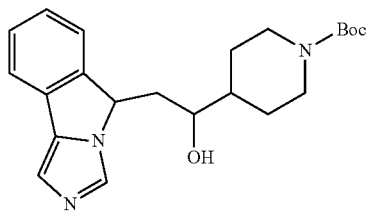 [SMILES: CC(C)(C)OC(=O)N1CCC(C(O)CC2c3ccccc3-c3cncn32)CC1]

tert-butyl 4-(1-Hydroxy-2-(5H-imidazo[5,1-a])isoindol-5-yl)ethyl)piperidine-1-formate was prepared from tert-butyl 4-(2-(5H-imidazo[5,1-a])isoindole-5-yl)acetyl)piperidine-1-formate according to the steps similar to those in Example 11.

LC-MS (m/z): 384 (M+1).

EXAMPLE 45

Preparation of 2-(5H-imidazo[5,1-a])isoindole-5-yl)-1-(piperidin-4-yl-ethyl-1-ol hydrochloride

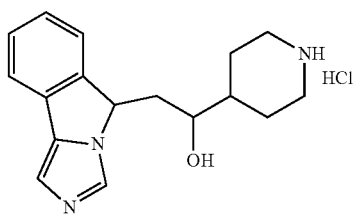 [SMILES: OC(CC1c2ccccc2-c2cncn21)C1CCNCC1 ; Cl]

tert-butyl 4-(1-Hydroxy-2-(5H-imidazo[5,1-a])isoindol-5-yl)ethyl)piperidine-1-formate (380 mg, 1 mmol) was dissolved in dichloromethane (10 ml), and then 4N HCl/1,4-dioxane (5 ml) was added. The mixture was reacted at 0° C. for 4 hours and concentrated under reduced pressure to obtain a crude yellow oily substance 2-(5H-imidazo[5,1-a]) isoindole-5-yl)-1-(piperidin-4-yl)-ethyl-1-ol hydrochloride (241 mg, 85%), which would be directly used in the next step.

LC-MS (m/z): 284 (M-HCl+1).

EXAMPLE 46

Preparation of 2-(3,4-dimethylphenoxy)-1-(4-(1-hydroxy-2-(5H-imidazo[5,1-a]isoindol-5-yl)ethyl)piperidin-1-yl)ethyl-1-one

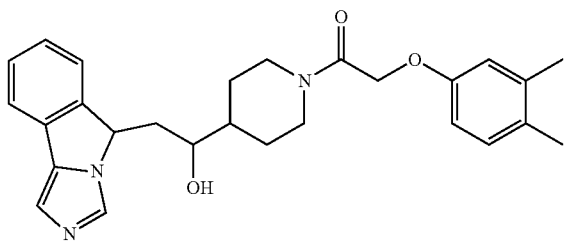 [SMILES: Cc1ccc(OCC(=O)N2CCC(C(O)CC3c4ccccc4-c4cncn43)CC2)cc1C]

Yellow solid 2-(3,4-dimethylphenoxy)-1-(4-(1-hydroxy-2-(5-H-imidazo[5,1-a]isoindol-5-yl)ethyl)piperidin-1-yl)ethyl-1-one (40 mg, 35.7%) was prepared from 2-(3,4-dimethylphenoxy)acetic acid (25 mg, 0.139 mmol) and 2-(5H-imidazo[5,1-a])isoindole-5-yl)-1-(piperidin-4-yl)-ethyl-1-ol hydrochloride (35.7 mg, 0.126 mmol) according to the steps similar to those in Example 20.

$^1$H NMR (500 MHz, DMSO-d6) δ 7.94 and 7.91 (s, 1H), 7.60 (d, J=7.6 Hz, 1H), 7.56 and 7.50 (d, J=7.5 Hz, 1H), 7.38 (t, J=7.4 Hz, 1H), 7.30-7.25 (m, 1H), 7.14 and 7.12 (s, 1H), 6.99 (d, J=8.2 Hz, 1H), 6.71 (s, 1H), 6.62 (d, J=8.2 Hz, 1H), 5.46-5.35 (m, 1H), 5.17-4.96 (m, 1H), 4.75-4.61 (m, 2H), 4.43-4.27 (m, 1H), 3.95-3.79 (m, 1H), 3.74-3.63 (m, 1H), 3.00-2.90 (m, 1H), 2.15 (s, 3H), 2.11 (s, 3H), 1.89-1.05 (m, 7H) ppm.

LC-MS (m/z): 446 (M+1).

EXAMPLE 47

Preparation of 1-(4-(2-(5H-imidazo[5,1-a]isoindol-5-yl)acetyl)piperidin-1yl)-2-(3-trifluoromethylphenoxy)ethyl-1-1-one

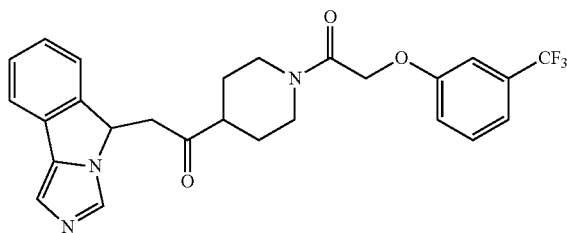 [SMILES: O=C(CC1c2ccccc2-c2cncn21)C1CCN(C(=O)COc2cccc(C(F)(F)F)c2)CC1]

1-(4-(2-(5H-Imidazo[5,1-a]isoindol-5-yl)acetyl)piperidin-1-1-yl)-2-(3-trifluoromethylphenoxy)ethyl-1one (90 mg, crude) was prepared from 2-(3-trifluoromethylphenoxy)acetic acid (41.6 mg, 0.189 mmol) and 2-(5H-imidazo[5,1-a])isoindol-5-yl)-1-(piperidin-4-yl)ethyl-1-one hydrochloride (50 mg, 0.158 mmol) according to the steps similar to those in Example 20.

LC-MS (m/z): 484 (M+1).

EXAMPLE 48

Preparation of 2-(3-trifluoromethylphenoxy)-1-(4-(1-hydroxy-2-(5H-imidazo[5,1-a]isoindol-5-yl)ethyl)piperidin-1-yl)ethyl-1-one

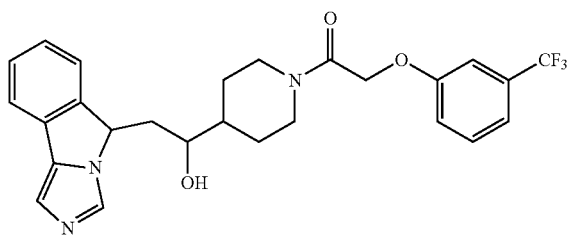 [SMILES: O=C(COc1cccc(C(F)(F)F)c1)N1CCC(C(O)CC2c3ccccc3-c3cncn32)CC1]

White solid 2-(3-trifluoromethylphenoxy)-1-(4-(1-hydroxy-2-(5H-imidazo[5,1-a]isoindol-5-yl)ethyl)piperidin-1-yl)ethyl-1-one (10 mg, the overall yield of the two steps was 15%) was prepared from 1-(4-(2-(5H-imidazo[5,1-a]isoindol-5-yl)acetyl)piperidin-1yl)-2-(3-trifluoromethylphenoxy)ethyl-1-1-one (90 mg, crude) according to the steps similar to those in Example 21.

$^1$H NMR (500 MHz, DMSO-d6) δ 7.94 and 7.91 (s, 1H), 7.60 (d, J=7.6 Hz, 1H), 7.58-7.47 (m, 2H), 7.38 (t, J=7.5 Hz, 1H), 7.30-7.25 (m, 2H), 7.21 (d, J=7.6 Hz, 2H), 7.14 and 7.12 (s, 1H), 5.47-5.34 (m, 1H), 5.17-5.00 (m, 1H), 4.99-4.85 (m, 2H), 4.42-4.31 (m, 1H), 3.92-3.78 (m, 1H), 3.75-3.64 (m, 1H), 2.96 (t, J=12.8 Hz, 1H), 2.24-2.02 (m, 1H), 1.92-1.50 (m, 4H), 1.36-1.24 (m, 1H), 1.19-1.04 (m, 1H) ppm. LC-MS (m/z) 486 (M+1).

EXAMPLE 49

Preparation of 1-(4-(2-(5H-imidazo[5,1-a]isoindol-5-yl)acetyl)piperidin-1-yl)-2-(cyclohexyloxy)ethyl-1-one

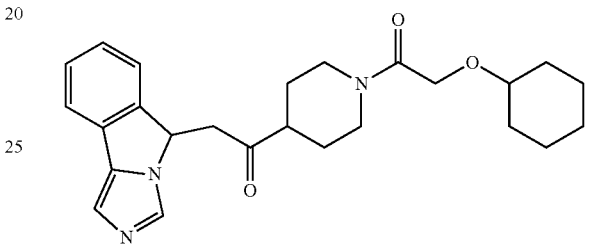

1-(4-(2-(5H-Imidazo[5,1-a]isoindol-5-yl)acetyl)piperidin-1yl)-2-(cyclohexyloxy)ethyl-1-one (80 mg, crude) was prepared from 2-(cyclohexyloxy)acetic acid (30 mg, 0.189 mmol) and 2-(5H-imidazo[5,1-a])isoindol-5-yl)-1-(piperidin-4-yl)ethyl-1one hydrochloride (50 mg, 0.158 mmol) according to the steps similar to those in Example 20.

LC-MS (m/z): 422 (M+1).

EXAMPLE 50

Preparation of 2-(cyclohexyloxy)-1-(4-(1-hydroxy-2-(5H-imidazo[5,1-a]isoindol-5-yl)ethyl)piperidin-1-yl)ethyl-1-one

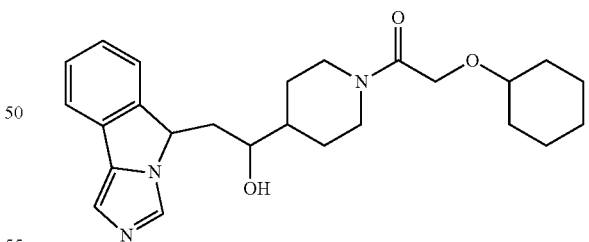

White solid 2-(cyclohexyloxy)-1-(4-(1-hydroxy-2-(5 H-imidazo[5,1-a]isoindol-5-yl)ethyl)piperidin-1-yl)ethyl-1-one (10 mg, the overall yield of the two steps was 15%) was prepared from 1-(4-(2-(5H-imidazo[5,1-a]isoindol-5-yl)acetyl)piperidin-1yl)-2-(cyclohexyloxy)ethyl-1-one (80 mg, crude) according to the steps similar to those in Example 2.

$^1$H NMR (500 MHz, DMSO-d6) δ 7.93 and 7.90 (s, 1H), 7.60 (d, J=7.5 Hz, 1H), 7.56 and 7.50 (d, J=7.5 Hz, 1H), 7.38 (t, J=7.5 Hz, 1H), 7.27 (t, J=7.5 Hz, 1H), 7.14 and 7.11 (s, 1H), 5.47-5.33 (m, 1H), 5.11 and 5.00 (t, J=5.0 Hz, 1H), 4.36 (t, J=13.9 Hz, 1H), 4.14-4.00 (m, 2H), 3.95-3.80 (m, 1H), 3.67 (t, J=9.9 Hz, 1H), 3.30-3.20 (m, 1H), 2.88 (t, J=12.8 Hz, 1H), 2.47-2.39 (m, 1H), 2.25-2.01 (m, 1H), 1.93-1.71 (m, 4H), 1.63 (s, 2H), 1.59-1.48 (m, 2H), 1.48-1.39 (m, 1H), 1.27-1.07 (m, 7H) ppm.

LC-MS (m/z): 424 (M+1).

EXAMPLE 51

Preparation of 1-(dibenzo[b,d]furan-2-yl)ethyl-1-one

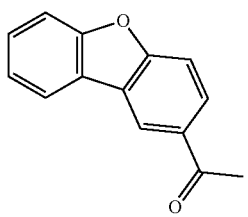 [SMILES: CC(=O)c1ccc2oc3ccccc3c2c1]

Dibenzo[b,d]furan (5.0 g, 29 mmol) was dissolved in chloroform (50 ml) and a solution of aluminum chloride AlCl$_3$ (4.8 g, 35.6 mmol) and acetyl chloride (2.8 g, 35.6 mmol) in chloroform (50 ml) was added. The reaction solution was stirred at room temperature for 45 minutes to react, and poured into a solution of iced water (100 ml) and 1N HCl (50 ml). The aqueous phase was extracted with chloroform (2×30 ml). The organic phases were combined. Dried over anhydrous sodium sulfate and concentrated under vacuum. The residue was purified by passing through column with eluent petroleum ether/ethyl acetate=20:1 to obtain a white solid 1-(dibenzo[b,d]furan-2-yl)ethyl-1-one (5.2 g, 90%), which would be directly used in the next step.

LC-MS (m/z): 211 (M+1).

EXAMPLE 52

Preparation of dibenzo[b,d]furan-2-acetate

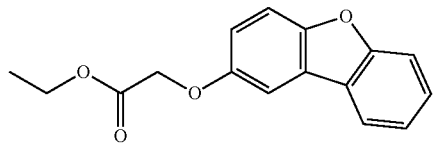 [SMILES: CCOC(=O)COc1ccc2oc3ccccc3c2c1]

1-(Dibenzo[b,d]furan-2-yl)ethyl-1one (5.2 g, 24.8 mmol) was dissolved in dichloromethane (150 ml). The mixture was cooled to 0° C., and trifluoroacetate (8.5 g, 75 mmol) and mCPBA (6.25 g, 28 mmol) were added. The reaction solution was stirred at room temperature for 3 days to react, quenched with ferrous sulfate, washed with water. The organic phase was dried over anhydrous sodium sulfate and concentrated under reduced pressure to obtain crude acetate dibenzo[b,d]furan-2-ester.

LC-MS (m/z): 227 (M+1).

EXAMPLE 53

Preparation of 2-hydroxydibenzo[b,d]furan

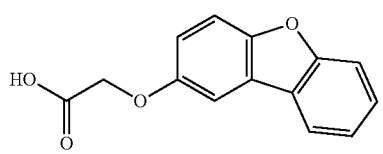 [SMILES: O=C(O)COc1ccc2oc3ccccc3c2c1]

Crude dibenzo[b,d]furan-2-acetate was dissolved in methanol (100 ml), and sodium methoxide (4 g, 75 mmol) was added, and then the mixture was stirred at room temperature for 20 minutes to react. The reaction solution was quenched with 2N HCl (50 ml). The organic solvent was recovered under reduced pressure, and the residue was diluted with water, extracted with chloroform (2×50 ml). The organic phases were combined, dried over anhydrous sodium sulfate, filtered, concentrated under reduced pressure, the residue was purified by passing through column with eluent petroleum ether/ethyl acetate=10/1 to obtain a grayish yellow solid 2-hydroxydibenzo[b,d]furan (3.6 g, 78%).

LC-MS (m/z): 185 (M+1).

EXAMPLE 54

Preparation of ethyl 2-(dibenzo[b,d]furan-2-yloxy)acetate

2-Hydroxydibenzo[b,d]furan (1.84 g, 10 mmol), ethyl bromoacetate (2 g, 12 mmol) and K$_2$CO$_3$ (2.726 g, 20 mmol) were dissolved in acetonitrile (50 ml), stirred at room temperature overnight. The reaction solution was filtered, the filtrate was concentrated, and the residue was passed through column with ethyl acetate/petroleum ether=1/10 to obtain ethyl 2-(dibenzo[b,d]furan-2-yloxy)acetate (2.5 g, 92%), which would be directly used in the next step.

LC-MS (m/z): 271 (M+1).

EXAMPLE 55

Preparation of 2-(dibenzo[b,d]furan-2-yloxy)acetic acid

Ethyl 2-(dibenzo[b,d]furan-2-yloxy)acetate (2.5 g, 9.3 mmol) was dissolved in a mixture of methanol (30 ml) and THF (30 ml), and sodium hydroxide solution was added (30 ml, 2N, 60 mmol). The reaction solution was stirred at room temperature overnight. The reaction was terminated, the organic phase was separated, and water (50 ml) was added into the residue. The pH was adjusted to 2 to 3 with 1N hydrochloric acid, a solid was precipitated, filtered, and the filter cake was washed with water (50 ml), dried to obtain a white solid 2-(dibenzo[b,d]furan-2-yloxy)acetic acid (2 g, 89%), which would be directly used in the next step.

LC-MS (m/z): 243 (M+1).

EXAMPLE 56

Preparation of 1-(4-(2-(5H-imidazo[5,1-a]isoindol-5-yl)acetyl)piperidin-1-yl)-2-(dibenzo[b,d]furan-2-yloxy)ethyl-1-one

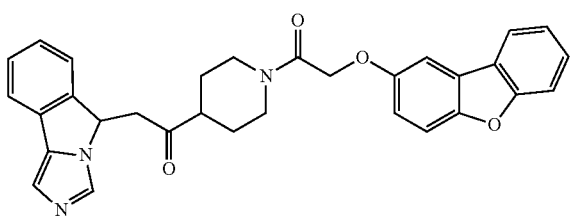 [SMILES: O=C(CC1c2ccccc2-c2cncn21)C1CCN(C(=O)COc2ccc3oc4ccccc4c3c2)CC1]

1-(4-(2-(5H-Imidazo[5,1-a]isoindol-5-yl)acetyl)piperidin-1yl)-2-(dibenzo[b,d]furan-2-yloxy)ethyl-1one (90 mg, crude) was prepared from 2-(dibenzo[b,d]furan-2-yloxy) acetic acid (46 mg, 0.189 mmol) and 2-(5H-imidazo[5,1-a]) isoindol-5-yl)-1-(piperidin-4-yl)ethyl-1 -one hydrochloride (50 mg, 0.158 mmol) according to the steps similar to those in Example 20.

LC-MS (m/z): 506 (M+1).

EXAMPLE 57

Preparation of 2-(dibenzo[b,d]furan-2-yloxy)-1-(4-(1-hydroxy-2-(5H-imidazo[5,1-a]isoindol-5-yl)ethyl)piperidin-1-yl)ethyl-1-one

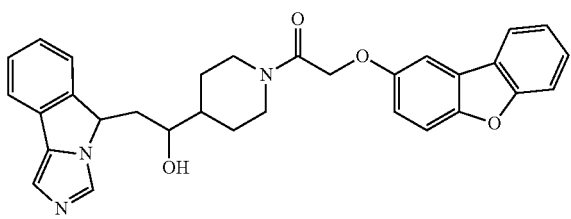 [SMILES: O=C(COc1ccc2oc3ccccc3c2c1)N1CCC(C(O)CC2c3ccccc3-c3cncn32)CC1]

2-(Dibenzo[b,d]furan-2-yloxy)-1-(4-(1-hydroxy-2-(5H-imidazo[5,1-a]isoindol-5-yl)ethyl)piperidin-1yl)ethyl-1-one (36 mg, the overall yield of the two steps was 45%) was prepared from 1-(4-(2-(5H-imidazo[5,1-a]isoindol-5-yl)acetyl)piperidin-1-yl)-2-(dibenzo[b,d]furan-2-yloxy)ethyl-1-one (90 mg, crude) according to the steps similar to those in Example 21.

$^1$H NMR (500 MHz, DMSO-d6) δ 8.09 (d, J=7.0 Hz, 1H), 7.96 and 7.92 (s, 1H), 7.69-7.66 (m, 2H), 7.63-7.49 (m, 4H), 7.38 (t, J=6.5 Hz, 2H), 7.27 (t, J=7.5 Hz, 1H), 7.14-7.10 (m, 2H), 5.41-5.39 (m, 1H), 5.17 and 5.06 (t, J=5.5 Hz, 1H), 4.93-4.85 (m, 2H), 4.41 (t, J=14.5 Hz, 1H), 3.93 (t, J=16.3 Hz, 1H), 3.72-3.71 (m, 1H), 3.01 (t, J 12.8 Hz, 1H), 2.55-2.52 (m, 1H), 2.11-2.05 (m, 1H), 1.91-1.58 (m, 4H), 1.38-1.33 (m, 1H), 1.23-1.13 (m, 1H) ppm.

LC-MS (m/z): 508 (M+1).

EXAMPLE 58

Preparation of 1-(4-(2-(5H-imidazo[5,1-a]isoindol-5-yl)acetyl)piperidin-1yl)-2-(1 ethyl(phenyl)amino)ethyl-1-one

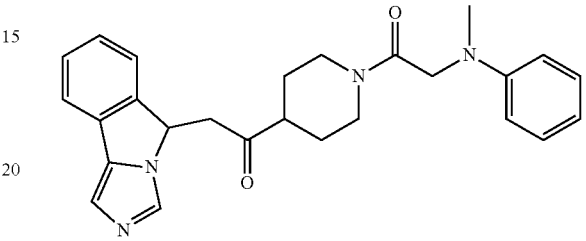

2-(5H-Imidazo[5,1-a])isoindol-5-yl)-1-(piperidin-4-yl) ethyl-1-one hydrochloride (500 mg, 1.58 mmol), N-methyl-N-phenylglycine (420 mg, 2.07 mmol) and DIPEA (0.9 ml, 4.0 mmol) was dissolved in DMF (25 ml). HOBT (250 mg, 1.85 mmol) and EDCI (500 mg, 2.62 mmol) were added. The reaction was allowed to react at room temperature overnight. The reaction solution was poured into 300 ml of water, and was adjusted to a pH of 8 to 10. A solid was precipitated, filtered to obtain a crude product. It was purified by passing through column with DCM/MeOH=20/1 to obtain 1-(4-(2-(5H-imidazo[5,1-a]isoindol-5-yl)acetyl)piperidin-1-yl)-2-(methyl(phenyl)amino)ethyl-1-one (390 mg, the yield was 57.7%).

LC-MS (m/z): 429 (M+1).

EXAMPLE 59

Preparation of 1-(4-(1-hydroxy-2-(5H-imidazo[5,1-a]isoindol-5-yl)ethyl)piperidin-1-yl)-2-methyl(phenyl)amino)ethyl-1-one

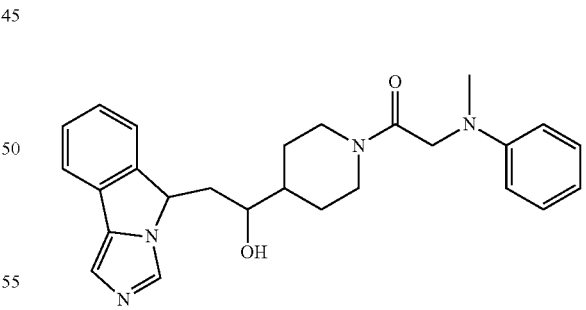

1-(4-(1-Hydroxy-2-(5H-imidazo[5,1-a]isoindol-5-yl) ethyl)piperidin-1-yl)-2-(methyl(phenyl)amino)ethyl-1-one (245 mg, 63%) was prepared from 1-(4-(2-(5H-imidazo[5,1-a]isoindol-5-yl)acetyl)piperidin-1yl)-2-(methyl(phenyl) amino)ethyl-1-one (390 mg, 0.91 mmol) according to the steps similar to those in Example 7.

$^1$H NMR (400 MHz, DMSO-d$_6$) δ 7.97 (s, 0.8H), 7.94 (s, 0.2H), 7.63~7.51 (m, 2H), 7.41 (t, J=7.5 Hz, 1H), 7.30 (t, J=7.5 Hz, 1H), 7.17-7.11 (m, 3H), 6.62-6.58 (m, 3H), 5.15 (d, J=5.4 Hz, 0.16H), 5.04 (d, J=5.4 Hz, 0.84H), 4.37 (t,

J=13.0 Hz, 1H), 4.23 (s, 2H), 3.92 (t, J=14.3 Hz, 1H), 3.73-3.72 (m, 1H), 3.00-2.93 (m, 4H), 2.47-2.44 (m, 1H), 2.22~2.06 (m, 1H), 2.01-1.87 (m, 1H), 1.82~1.79 (m, 1H), 1.63~1.56 (m, 2H), 1.31~1.27 (m, 1H), 1.20-1.10 (m, 1H).

LC-MS (m/z): 431 (M+1).

EXAMPLE 60

Preparation of ethyl N-(3-chlorophenyl)-N-methylglycine

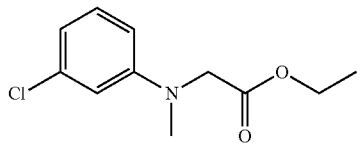

3-Chloro-N-methylaniline (300 mg, 2.13 mmol), ethyl 2-bromoacetate (426 mg, 2.55 mmol), diisopropylethylamine (550 mg, 4.26 mmol) and 10 ml of acetonitrile were added into a 20 ml microwave tube. The mixture was reacted under microwave at 100° C. for 2 hours. The reaction was terminated, cooled to room temperature, and concentrated. The residue was passed through column (the developing solvent was petroleum ether:ethyl acetate=10:1) to obtain a compound ethyl N-(3-chlorophenyl)-N-methylglycine (460 mg, the yield was 95%).

LC-MS (m/z): 228 (M+1).

EXAMPLE 61

Preparation of N-(3-chlorophenyl)-N-methylglycine

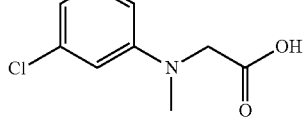

ethyl N-(3-chlorophenyl)-N-methylglycine (460 mg, 2.02 mmol) was dissolved in methanol (10 ml) and tetrahydrofuran (10 ml), and 10 ml of lithium hydroxide (1 mol/l) was added. The reaction was allowed to react at room temperature for 3 hours and then terminated. The pH of the reaction solution was adjusted to 6 with 1 mol/l hydrochloric acid. It was extracted 3 times with ethyl acetate. The combined organic layers were washed with saturated brine for 3 times, dried over anhydrous sodium sulfate, filtered and subjected to spin drying. The residue was passed through column (the developing solvent was petroleum ether:ethyl acetate=2:1) to obtain a white solid N-(3-chlorophenyl)-N-methylglycine (260 mg, 65%).

LC-MS (m/z): 200 (M+1).

EXAMPLE 62

Preparation of 1-4-2-5H-imidazo[5,1-a]isoindol-5-yl)acetyl)piperidin-1-yl)-2-((3-chlorophenyl)(methyl)amino)ethyl-1-one

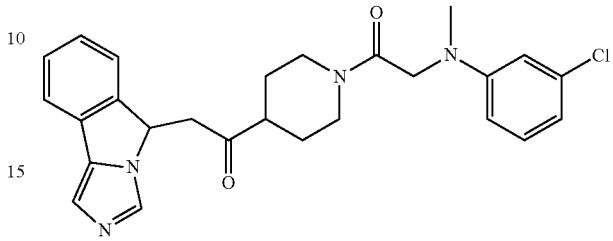

N-(3-Chlorophenyl)-N-methylglycine (100 mg, 0.5 mmol), 2-(5H-imidazo[5,1-a])isoindol-5-yl)-1-(piperidin-4-yl)ethyl-1-one hydrochloride (150 mg, 0.5 mmol), HATU (285 mg, 0.75 mmol), diisopropylethylamine (322 mg, 2.5 mmol) and dichloromethane (30 ml) were added to a 100 ml round-bottom flask. The mixture was stirred at room temperature overnight. The reaction was terminated. The reaction solution was washed with water twice, dried over anhydrous sodium sulfate, filtered and subjected to spin drying. The residue was passed through column (the developing solvent was dichloromethane:methanol=20:1) to obtain a white solid 1-(4-(2-(5H-imidazo[5,1-a]isoindol-5-yl)acetyl)piperidin-1-yl)-2-((3-chlorophenyl)(methyl)amino)ethyl-1-one (100 mg, 43%).

LC-MS (m/z): 463 (M+1).

EXAMPLE 63

Preparation of 2-((3-chlorophenyl)(methyl)amino)-1-(4-(2-(5H-imidazo[5,1-a]isoindol-5-yl)ethyl)piperidin-1yl)-ethyl-1-one

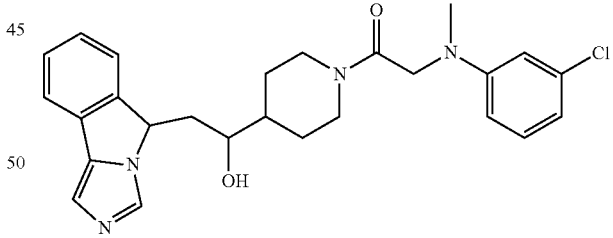

1-(4-(2-(5H-Imidazo[5,1-a]isoindol-5-yl)acetyl)piperidin-1yl)-2-((3-chlorophenyl)(methyl)amino)ethyl-1one (100 mg, 0.02 mmol) was dissolved in 10 ml of methanol and cooled to 0° C. Sodium borohydride (38 mg, 1 mmol) was added. The reaction was carried out at 0° C. for 2 hours and was then terminated. The reaction solution was poured into 100 ml of water, extracted with ethyl acetate for 3 times. The combined organic layers were washed with saturated aqueous sodium chloride solution for 2 times, dried over anhydrous sodium sulfate, filtered and subjected to spin drying. The residue was passed through column (the developing solvent was dichloromethane:methanol=15:1) to obtain a white solid 2-((3-chlorophenyl)(methyl)amino)-

1-(4-(2-(5H-imidazo[5,1-a]isoindol-5-yl)ethyl)piperidin-1yl)-ethyl-1one (40 mg, 40%).

¹H NMR (400 MHz, MeOD) δ 8.028(s, 0.8H) 7.973(s, 0.2H), 7.628(d, J=7.6 Hz, 1H), 7.765(d, J=7.6 Hz, 0.8H), 7.487(d, J=7.6 Hz, 0.2H), 7.425(t, J=7.6 Hz, 1H), 7.318-7.363(m, 1H), 7.168(s, 1H), 7.108(t, J=9.6 Hz, 1H), 6.631(s, 1H), 6.589(t, J=9.6 Hz, 1H), 5.453-5.546(m, 1H), 4.536(t, J=15.2 Hz, 1H), 4.203-4.336(m, 2H), 4.002(t, J=15.2 Hz, 1H), 3.725-3.824(m, 1H), 3.094(t, J=12.4 Hz, 1H), 3.012(s, 3H), 2.621(t, J=12.4 Hz, 1H), 2.069-2.362(m, 2H), 1.933(t, J=12 Hz, 1H), 1.622-1.742(m, 2H), 1.218-1.447(m, 2H).

LC-MS (m/z): 465 (M+1).

EXAMPLE 64

Preparation of ethyl (3-chloro-4-fluorophenyl)glycine

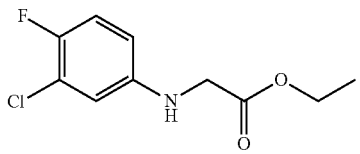

3-Chloro-4-fluoroaniline (1000 mg, 6.89mmol), ethyl 2-bromoacetate (1720 mg, 10.3 mmol), diisopropylethylamine (2660 mg, 20.6 mmol) and 20 ml of acetonitrile were added into a 20 ml microwave tube. The mixture was reacted under microwave at 100° C. for 2 hours. The reaction was terminated, cooled to room temperature, and concentrated. The residue was passed through column (the developing solvent was petroleum ether:ethyl acetate=10:1) to obtain a yellow oily substance ethyl (3-chloro-4-fluorophenyl)glycine (820 mg, 51%).

LC-MS (m/z): 232 (M+1).

EXAMPLE 65

Preparation of ethyl N-(3-chloro-4-fluorophenyl)-N-methylglycine

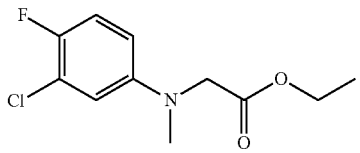 [SMILES: CCOC(=O)CN(C)c1ccc(F)c(Cl)c1]

Ethyl (3-chloro-4-fluorophenyl)glycine (400 mg, 1.73 mmol) was dissolved in DMF (10 ml), and cesium carbonate (1680 mg, 5.19 mmol) and methyl iodide (1220 mg, 8.65 mmol) were added thereto. The mixture was stirred at 50° C. for 16 hours. The reaction solution was cooled to room temperature, diluted with ethyl acetate (30 ml), and washed with saturated brine (30 ml) for 4 times. The organic phase was dried over anhydrous sodium sulfate and subjected to spin drying. The residue was passed through column (the developing solvent was petroleum ether:ethyl acetate=10:1) to obtain a light yellow solid ethyl N-(3-chloro-4-fluorophenyl)-N-methylglycine (360 mg, 85%).

LC-MS (m/z): 246 (M+1).

EXAMPLE 66

Preparation of N-(3-chloro-4-fluorophenyl)-N-methylglycine

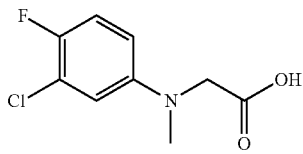

Greyish white solid N-(3-chloro-4-fluorophenyl)-N-methylglycine (170 mg, 95%) was prepared from ethyl N-(3-chloro-4-fluorophenyl)-N-methylglycine (200 mg, 0.816 mmol) according to the steps similar to those in Example 61.

LC-MS (m/z): 218 (M+1).

EXAMPLE 67

Preparation of 1-(4-(2-(5H-imidazo[5,1-a]isoindol-5-yl)acetyl)piperidin-1-yl)-2-((3-chloro-4-fluorophenyl)(methyl)amino)ethyl-1one

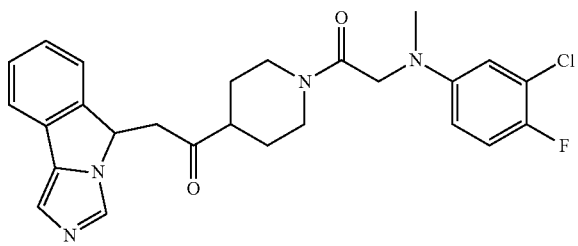 [SMILES: CN(CC(=O)N1CCC(C(=O)CC2c3ccccc3-c3cncn32)CC1)c1ccc(F)c(Cl)c1]

Yellow oily 1-(4-(2-(5H-imidazo[5,1-a]isoindol-5-yl)acetyl)piperidin-1yl)-2-((3-chloro-4-fluorophenyl)(methyl)amino)ethyl-1-one (130 mg, 51%) was prepared from N-(3-chloro-4-fluorophenyl)-N-methylglycine (150 mg, 0.69 mmol) and 2-(5H-imidazo[5,1-a])isoindol-5-yl)-1-(piperidin-4-yl)ethyl-1one hydrochloride (150 mg, 0.53 mmol) according to the steps similar to those in Example 62.

LC-MS (m/z): 481 (M+1).

EXAMPLE 68

Preparation of 2-((3-chloro-4-fluorophenyl)(methyl)amino)-1-(4-(1-hydroxy-2-(5H-imidazo[5,1-a]isoindol-5-yl) ethyl)piperidin-1-yl)ethyl-1-one

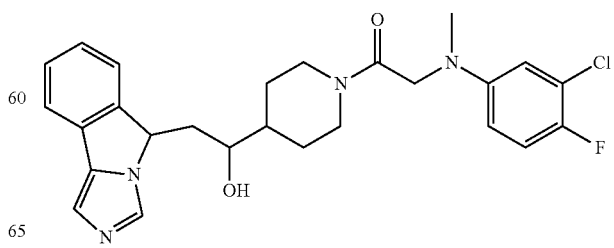

White solid 2-((3-chloro-4-fluorophenyl)(methyl)amino)-1-(4-(1-hydroxy-2-(5H-imidazo[5,1-a]isoindol-5-yl) ethyl)piperidin-1yl)ethyl-1-one (80 mg, 61%) was prepared from 1-(4-(2-(5H-imidazo[5,1-a]isoindol-5-yl)acetyl)piperidin-1yl)-2-((3-chloro-4-fluorophenyl)(methyl)amino)ethyl-1-one (130 mg, 0.27 mmol) according to the steps similar to those in Example 63.

¹H NMR (400 MHz, CD3OD) δ 8.10 (s, 1H), 7.66~7.49 (m, 2H), 7.43 (t, J=8 Hz, 1H), 7.36 (t, J=6 Hz, 1H), 7.22 (s, 1H), 7.01 (t, J=8 Hz, 1H), 6.69~6.67 (m, 1H), 6.58~6.56 (m, 1H), 5.50~5.47 (m, 1H), 4.56~4.49 (t, J=14 Hz, 1H), 4.29~4.17 (m, 2H), 3.98 (t, J=16 Hz, 1H), 3.82~3.78 (m, 1H), 3.11~3.04 (m, 1H), 2.98 (s, 3H), 2.61 (t, J=14 Hz, 1H), 2.18~2.12 (m, 2H), 1.95~1.92 (m, 1H), 1.70~1.65 (m, 2H), 1.33~1.22 (m, 2H).

LC-MS (m/z): 483 (M+1).

EXAMPLE 69

Preparation of ethyl N-(4-fluorophenyl)-N-methylglycine

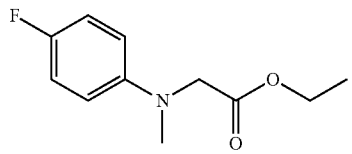

Yellow oily ethyl N-(4-fluorophenyl)-N-methylglycine (0.8 g, 95%) was prepared from 4-fluoro-N-methylaniline (500 mg, 4 mmol) and ethyl 2-bromoacetate (1.33 g, 8 mmol) according to the steps similar to those in Example 60.

LC-MS (m/z): 212 (M+1).

EXAMPLE 70

Preparation of N-(4-fluorophenyl)-N-methylglycine

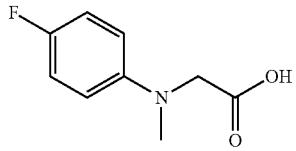

Yellow oily N-(4-fluorophenyl)-N-methylglycine (600 mg, 98%) was prepared from ethyl N-(4-fluorophenyl)-N-methylglycine (700 mg, 3.3 mmol) according to the steps similar to those in Example 61.

LC-MS (m/z): 184 (M+1).

EXAMPLE 71

Preparation of 1-(4-(2-(5H-imidazo[5,1-a]isoindol-5-yl)acetyl)piperidin-1-yl)-2-((4-fluorophenyl)(methyl)amino)ethyl-1-one

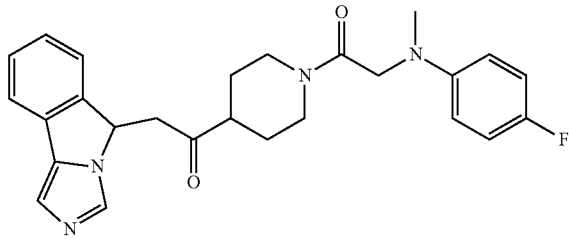 [SMILES: CN(CC(=O)N1CCC(C(=O)CC2c3ccccc3-c3cncn32)CC1)c1ccc(F)cc1]

Yellow oily 1-(4-(2-(5H-imidazo[5,1-a]isoindol-5-yl)acetyl)piperidin-1yl)-2-((4-fluorophenyl)(methyl)amino)ethyl-1-one (50 mg, 24%) was prepared from N-(4-fluorophenyl)-N-methylglycine (110 mg, 0.6 mmol) and 2-(5H-imidazo[5,1-a]isoindol-5-yl)-1-(piperidin-4-yl)ethyl-1-one hydrochloride (130 mg, 0.46 mmol) according to the steps similar to those in Example 62.

LC-MS (m/z): 447 (M+1).

EXAMPLE 72

Preparation of 2-((4-fluorophenyl)(methyl)amino)-1-(4-(1-hydroxy-2-(5H-imidazo[5,1-a]isoindol-5-yl)ethyl)piperidin-1-yl)ethyl-1-one

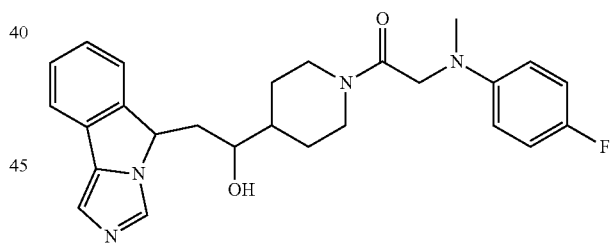

White solid 2-((4-fluorophenyl)(methyl)-1-(4-(1-hydroxy-2-(5H-imidazo[5,1-a]isoindol-5-yl)ethyl)piperidin-1yl)ethyl-1-one (35 mg, 70%) was prepared from 1-(4-(2-(5H-imidazo[5,1-a]isoindol-5-yl)acetyl)piperidin-1yl)-2-((4-fluorophenyl)(methyl)amino) ethyl-1-one (50 mg, 0.11 mmol) according to the steps similar to those in Example 63.

¹H NMR (400 MHz, CD3OD) δ 8.00 (s, 1H), 7.64~7.48 (m, 2H), 7.42 (t, J=6 Hz, 1H), 7.33 (t, J=8 Hz, 1H), 7.15 (s, 1H), 6.90 (t, J=8 Hz, 2H), 6.67~6.65 (m, 2H), 5.50~5.44 (m, 1H), 4.53 (t, J=14 Hz, 1H), 4.26~4.13 (m, 2H), 4.01 (t, J=16 Hz, 1H), 3.80~3.73 (m, 1H), 3.10~3.03 (m, 1H), 2.98 (s, 3H), 2.60 (t, J=14 Hz, 1H), 2.21~2.03 (m, 2H), 1.94~1.89 (m, 1H), 1.72~1.64 (m, 2H), 1.27~1.19 (m, 2H).

LC-MS (m/z): 449 (M+1).

EXAMPLE 73

Preparation of ethyl (3,4-dimethylphenyl)glycine

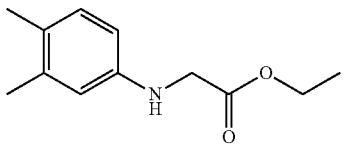

Ethyl(3,4-dimethylphenyl)glycine (320 mg, 38%) was prepared from 3,4-dimethylaniline (500 mg, 4.1 mmol) and ethyl 2-bromoacetate (897 mg, 5.4 mmol) according to the steps similar to those in Example 64.

LC-MS (m/z): 208 (M+1).

EXAMPLE 74

Preparation of ethyl N-(3,4-dimethylphenyl)-N-methylglycine

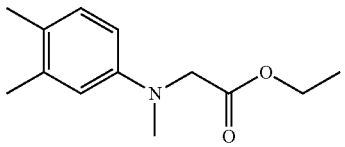 [SMILES: CCOC(=O)CN(C)c1ccc(C)c(C)c1]

White solid ethyl N-(3,4-diphenyl)-N-methylglycine (130 mg, 40%) was prepared from ethyl (3,4-dimethylphenyl)glycine (300 mg, 1.45 mmol) and methyl iodide (1.02 g, 7.25 mmol) according to the steps similar to those in Example 65.

LC-MS (m/z): 222 (M+1).

EXAMPLE 75

Preparation of N-(3,4-dimethylphenyl)-N-methylglycine

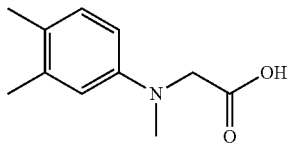

White solid N-(3,4-dimethylphenyl)-N-methylglycine (100 mg, 88%) was prepared from ethyl N-(3,4-dimethylphenyl)-N-methylglycine (130 mg, 0.59 mmol) according to the steps similar to those in Example 66.

LC-MS (m/z): 194 (M+1).

EXAMPLE 76

Preparation of 1-(4-(2-(5H-imidazo[5,1-a]isoindol-5-yl)acetyl)piperidin-1-yl)-2-((3,4-dimethylphenyl)(methyl)amino)ethyl-1one

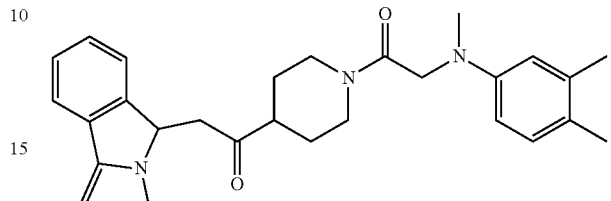

Yellow oily 1-(4-(2-(5H-imidazo[5,1-a]isoindol-5-yl)acetyl)piperidin-1-yl)-2-((3,4-dimethylphenyl)(methyl)amino)ethyl-1one (130 mg, 50%) was prepared from N-(3,4-dimethylphenyl)-N-methylglycine (100 mg, 0.65 mmol) and 2-(5H-imidazo[5,1-a])isoindol-5-yl)-1-(piperidin-4-yl)ethyl-1-one hydrochloride (160 mg, 0.5 mmol) according to the steps similar to those in Example 67.

LC-MS (m/z): 457 (M+1).

EXAMPLE 77

Preparation of 2-((3,4-dimethylphenyl)(methyl)amino)-1-(4-(1-hydroxy-2-(5H-imidazo[5,1-a]isoindol-5-yl)ethyl)piperidin-1-yl)ethyl)-1-one

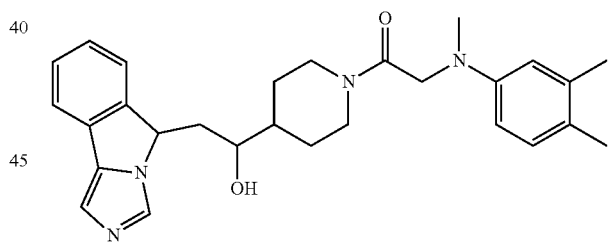

White solid 2-((3,4-dimethylphenyl)(methyl)amino)-1-(4-(1-hydroxy-2-(5H-imidazo[5,1-a]isoindol-5-yl)ethyl)piperidin-1-yl)ethyl-1-one (80 mg, 60%) was prepared from 1-(4-(2-(5H-imidazo[5,1-a]isoindol-5-yl)acetyl)piperidin-1-yl)-2-((3,4-dimethylphenyl)(methyl)amino)ethyl-1one (130 mg, 0.29 mmol) according to the steps similar to those in Example 68.

$^1$H NMR (400 MHz, CD3OD) δ 8.00 (s, 1H), 7.64~7.55 (m, 2H), 7.42 (t, J=6 Hz, 1H), 7.33 (t, J=8 Hz, 1H), 7.15 (s, 1H), 6.90 (d, J=4 Hz, 1H), 6.51 (s, 1H), 6.44 (d, J=4 Hz, 1H), 5.45~5.42 (m, 1H), 4.54 (t, J=14 Hz, 1H), 4.18~4.06 (m, 3H), 3.80~3.77 (m, 1H), 3.09~3.02 (m, 1H), 2.95 (s, 3H), 2.59 (t, J=12 Hz, 1H), 2.18~2.07 (m, 8H), 1.91~1.88 (m, 1H), 1.70~1.63 (m, 2H), 1.37~1.22 (m, 2H).

LC-MS (m/z): 459 (M+1).

EXAMPLE 78

Preparation of ethyl N-ethyl-N-phenylglycine

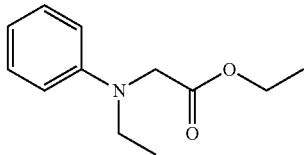

Ethyl N-ethyl-N-phenylglycine (3.2 g, 85%) was prepared from N-ethylaniline (2.0 g, 16.5 mmol) and ethyl 2-bromoacetate (4.11 g, 24.8 mmol) according to the steps similar to those in Example 60.

LC-MS (m/z): 208 (M+1).

EXAMPLE 79

Preparation of N-ethyl-N-phenylglycine

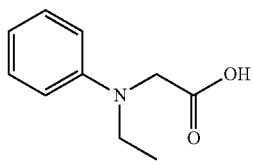

White solid N-ethyl-N-phenylglycine (90 mg, crude) was prepared from ethyl N-ethyl-N-phenylglycine (100 mg, 0.452 mmol) according to the steps similar to those in Example 61.

LC-MS (m/z): 180 (M+1).

EXAMPLE 80

Preparation of 1-(4-(2-(5H-imidazo[5,1-a]isoindol-5-yl)acetyl)piperidin-1yl)-2-(ethyl(phenyl)amino)ethyl-1-one

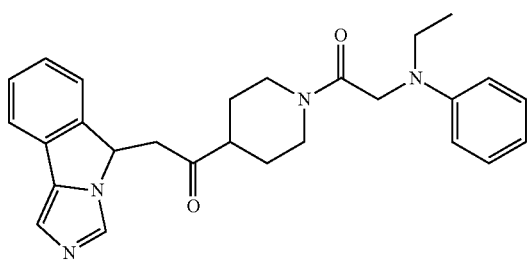 [SMILES: CCN(CC(=O)N1CCC(C(=O)CC2c3ccccc3-c3cncn32)CC1)c1ccccc1]

Brown solid 1-(4-(2-(5H-imidazo[5,1-a]isoindol-5-yl)acetyl)piperidin-1-yl)-2-(ethyl(phenyl)amino)ethyl-1-one (70 mg, crude) was prepared from N-ethyl-N-phenylglycine (79 mg, 0.442 mmol) and 2-(5H-imidazo[5,1-a]isoindol-5-yl)-1-(piperidin-4-yl)ethyl-1one hydrochloride (70 mg, 0.221 mmol) according to the steps similar to those in Example 62.

LC-MS (m/z): 443 (M+1).

EXAMPLE 81

Preparation of 2-(ethyl(phenyl)amino)-1-(4-(1-hydroxy-2-(5H-imidazo[5,1-a]isoindol-5-yl)ethyl)piperidin-1yl)ethyl-1-one

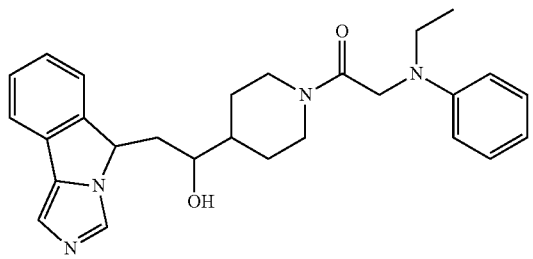 [SMILES: CCN(CC(=O)N1CCC(C(O)CC2c3ccccc3-c3cncn32)CC1)c1ccccc1]

White solid 2-(ethyl(phenyl)amino)-1-(4-(1-hydroxy-2-(5H-imidazo[5,1-a]isoindol-5-yl)ethyl)piperidin-1-yl)ethyl-1-one (15 mg, 21.3%) was prepared from 1-(4-(2-(5H-imidazo[5,1-a]isoindol-5-yl)acetyl)piperidin-1yl)-2-(ethyl(phenyl)amino)ethyl-1-one (70 mg, 0.158 mmol) according to the steps similar to those in Example 63.

$^1$H NMR (400 MHz, DMSO-d6) δ 7.95 (s, 1H), 7.61~7.57 (m, 2H), 7.39 (t, J=12 Hz, 1H), 7.29 (t, J=12 Hz, 1H), 7.15~7.08 (m, 3H), 6.56~6.52 (m, 3H), 5.41~5.38 (m, 1H), 5.02 (s, 1H), 4.41~4.36 (m, 1H), 4.13 (s, 2H), 3.98~3.90 (m, 1H), 371~3.70 (m, 1H), 3.38 (s, 1H), 2.96~2.93 (m, 1H), 2.47~2.45 (m, 1H), 2.08~2.06 (m, 1H), 1.91~1.88 (m, 1H), 1.80~1.78 (m, 1H), 1.58~1.53 (m, 2H), 1.29~1.22 (m, 1H), 1.13~1.07 (m, 4H).

LC-MS (m/z): 445 (M+1).

EXAMPLE 82

Preparation of N-(tert-butoxycarbonyl)-N-phenylglycine

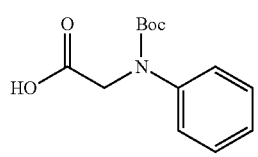 [SMILES: CC(C)(C)OC(=O)N(CC(=O)O)c1ccccc1]

Phenylglycine (1.51 g, 10 mmol), (Boc)2O (3.27 g, 15 mmol) and sodium carbonate (2.12 g, 20 mmol) were dissolved in methanol (50 ml) and water (20 mmol). Sodium carbonate (1.06 g, 10 mmol) was supplemented to make the pH between 9 and 10. The reaction was allowed to react at room temperature overnight. After the reaction was completed, the reaction solution was diluted with water (40 ml), and adjusted to a pH of 1 to 2 with hydrochloric acid. It was extracted with dichloromethane (40 ml*2), washed with water (20ml*2). The organic phase was concentrated under reduced pressure to obtain a tan liquid N-(tert-butoxycarbonyl)-N-phenylglycine (2.49 g, the yield was 98%).

LC-MS (m/z): 252 (M+1).

EXAMPLE 83

Preparation of tert-butyl (2-(4-(2-(5H-imidazo[5,1-a]isoindol-5-yl)acetyl)piperidin-1-yl)-2-oxoethyl)(phenyl) formate

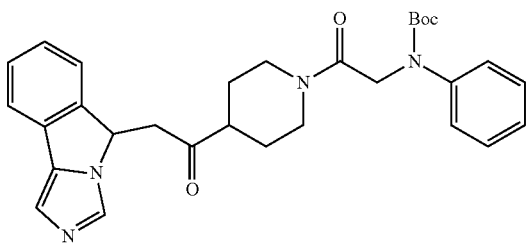 [SMILES: CC(C)(C)OC(=O)N(CC(=O)N1CCC(C(=O)CC2c3ccccc3-c3cncn32)CC1)c1ccccc1]

tert-butyl (2-(4-(2-(5H-Imidazo[5,1-a]isoindol-5-yl)acetyl)piperidin-1yl)-2-oxoethyl)(phenyl)formate (900 mg, 57%) was prepared from N-(tert-butoxycarbonyl)-N-phenylglycine (1.0 g, 4 mmol) and 2-(5H-imidazo[5,1-a]isoindol-5-yl)-1-(piperidin-4-yl)ethyl-1one hydrochloride (837 mg, 2.64 mmol) according to the steps similar to those in Example 58.

LC-MS (m/z): 515 (M+1).

EXAMPLE 84

Preparation of tert-butyl 2-(4-(1-hydroxy-2-(5H-imidazo[5,1-a]isoindol-5-yl)ethyl)piperidin-1-yl)-2-oxyethyl) (phenyl)formate

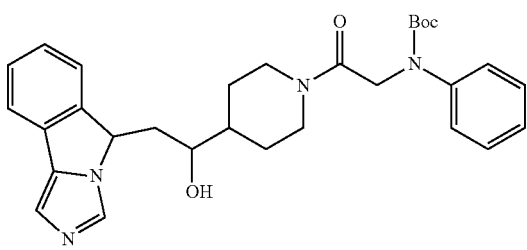 [SMILES: CC(C)(C)OC(=O)N(CC(=O)N1CCC(C(O)CC2c3ccccc3-c3cncn32)CC1)c1ccccc1]

tert-butyl (2-(4-(1-Hydroxy-2-(5H-imidazo[5,1-a]isoindol-5-yl)ethyl)piperidin-1-yl)-2-oxyethyl)(phenyl)formate (600 mg, 67%) was prepared from tert-butyl (2-(4-(2-(5H-imidazol[5,1-a]isoindol-5-yl)acetyl)piperidin-1yl)-2-oxoethyl)(phenyl) formate (900 mg, 1.75 mmol) according to the steps similar to those in Example 7.

LC-MS (m/z): 517 (M+1).

EXAMPLE 85

Preparation of 1-(4-(1-hydroxy-2-(5H-imidazo[5,1-a]isoindol-5-yl)ethyl)piperidin-1-yl)-2-(phenylamino)ethyl-1-one

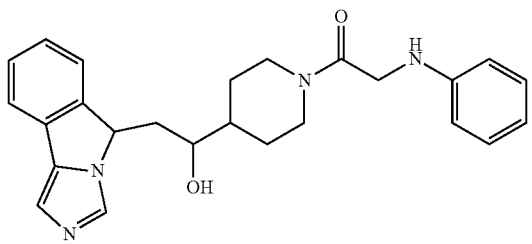 [SMILES: O=C(CNc1ccccc1)N1CCC(C(O)CC2c3ccccc3-c3cncn32)CC1]

tert-butyl (2-(4-(1-Hydroxy-2-(5H-imidazo[5,1-a]isoindol-5-yl)ethyl)piperidin-1-yl)-2-oxyethyl)(phenyl) formate (600 mg, 1.45 mmol) was dissolved in dichloromethane (20 ml). Concentrated hydrochloric acid (2 ml) was added and the mixture was reacted at room temperature for 3 hours. The residue was obtained by concentration under reduced pressure. It was poured into water (300 ml). The PH was adjusted to 8 to 9. A solid was precipitated and filtered, and purified by passing through column with DCM/MeOH=10/1 to obtain 1-(4-(1-hydroxy-2-(5H-imidazo[5,1-a]isoindol-5-yl)ethyl)piperidin-1yl)-2-(phenylamino)ethyl-1-one (225 mg, the yield was 46.5%).

$^1$H NMR (400 MHz, DMSO-d6) δ 7.96 (s, 0.8H), 7.92 (s, 0.2H), 7.63~7.51 (m, 2H), 7.40 (t, J=7.5 Hz, 1H), 7.29 (t, J=7.5 Hz, 1H), 7.16 (s, 0.2H),7.14 (s, 0.8H), 7.08 (t, J=7.6 Hz, 2H), 6.66 (d, J=7.9 Hz, 2H), 6.57 (t, J=7.1 Hz, 1H), 5.51(s, br, 1H), 5.41 (t, J=6.5 Hz, 1H), 5.14 (d, J=5.8 Hz, 0.16H), 5.03 (d, J=5.8 Hz, 0.84H), 4.45 (t, J=13.5 Hz, 1H), 3.97 (t, J=14.5 Hz, 1H), 3.88 (s, 2H), 3.71 (s, br, 1H), 2.96 (t, J=12.9 Hz, 1H), 2.12~2.05 (m, 1H), 1.93~1.80 (m, 2H), 1.64~1.54 (m, 2H), 1.32~1.15 (m, 2H).

LC-MS (m/z): 417 (M+1).

EXAMPLE 86

Preparation of ethyl N-methyl-N-(4-trifluoromethylphenyl)glycine

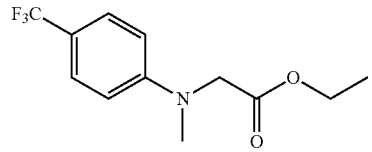 [SMILES: CCOC(=O)CN(C)c1ccc(C(F)(F)F)cc1]

Yellow oily ethyl N-methyl-N-(4-trifluoromethylphenyl) glycine (630 mg, 84%) was prepared from N-methyl-4-trifluoromethylaniline (500 mg, 2.86 mmol) and ethyl 2-bromoacetate (0.96 g, 5.72 mmol) according to the steps similar to those in Example 60.

LC-MS (m/z): 262 (M+1).

EXAMPLE 87

Preparation of
N-methyl-N-(4-trifluoromethylphenyl)glycine

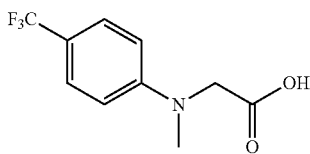

Yellow oily N-methyl-N-(4-trifluoromethylphenyl)glycine (470 mg, 87%) was prepared from ethyl N-methyl-N-(4-trifluoromethylphenyl)glycine (600 mg, 2.3 mmol) according to the steps similar to those in Example 61.
LC-MS (m/z): 234 (M+1).

EXAMPLE 88

Preparation of 1-(4-(2-(5H-imidazol[5,1-a]isoindol-5-yl)acetyl)piperidin-1-yl)-2-(methyl(4-trifluoromethylphenyl)amino)ethyl-1-one

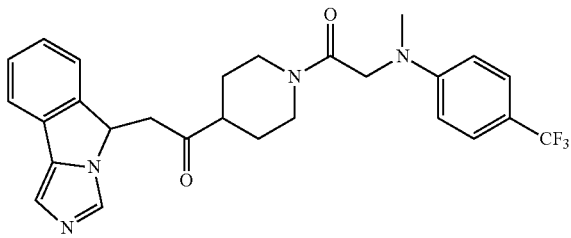 [SMILES: CN(CC(=O)N1CCC(C(=O)CC2c3ccccc3-c3cncn32)CC1)c1ccc(C(F)(F)F)cc1]

Yellow oily 1-(4-(2-(5H-imidazo[5,1-a]isoindol-5-yl) acetyl)piperidin-1yl)-2-(methyl(4-trifluoromethylphenyl) amino)ethyl-1-one (60 mg, 26%) was prepared from N-methyl-N-(4-trifluoromethylphenyl)glycine (140 mg, 0.6 mmol) and 2-(5H-imidazo[5,1-a])isoindol-5-yl)-1-(piperidin-4-yl)ethyl-1-one hydrochloride (130 mg, 0.46 mmol) according to the steps similar to those in Example 62.
LC-MS (m/z): 497 (M+1).

EXAMPLE 89

Preparation of 1-(4-(1-hydroxy-2-(5H-imidazo[5,1-a]isoindol-5-yl)ethyl)piperidin-1-yl)-2-(methyl(4-trifluoromethyphenyl)amino)ethyl-1-one

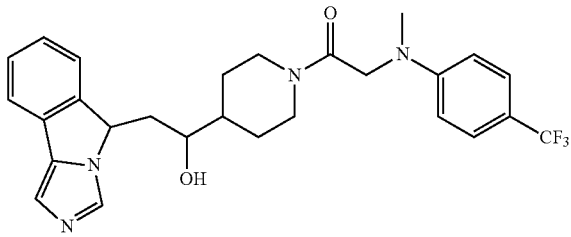 [SMILES: CN(CC(=O)N1CCC(C(O)CC2c3ccccc3-c3cncn32)CC1)c1ccc(C(F)(F)F)cc1]

White solid 1-(4-(1-hydroxy-2-(5H-imidazo[5,1-a]isoindol-5-yl)ethyl)piperidin-1-yl)-2-(methyl(4-trifluoromethylphenyl)amino)ethyl-1-one (35 mg, 58%) was prepared from 1-(4-(2-(5H-imidazo[5,1-a]isoindol-5-yl)acetyl)piperidin-1-yl)-2-(methyl(4 -trifluoromethylphenyl)amino)ethyl-1one (60 mg, 0.12 mmol) according to the steps similar to those in Example 63.
$^1$H NMR (400 MHz, CD3OD) δ 8.28 (s, 1H), 7.69~7.58 (m, 2H), 7.47~7.36 (m, 4H), 7.30~7.28 (m, 1H), 6.73 (d, J=8Hz, 2H), 5.63~5.53 (m, 1H), 4.52 (t, J=14 Hz, 1H), 4.40~4.28 (m, 2H), 4.00 (t, J=18 Hz, 1H), 3.80~3.69 (m, 1H), 3.13~3.02 (m, 4H), 2.61 (t, J=12 Hz, 1H), 2.20~2.15 (m, 2H), 1.94~1.88 (m, 1H), 1.75~1.58 (m, 2H), 1.45~1.37 (m, 2H).
LC-MS (m/z): 499 (M+1).

EXAMPLE 90

Preparation of ethyl
(3-trifluoromethylphenyl)glycine

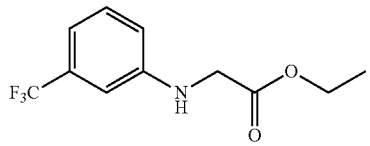 [SMILES: CCOC(=O)CNc1cccc(C(F)(F)F)c1]

Yellow oily ethyl (3-trifluoromethylphenyl)glycine (850 mg, 55%) was prepared from 3-trifluoromethylaniline (1 g, 6.2 mmol) and ethyl 2-bromoacetate (1.55 g, 9.3 mmol) according to the steps similar to those in Example 64.
LC-MS (m/z): 248 (M+1).

EXAMPLE 91

Preparation of ethyl
N-methyl-N-(3-trifluoromethylphenyl)glycine

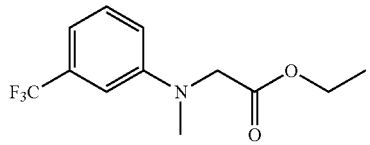 [SMILES: CCOC(=O)CN(C)c1cccc(C(F)(F)F)c1]

White solid ethyl N-methyl-N-(3-trifluoromethylphenyl) glycine (430 mg, 81%) was prepared from N-methyl-3-trifluoromethylaniline (500 mg, 2.02 mmol) and methyl iodide (1.43 g, 10.1 mmol) according to the steps similar to those in Example 65.
LC-MS (m/z): 262 (M+1).

EXAMPLE 92

Preparation of
N-methyl-N-(3-trifluoromethylphenyl)glycine

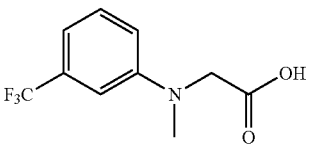 [SMILES: CN(CC(=O)O)c1cccc(C(F)(F)F)c1]

Yellow oily N-methyl-N-(3-trifluoromethylphenyl)glycine (320 mg, 90%) was prepared from ethyl N-methyl-N-(3-trifluoromethylphenyl)glycine (400 mg, 1.5 mmol) according to the steps similar to those in Example 66.

LC-MS (m/z): 234 (M+1).

EXAMPLE 93

Preparation of 1-(4-(2-(5H-imidazo[5,1-a]isoindol-5-yl)acetyl)piperidin-1-yl)-2-(methyl(3-trifluoromethylphenyl)amino)ethyl-1one

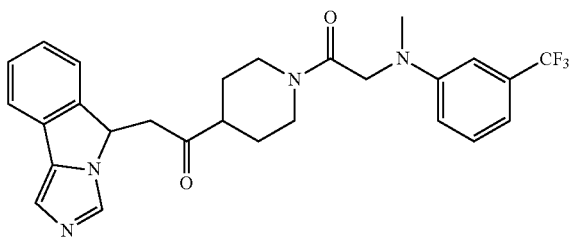 [SMILES: CN(CC(=O)N1CCC(C(=O)CC2c3ccccc3-c3cncn32)CC1)c1cccc(C(F)(F)F)c1]

Yellow oily 1-(4-(2-(5H-imidazo[5,1-a]isoindol-5-yl)acetyl)piperidin-1yl)-2-(methyl (3-trifluoromethylphenyl)amino)ethyl-1-one (60 mg, 24%) was prepared from N-methyl-N-(3-trifluoromethylphenyl)glycine (151 mg, 0.65 mmol) and 2-(5H-imidazo[5,1-a])isoindol-5-yl)-1-(piperidin-4-yl)ethyl-1one hydrochloride (140 mg, 0.5 mmol) according to the steps similar to those in Example 58.

LC-MS (m/z): 497 (M+1).

EXAMPLE 94

Preparation of 1-(4-(1-hydroxy-2-(5H-imidazo[5,1-a]isoindol-5-yl)ethyl)piperidin-1-yl)-2-(3-trifluoromethylphenyl)amino)ethyl-1one

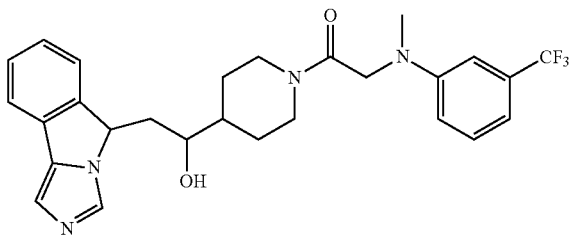 [SMILES: CN(CC(=O)N1CCC(C(O)CC2c3ccccc3-c3cncn32)CC1)c1cccc(C(F)(F)F)c1]

White solid 1-(4-(1-hydroxy-2-(5H-imidazo[5,1-a]isoindol-5-yl)ethyl)piperidin-1-yl)-2-(methyl(3-trifluoromethylphenyl)amino)ethyl-1-one (35 mg, 58%) was prepared from 1-(4-(2-(5H-imidazo[5,1-a]isoindol-5-yl)acetyl)piperidin-1yl)-2-(methyl(3-trifluoromethylphenyl)amino)ethyl-1one (60 mg, 0.12 mmol) according to the steps similar to those in Example 7.

¹H NMR (400 MHz, CD3OD) δ 8.02 (s, 1H), 7.64~7.56 (m, 2H), 7.44~7.40 (m, 1H), 7.35~7.29 (m, 2H), 7.16 (s, 1H), 6.91~6.86 (m, 3H), 5.54~5.45 (m, 1H), 4.53 (t, J=20 Hz, 1H), 4.40~4.26 (m, 2H), 4.02 (t, J=18 Hz, 1H), 3.82~3.77 (m, 1H), 3.13~3.06 (m, 4H), 2.62 (t, J=12 Hz, 1H), 2.20~2.15 (m, 2H), 1.98~1.90 (m, 1H), 1.75~1.61 (m, 2H), 1.43~1.34 (m, 2H).

LC-MS (m./z): 499 (M+1).

EXAMPLE 95

Preparation of ethyl N-(4-cyanophenyl)-N-methylglycine

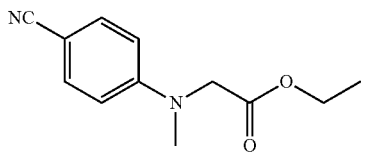 [SMILES: CCOC(=O)CN(C)c1ccc(C#N)cc1]

Yellow oily ethyl N-(4-cyanophenyl)-N-methylglycine (260 mg, 32%) was prepared from N-methyl-4-cyanoaniline (500 mg, 3.79 mmol) and ethyl 2-bromoacetate (759 mg, 4.55 mmol) according to the steps similar to those in Example 60.

LC-MS (m/z): 219 (M+1).

EXAMPLE 96

Preparation of N-(4-cyanophenyl)-N-methylglycine

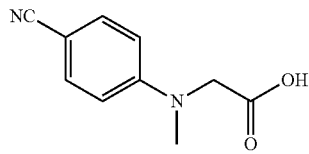

Yellow oily N-(4-cyanophenyl)-N-methylglycine (250 mg, 92%) was prepared from ethyl N-(4-cyanophenyl)-N-methylglycine (310 mg, 1.42 mmol) according to the steps similar to those in Example 61.

LC-MS (m/z) 191: (M+1).

EXAMPLE 97

Preparation of 1-(4-(2-(5H-imidazo[5,1-a]isoindol-5-yl)acetyl)piperidin-1yl)-2-((4-cyanophenyl)(methyl)amino)ethyl-1-one

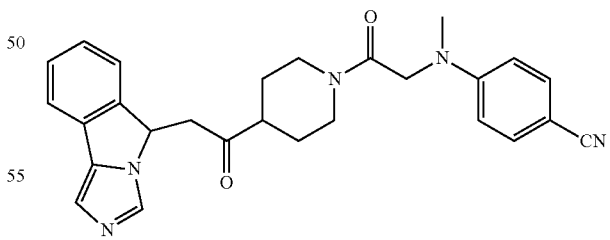

White solid 1-(4-(2-(5H-imidazo[5,1-a]isoindol-5-yl)acetyl)piperidin-1-yl)-2-((4-cyanophenyl)(methyl)amino)ethyl-1-one (100 mg, 63%) was prepared from N-(4-cyanophenyl)-N-methylglycine (74 mg, 0.39 mmol) and 2-(5H-imidazo[5,1-a])isoindol-5-yl)-1-(piperidin-4-yl)ethyl-1-one hydrochloride (100 mg, 0.36 mmol) according to the steps similar to those in Example 62.

LC-MS (m/z): 454 (M+1)

EXAMPLE 98

Preparation of 2-((4-cyanophenyl)(methyl)amino)-1-4-(1-hydroxy-2-(5H-imidazo[5,1-a]isoindol-5-yl)ethyl)piperidin-1-yl)ethyl-1-one

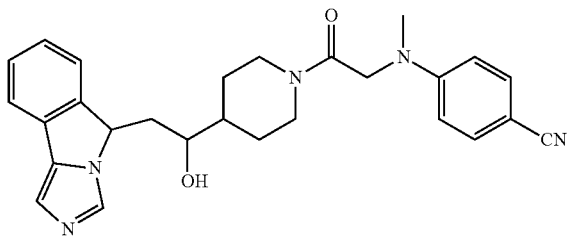 [SMILES: CN(CC(=O)N1CCC(C(O)CC2c3ccccc3-c3cncn32)CC1)c1ccc(C#N)cc1]

White solid 2-((4-cyanophenyl)(methyl)amino)-1-4-(1-hydroxy-2-(5H-imidazo[5,1-a]isoindol-5-yl)ethyl)piperidin-1-yl)ethyl-1-one (45 mg, 45%) was prepared from 1-(4-(2-(5H-imidazo[5,1-a]isoindol-5-yl)acetyl)piperidin-1yl)-2-((4-cyanophenyl)(methyl)amino)ethyl-1-one (100 mg, 0.22 mmol) according to the steps similar to those in Example 63.

$^1$HNMR (400 MHz, CD3OD) δ 8.006(d, 1H) 7.622(d, J=7.6 Hz, 1H), 7.563(d, J=7.6, 1H), 7.403~7.504(m, 3H), 7.335(t, J=7.6 Hz, 1H), 7.157(d, 1H), 6.703~6.731(m, 2H), 5.448~5.537 (m, 1H), 4.528(t, J=16 Hz, 1H), 4.325~4.439 (m, 2H), 3.974(t, J=16 Hz, 1H), 3.751~3.819(m, 1H), 3.078~3.134(m, 4H), 2.624 (t, J=13.6 Hz, 1H), 2.067~2.367 (m, 2H), 1.939(t, J=13.6 Hz, 1H), 1.610~1.802(m, 2H), 1.212~1.482(m, 2H).

LC-MS (m/z): 456 (M+1).

EXAMPLE 99

Preparation of ethyl N-(3-methoxyphenyl)-N-methylglycine

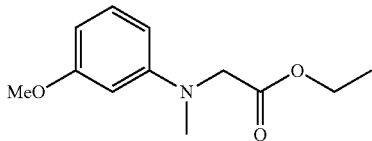 [SMILES: CCOC(=O)CN(C)c1cccc(OC)c1]

Ethyl N-(3-Methoxyphenyl)-N-methylglycine (400 mg, 49%) was prepared from 3-methoxy-N-methylaniline (500 mg, 3.65 mmol) and ethyl 2-bromoacetate (731 mg, 4.38 mmol) according to the steps similar to those in Example 60.

LC-MS (m/z): 224 (M+1).

EXAMPLE 100

Preparation of N-(3-methoxyphenyl-N-methylglycine

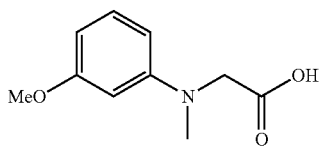

N-(3-Methoxylphenyl)-N-methylglycine (300 mg, 85%) was prepared from ethyl N-(3-methoxyphenyl)-N-methylglycine (400 mg, 1.8 mmol) according to the steps similar to those in Example 61.

LC-MS (m/z): 196 (M+1).

EXAMPLE 101

Preparation of 1-(4-2-(5H-imidazo[5,1-a]isoindol-5-yl)acetyl)piperidin-1yl)-2-((3-methoxyphenyl)(methyl)amino)ethyl-1one

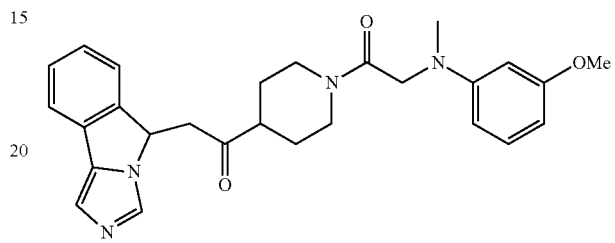

White solid 1-(4-(2-(5H-imidazo[5,1-a]isoindol-5-yl)acetyl)piperidin-1-yl)-2-((3-methoxyphenyl)(methyl)amino)ethyl-1-one (100 mg, 61%) was prepared from N-(3-methoxyphenyl)-N-methylglycine (76 mg, 0.39 mmol) and 2-(5H-imidazo[5,1-a]isoindol-5-yl)-1-(piperidin-4-yl)ethyl-1-one hydrochloride (100 mg, 0.36 mmol) according to the steps similar to those in Example 62.

LC-MS (m/z): 459 (M+1).

EXAMPLE 102

Preparation of 2-((3-methoxyphenyl)(methyl)amino)-1-(4-(1-hydroxy-2-(5H-imidazol[5,1-a]isoindol-5-yl)ethyl)piperidin-1-yl)ethyl-1-one

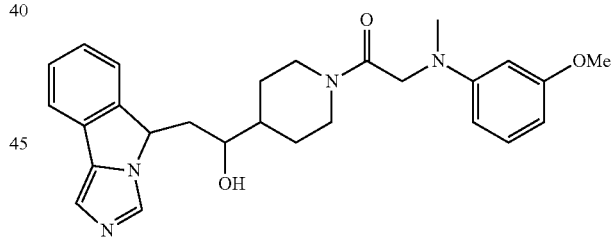

White solid 2-((3-methoxyphenyl)(methyl)amino)-1-(4-(1-hydroxy-2-(5H-imidazo[5,1-a]isoindol-5-yl)ethyl)piperidin-1yl)ethyl-1-one (55 mg, 55%) was prepared from 1-(4-(2-(5H-imidazo[5,1-a]isoindol-5-yl)acetyl)piperidin-1-yl)-2-((3-methoxyphenyl)(methyl)amino)ethyl-1one (100 mg, 0.22 mmol) according; to the steps similar to those in Example 63.

$^1$HNMR (400 MHz, CD3OD) δ 8.032(s, 1H), 7.629(d, J=7.6 Hz, 1H), 7.580(d, j=7.6 Hz, 1H), 7.427(t, J=7.6 Hz, 1H), 7.339(t, J=7.6 Hz, 1H), 7.172(s, 1H), 7.056(t, J=8 Hz, 1H), 6.272(t, J=9.6 Hz, 2H). 6.194(s, 1H), 5.445-5.541(m, 1H), 4.543(t, J=15.2 Hz, 1H), 4.141-4.290(m, 2H), 4.023(t, J=15.2 Hz, 1H), 3.764-3.811(m, 1H), 3.723(s, 3H), 3.076(t, J=12.8 Hz, 1H), 3.002(s, 3H), 2.608(t, J=12.8 Hz, 1H), 2.032-2.348(m, 2H), 1.911 (t, J=11.2 Hz, 1H), 1.615-1.783 (m, 2H), 1.192-1.423(m, 2H).

ESI LC-MS (m/z): 461 (M+1).

EXAMPLE 103

Preparation of N-methyl-N-(4-nitrophenyl)glycine

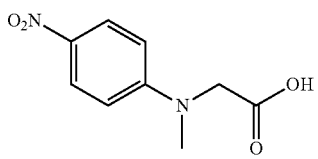

NaH (60% in mineral oil, 960 mg, 24 mmol) was added to a solution of N-methyl-4-nitroaniline (3 g, 20 mmol) in tetrahydrofuran (50 ml) at 0° C. The reaction solution was stirred at 0° C. for 0.5 hours, and ethyl 2-bromopropionate (3.65 g, 22 mmol) was added thereto. The reaction was allowed to react at room temperature for 2 hours. Then NaOH solution (1N, 40 ml, 40 mmol) was added. The reaction was continued for another 1 hour. The reaction was terminated. The reaction solution was poured into 100 ml of water, extracted twice with ethyl acetate (100 ml×2). The combined organic phases were washed with saturated brine, dried over anhydrous sodium sulfate, filtered and subjected to spin drying. The residue was passed through column (the developing solvent was dichloromethane:methanol=30:1) to obtain a yellow solid N-(4-nitrophenyl)-N-methylglycine (1.2 g, 28.6%).

LC-MS (m/z): 211 (M+1).

EXAMPLE 104

Preparation of 1-(4-(2-(5H-imidazo[5,1-a]isoindol-5-yl)acetyl)piperidin-1-yl)-2-(methyl(4-nitrophenyl)amino)ethyl-1-one

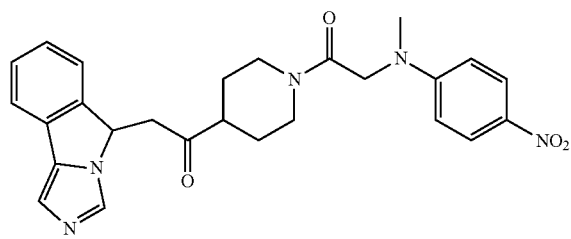 [SMILES: CN(CC(=O)N1CCC(C(=O)CC2c3ccccc3-c3cncn32)CC1)c1ccc([N+](=O)[O-])cc1]

Yellow solid 1-(4-(2-(5H-imidazol[5,1-a]isoindol-5-yl)acetyl)piperidin-1-yl)-2-(methyl(4-nitrophenyl)amino)ethyl-1-one (70 mg, 55%) was prepared from N-methyl-N-(4-nitrophenyl)glycine (50 mg, 0.23 mmol) and 2-(5H-imidazo[5,1-a]isoindol-5-yl)-1-(piperidin-4-yl)ethyl-1one hydrochloride (60 mg, 0.21 mmol) according to the steps similar to those in Example 62.

LC-MS (m/z): 474 (M+1).

EXAMPLE 105

Preparation of 1-(4-(1-hydroxy-2-(5H-imidazo[5,1-a]isoindol-5-yl)ethyl)piperidin-1-yl)-2-(methyl(4-nitrophenyl)amino)ethyl-1-one

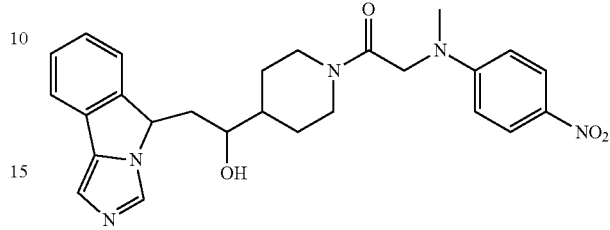

Yellow solid 1-(4-(1-hydroxy-2-(5H-imidazo[5,1-a]isoindol-5-yl)ethyl)piperidin-1yl)-2-(methyl(4-nitrophenyl)amino)ethyl-1one (30 mg, 42%) was prepared from 1-(4-(2-(5H-imidazo[5,1-a]isoindol-5-yl)acetyl)piperidin-1yl)-2-(methyl(4 -nitrophenyl)amino)ethyl-1one (70 mg, 0.15 mmol) according to the steps similar to those in Example 63.

$^1$HNMR (400 MHz, MeOD) δ 8.079(d, J=9.6 Hz, 2H) 8.015(s, 1H), 7.627(d, J=7.6 Hz, 1H), 7.590(d, J=7.6 Hz, 1H), 7.426(t, J=7.6 Hz, 1H), 7.340(t, J=7.6 Hz, 1H), 7.162(s, 1H), 6.702(d, J=9.6 Hz, 2H), 4.462-5.556(m, 1H), 4.407-4.577(m, 2H), 3.982(t, J=13.2 Hz, 1H), 3.730-3.830(m, 1H), 3.091-3.150(m, 4H), 2.642(t, J=13.2 Hz, 1H), 2.110-2.200 (m, 1H), 1.949(t, J=15.6 Hz, 1H), 1.614-1.762(m, 2H) 1.278-1.461(m, 3H).

LC-MS (m/z): 476 (M+1).

EXAMPLE 106

Preparation of ethyl N-methyl N-(pyridin-2-yl)glycine

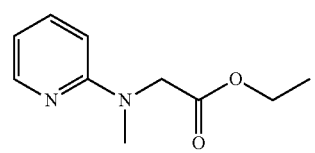

Yellow oily ethyl N-methyl-N-(pyridin-2-yl)glycine (650 mg, 60%) was prepared from N-methyl-pyridine-2-amine (600 mg, 5.5 mmol) and ethyl 2-bromoacetate (1.39 g, 8.3 mmol) according to the steps similar to those in Example 60.

LC-MS (m/z): 195 (M+1).

EXAMPLE 107

Preparation of N-methyl-N-(pyridin-2-yl)glycine

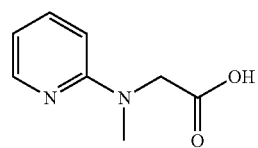

Yellow oily N-methyl-N-(pyridin-2-yl)glycine (160 mg, 93%) was prepared from ethyl N-methyl-N-(pyridin-2-yl)glycine (200 mg, 1.03 mmol) according to the steps similar to those in Example 61.

LC-MS (m/z): 167 (M+1).

EXAMPLE 108

Preparation of 1-(4-(2-(5H-imidazo[5,1a-]isoindol-5-yl)acetyl)piperidin-1-yl)-2-(methyl(pyridin-2-yl)amino)ethyl-1-one

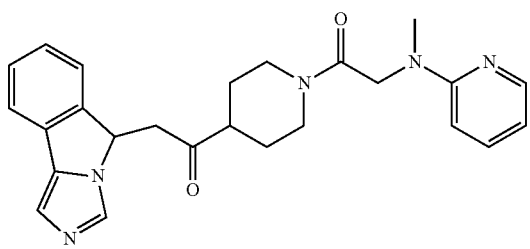 [SMILES: CN(CC(=O)N1CCC(C(=O)CC2c3ccccc3-c3cncn32)CC1)c1ccccn1]

Yellow oily 1-(4-(2-(5H-imidazo[5,1-a]isoindol-5-yl)acetyl)piperidin-1yl)-2-(methyl(pyridin-2-yl)amino)ethyl-1-one (70 mg, 29%) was prepared from N-methyl-N-(pyridin-2-yl)glycine (122 mg, 0.74 mmol) and 2-(5H-imidazo[5,1-a]isoindol-5-yl)-1-(piperidin-4-yl)ethyl-1-one hydrochloride (160 mg, 0.57 mmol) according to the steps similar to those in Example 58.

LC-MS (m/z): 430 (M+1).

EXAMPLE 109

Preparation of 1-(4-(1-hydroxy-2-(5H-imidazo[5,1-a]isoindol-5-yl)ethyl)piperidin-1-yl)-2-(methyl(pyridin-2-yl)amino)ethyl-1-one

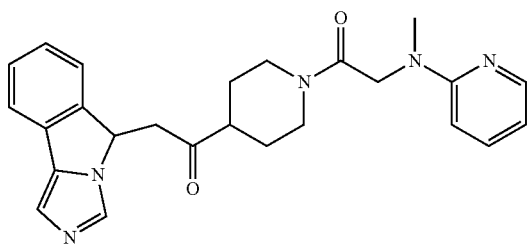 [SMILES: CN(CC(=O)N1CCC(C(=O)CC2c3ccccc3-c3cncn32)CC1)c1ccccn1]

White solid 1-(4-(1-hydroxy-2-(5H-imidazo[5,1-a]isoindol-5-yl)ethyl)piperidin-1yl)-2-(methyl(pyridin-2-yl)amino)ethyl-1-one (19 mg, 27%) was prepared from 1-(4-(2-(5H-imidazo[5,1-a]isoindol-5-yl)acetyl)piperidin-1yl)-2-(methyl(pyridin-2-yl)ethyl-1-one (70 mg, 0.16 mmol) according to the steps similar to those in Example 7.

$^1$H NMR (400 MHz, CD3OD) δ 8.02~7.97 (m, 2H), 7.64~7.62 (d, J=8 Hz, 1H), 7.58~7.50 (m, 2H), 7.42 (t, J=16 Hz, 1H), 7.33 (t, J=16 Hz, 1H), 7.16 (s, H), 6.66 (d, J=8 Hz, 1H), 6.60 (t, J=12 Hz, 1H), 5.48~5.45 (m, 1H), 4.56~4.41 (m, 3H), 4.06~3.98 (m, 1H), 3.87~3.78 (m, 1H), 3.12~3.07 (m, 4H), 2.60 (t, J=12 Hz, 1H), 2.18~2.10 (m, 2H), 1.94~1.88 (m, 1H), 1.68~1.59 (m, 2H), 1.43~1.35 (m, 2H).

LC-MS (m/z): 432 (M+1).

EXAMPLE 110

Preparation of ethyl quinolin-6-yl glycine

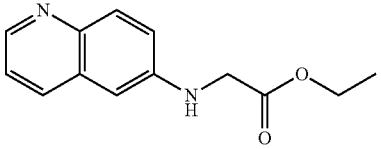 [SMILES: CCOC(=O)CNc1ccc2ncccc2c1]

6-Aminoquinoline (2000 mg, 13.9 mmol), ethyl 2-bromoacetate (3479 mg, 20.8 mmol), diisopropylethylamine (5375 mg, 41.6 mmol) and 30 ml of acetonitrile were added into a 100 ml pear-shaped flask. The mixture was allowed to react at 50° C. for 16 hours. The reaction was terminated. It was cooled to room temperature, and concentrated. The residue was passed through column (the developing solvent was petroleum ether:ethyl acetate=10:1) to obtain ethyl quinolin-6-yl glycine (1200 mg, the yield was 37%).

LC-MS (m/z): 231 (M+1).

EXAMPLE 111

Preparation of N-methyl-N-(quinolin-6-yl)glycine

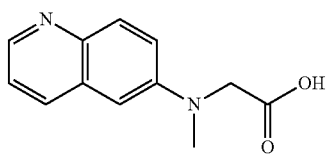 [SMILES: CN(CC(=O)O)c1ccc2ncccc2c1]

Ethyl Quinolin-6-yl glycine (1200 mg, 5.21 mmol) was dissolved in methanol (20 ml), and formaldehyde (1513 mg, 52.1 mmol) was added thereto. The reaction solution was stirred at room temperature for 2 hours and then sodium cyanoborohydride (1643 mg, 26.1 mmol) was added thereto. The mixture was stirred at room temperature for 16 hours. 50 ml of water was added to the reaction solution, and then extracted once with ethyl acetate (30 ml). The aqueous phase was adjusted to pH=5-6 with 1 mil aqueous hydrochloric acid, and then extracted three times with dichloromethane/isopropanol (v/v=3/1, 30 ml), The combined organic phases were dried over anhydrous sodium sulfate and subjected to spin drying to obtain a yellow oily substance N-methyl-N-(quinolin-6-yl)glycine (310 mg, 28%).

LC-MS (m/z): 217 (M+1).

EXAMPLE 112

Preparation of 1-(4-(2-(5H-imidazo[5,1-a]isoindol-5-yl)acetyl)piperidin-1yl)-2-quinolin-6-yl)amino)ethyl-1-one

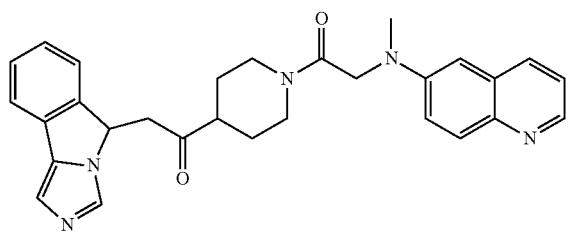 [SMILES: CN(CC(=O)N1CCC(C(=O)CC2c3ccccc3-c3cncn32)CC1)c1ccc2ncccc2c1]

Yellow oily 1-(4-(2-(5H-imidazo[5,1-a]isoindol-5-yl)acetyl)piperidin-1-yl)-2-(methyl(quinolin-6-yl)amino)ethyl-1-1-one (45 mg, 26%) was prepared from N-methyl-N-(quinolin-6-yl)glycine (100 mg, 0.46 mmol) and 2-(5H-imidazo[5,1-a])isoindol-5-yl)-1-(piperidin-4-yl)ethyl-1-one hydrochloride (100 mg, 0.36 mmol) according to the steps similar to those in Example 62.

LC-MS (m/z): 480 (M+1).

EXAMPLE 113

Preparation of 1-(4-(1-hydroxy-2-(5H-imidazo[5,1-a]isoindol-5-yl)ethyl)piperidin-1-yl)-2-(methyl(quinolin-6-yl)amino)ethyl-1-one

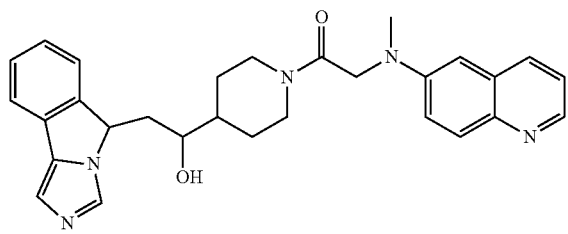 [SMILES: CN(CC(=O)N1CCC(C(O)CC2c3ccccc3-c3cncn32)CC1)c1ccc2ncccc2c1]

Light yellow solid 1-(4-(1-hydroxy-2-(5H-imidazo[5,1-a]isoindol-5-yl)ethyl)piperidin-1-yl)-2-(methyl(quinolin-6-yl)amino)ethyl-1-one (15 mg, 33%) was prepared from 1-(4-(2-(5H-imidazo[5,1-a]isoindol-5-yl)acetyl)piperidin-1-yl)-2-(methyl(quinolin-6-yl)ethyl-1-one (45 mg, 0.09 mmol) according to the steps similar to those in Example 63.

$^1$H NMR (400 MHz, CD3OD) δ 8.50 (s, 1H), 8.11 (d, J=8 Hz, 1H), 8.04 (s, 1H), 7.84 (d, J=8 Hz, 1H), 7.64 (d, J=8 Hz, 1H), 7.58 (d, J=8 Hz, 1H), 7.45~7.32 (m, 4H), 7.17 (s, 1H), 6.91 (s, 1H), 5.49~5.46 (m, 1H), 4.63~4.42 (m, 3H), 4.09~4.02 (m, 1H), 3.82~3.81 (m, 1H), 3.19~3.09 (m, 4H), 2.64 (t, J=14 Hz, 1H), 2.22~2.10 (m, 2H), 1.99~1.90 (m, 1H), 1.78~1.62 (m, 2H), 1.47~1.37 (m, 2H).

LC-MS (m/z): 482 (M+1).

EXAMPLE 114

Preparation of N-methyl-9-(tetrahydro-2H-pyran-2-yl)-9H-purine-6-amine

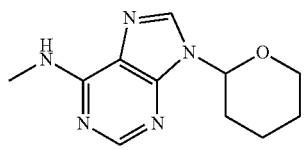 [SMILES: CNc1ncnc2c1ncn2C1CCCCO1]

6-Chloro-9-(tetrahydro-2H-pyran-2-yl)-9H-purine (1500 mg, 6.3 mmol) and methylamine alcohol solution (30 ml). The reaction solution was stirred at 75° C. for 5 hours. After spin drying, a yellow oily substance N-methyl-9-(tetrahydro-2H-pyran-2-yl)-4)-9H-purine-6-amine (900 mg, 61%) was obtained.

LC-MS (m/z): 234 (M+1).

EXAMPLE 115

Preparation of ethyl N-methyl-N-(9-(tetrahydro-2H-pyran-2-yl)-9H-purin-6-yl)glycine

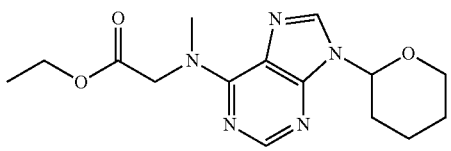 [SMILES: CCOC(=O)CN(C)c1ncnc2c1ncn2C1CCCCO1]

N-Methyl-9-(tetrahydro-2H-pyran-2-yl)-9H-purine-6-amine (900 mg, 3.86 mmol) and DMF (10 ml) were added to a round-bottom flask. Sodium hydride (60% content) (310 mg, 7.72 mmol) was added at 0° C. The reaction solution was stirred at 35° C. for 1 hour. And then ethyl 2-bromoacetate (967 mg, 5.79 mmol) was added into the reaction solution. The reaction solution was stirred at 35° C. for 3 hours, and quenched with 20 ml of water. Then ethyl acetate (50 ml) was added and the mixture was washed with saturated brine (40 ml) for 4 times. The organic phase was dried over anhydrous sodium sulfate, filtered arid subject to spin drying. The residue was passed through column (the developing solvent was dichloromethane:methanol=20:1) to obtain a white solid ethyl N-methyl-N-(9-(tetrahydro-2H-pyran-2-yl)-9H-purin-6-yl)glycine (1100 mg, the yield was 89%).

LC-MS (m/z): 320 (M+1).

EXAMPLE 116

Preparation of N-methyl-N-(9-(tetrahydro-2H-pyran-2-yl)-9H-purin-6-yl)glycine

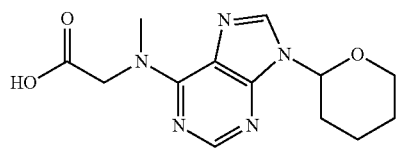 [SMILES: CN(CC(=O)O)c1ncnc2c1ncn2C1CCCCO1]

Ethyl N-methyl-N-(9-(tetrahydro-2H-pyran-2-yl)-9H-purin-6-yl)glycine (550 mg, 1.72 mmol) was dissolved in methanol (10 ml) and tetrahydrofuran (10 ml), and 10 ml of lithium hydroxide (1 mol/l) was added. The mixture was allowed to react at room temperature for 3 hours. The reaction was terminated. The reaction solution was adjusted to pH=6 with 1 mol/l hydrochloric acid, extracted 3 times with ethyl acetate. The combined organic phases were washed 3 times with saturated brine, dried over anhydrous sodium sulfate, filtered and subjected to spin drying to obtain a white solid N-methyl-N-(9-(tetrahydro-2H-pyran-2-yl)-9H-purin-6-yl)glycine (430 mg, 86%).

LC-MS (m/z): 292 (M+1).

EXAMPLE 117

Preparation of N-methyl-N-(9H-purin-6-yl)glycine

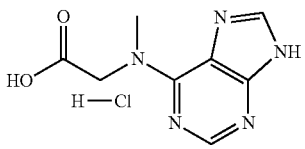

N-Methyl-N-(9-(tetrahydro-2H-pyran-2-yl)-9H-purin-6-yl)glycine (170 mg, 0.58 mmol) was dissolved in hydrochloric acid/dioxane solution (10 ml) and DMF (0.5 ml). The reaction solution was stirred at room temperature for 1 hour to obtain a spin-dried yellow oily substance N-methyl-N-(9H-purin-6-yl)glycine (130 mg, 92%). LC-MS (m/z) 208 (M-HCl+1).

EXAMPLE 118

Preparation of 1-(4-(2-(5H-imidazo[5,1-a]isoindol-5-yl)acetyl)piperidin-1-yl)-2-(methyl(7H-purin-6-yl)amino)ethyl-1-one

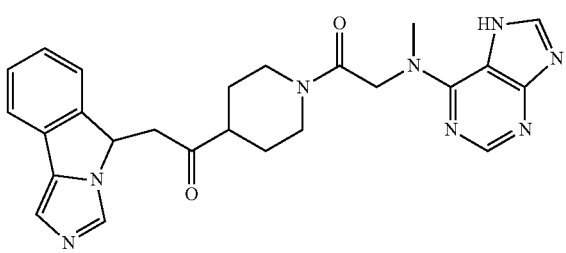 [SMILES: CN(CC(=O)N1CCC(C(=O)CC2c3ccccc3-c3cncn32)CC1)c1ncnc2nc[nH]c12]

Yellow oily 1-(4-(2-(5H-imidazo[5,1-a]isoindol-5-yl)acetyl)piperidin-1-yl)-2-(methyl(7H-purin-6-yl)amino)ethyl-1-one (60 mg, 24%) was prepared from N-methyl-N-(9H-purin-6-yl)glycine (130 mg, 0.69 mmol) and 2-(5H-imidazo[5,1-a])isoindol-5-yl)-1-(piperidin-4-yl)ethyl-1-one hydrochloride (150 mg, 0.54 mmol) according to the steps similar to those in Example 62.

LC-MS (m/z): 471 (M+1).

EXAMPLE 119

Preparation of 1-(4-(1-hydroxy-2-(5H-imidazo[5,1-a]isoindol-5-yl)ethyl)piperidin-1-yl)-2-(methyl(7H-purin-6-yl)amino)ethyl-1-one

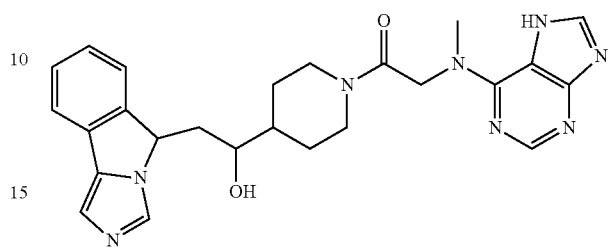

White solid 1-(4-(1-hydroxy-2-(5H-imidazo[5,1-a]isoindol-5-yl)ethyl)piperidin-1-yl)-2-(methyl(7H-purin-6-yl)amino)ethyl-1one (13 mg, 22%) was prepared from 1-(4-(2-(5H-imidazo[5,1-a]isoindol-5-yl)acetyl)piperidin-1yl)-2-(methyl(7H-purin-6-yl)ethyl-1-one (60 mg, 0.13 mmol) according to the steps similar to those in Example 63.

$^1$H NMR (400 MHz, CD3OD) δ 8.21 (s, 1H), 8.03~7.90 (m, 2H), 7.64~7.57 (m, 2H), 7.44~7.32 (m, 2H), 7.17 (s, 1H), 5.49~5.46 (m, 1H), 4.51 (t, J=14 Hz, 1H), 4.08~4.00 (m, 1H), 3.82~3.77 (m, 1H), 3.50~3.33 (m, 4H), 3.17~3.11 (m, 1H), 2.66~2.60 (m, 1H), 2.23~2.10 (m, 2H), 1.96~1.86 (m, 4H), 1.33~1.25 (m, 2H).

LC-MS (m/z): 473 (M+1).

EXAMPLE 120

Preparation of ethyl dibenzo[b,d]furan-3-yl glycine

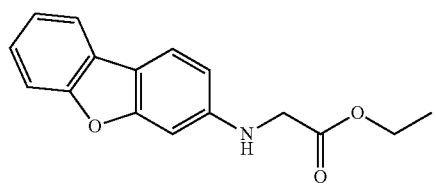 [SMILES: CCOC(=O)CNc1ccc2c(c1)oc1ccccc12]

Yellow oily ethyl dibenzo[b,d]furan-3-yl glycine (570 mg, 65%) was prepared from 3-aminodibenzo[b,d]furan (600 mg, 3.3 mmol) and ethyl 2-bromoacetate (821 mg, 4.9 mmol) is according to the steps similar to those in Example 64.

LC-MS (m/z): 270 (M+1).

EXAMPLE 121

Preparation of ethyl N-(dibenzo[b,d]furan-3-yl)-N-methylglycine

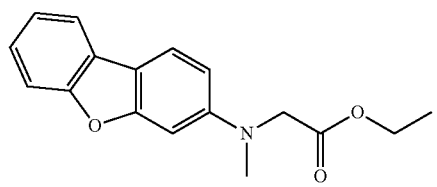 [SMILES: CCOC(=O)CN(C)c1ccc2c(c1)oc1ccccc12]

Greyish white solid ethyl N-(dibenzo[b,d]furan-3-yl)-N-methylglycine (350 mg, 83%) was prepared from ethyl dibenzo[b,d]furan-3-yl glycine (400 mg, 1.48 mmol) and methyl iodide (1.05 g, 7.43 mmol) according to the steps similar to those in Example 65.

LC-MS (m/z): 284 (M+1).

EXAMPLE 122

Preparation of N-(dibenzo[b,d]furan-3-yl-N-methyl-glycine

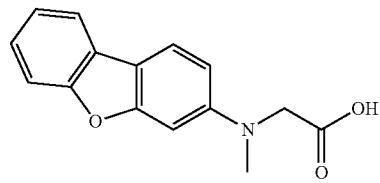 [SMILES: CN(CC(=O)O)c1ccc2c(c1)oc1ccccc12]

Light yellow solid N-(dibenzo[b,d]furan-3-yl)-N-methylglycine (200 mg, 92%) was prepared from ethyl N-(dibenzo[b,d]furan-3-yl)-N-methylglycine (240 mg, 0.85) according to the steps similar to those in Example 66.

LC-MS (m/z): 256 (M+1).

EXAMPLE 123

Preparation of 1-(4-(2-(5H-imidazo[5,1-a]isoindol-5-yl)acetyl)piperidin-1-yl)-2-(dibenzo[b,d]furan-3-yl(methyl)amino)ethyl-1-one

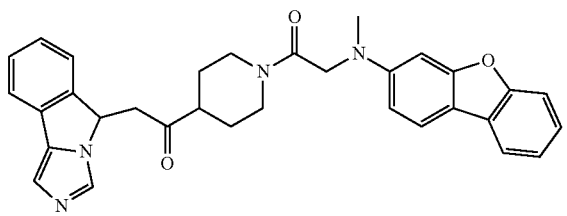 [SMILES: CN(CC(=O)N1CCC(C(=O)CC2c3ccccc3-c3cncn32)CC1)c1ccc2c(c1)oc1ccccc12]

Yellow oily 1-(4-(2-(5H-imidazo[5,1-a]isoindol-5-yl)acetyl)piperidin-1yl)-2-(dibenzo[b,d]furan-3-yl(methyl)amino)ethyl-1one (150 mg, 45%) was prepared from N-(dibenzo[b,d]furan-3-yl)-N-methylglycine (190 mg, 0.83 mmol) and 2-(5H-imidazo[5,1-a]isoindol-5-yl)-1-(piperidin-4-yl)ethyl-1-one hydrochloride (180 mg, 0.64 mmol) according to the steps similar to those in Example 67.

LC-MS (m/z): 519 (M+1).

EXAMPLE 124

Preparation of 2-(dibenzo[b,d]furan-3-yl(methyl)amino)-1-(4-(1-hydroxy-2-(5H-imidazo[5,1-a]isoindol-5-yl)ethyl)piperidin-1yl)ethyl-1-one

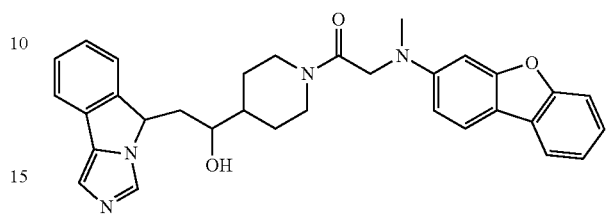

White solid 2-(dibenzo[b,d]furan-3-yl(methyl)amino)-1-(4-(1-hydroxy-2-(5H-imidazo[5,1-a]isoindol-5-yl)ethyl)piperidin-1-yl)ethyl-1 -one (70 mg, 46%) was prepared from 1-(4-(2-(5H-imidazo[5,1-a]isoindol-5-yl)acetyl)piperidin-1-yl)-2-(dibenzo[b,d]furan-3-yl(methyl)amino)ethyl-1-one (150 mg, 0.29 mmol) according to the steps similar to those in Example 68.

$^1$H NMR (400 MHz, DMSO-d6) δ 8.13 (s, 1H), 7.88 (d, J=8 Hz, 1H), 7.79 (d, J=8 Hz, H), 7.66~7.59 (m, 2H), 7.52 (d, J=8 Hz, 1H), 7.41(t, J=16 Hz, 1H), 7.33~7.27 (m, 3H), 7.22 (s, 1H), 6.81 (s, 1H), 6.71 (d, J=12 Hz, 1H), 5.48~5.44 (m, 1H), 5.09~5.06 (m, 1H), 4.38~4.31 (m, 3H), 3.96~3.89 (m, 1H), 3.73~3.72 (m, 1H), 3.02~2.95 (m, 4H), 2.14~2.06 (m, 1H), 1.96~1.91 (m, 1H), 1.83~1.77 (m, 1H), 1.65~1.55 (m, 2H) 1.36~1.25 (m, 3H).

LC-MS (m/z): 521 (M+1).

In Vitro Biological Evaluation

The present detection method was used for in vitro biological activity evaluation of the compounds of the present disclosure, including in vitro enzymatic activity evaluation and enzymatic activity evaluation at the cellular level.

The purpose of the present detection was to comprehensively evaluate the enzymatic inhibitory activity of different compounds on human indoleamine 2,3-dioxygenase (IDO) in vitro and on cell models.

EXAMPLE 125

In Vitro Enzymatic Activity Assay

Principle of the Experiment

The basic principle of the in vitro IDO enzymatic activity detection is to use the IDO enzyme to metabolize the substrate L-tryptophan to produce the product kynurenine in an in vitro enzyme-catalyzed reaction system. The kynurenine is yellow in color reaction with p-dimethylaminobenzaldehyde in glacial acetic acid, and the absorbance value was measured at 492 nm on a microplate reader. The concentration of the product kynurenine in the sample is calculated by comparison to a standard curve of kynurenine with a known concentration. When different tested compounds are added, the inhibition of IDO enzyme activity is manifested by a decrease in the product kynurenine and a change in the color reaction.

Material and Reagent of the Experiment

Recombinant human IDO enzyme (IDO1 enzyme) was purchased from BPS Bioscience, USA. Detection reagents such as L-tryptophan (Sangon Biotech, A601911-0050), ascorbic acid (Sangon Biotech, SB0830-100g), catalase (Sangon Biotech, 54115066), methylene blue (Tianjin Benchmark Chemical Reagent Co., Ltd.), kynurenine (sigma, K8625-100MG), trichloroacetic acid (Sangon Biotech. A600968-0250), p-dimethylaminobenzaldehyde (Tianjin Damao Chemical Reagent Factory).

Main Process of the Experiment

The main process of the experiment is as follows:

(1) Preparation of the experiment: 2×IDO enzyme reaction buffer (working solution) was prepared according to the requirement: 0.1 M potassium phosphate buffer (pH=6.5), 400 µM L-tryptophan, 40 mM of ascorbic acid, 2000 U/ml of catalase, 40 µM methylene blue; the tested compound was diluted with 0.1 M potassium phosphate buffer (pH=6.5) into working solutions of different concentration gradients (the highest concentrations of the compounds were 10 µM). 30% (w/v) trichloroacetic acid solution. 2% p-dimethylaminobenzaldehyde in glacial acetic acid.

(2) 200 µl of enzymatic reaction system, including 100 µl of the tested compound, 100 µl of enzyme reaction buffer and 0.4 µl of recombinant human IDO enzyme solution (final concentration was 35 nM) or 1 µl of recombinant human IDO enzyme solution (final concentration was 70 nM). After mixing, the IDO enzyme reaction system was allowed to react at 37° C. for 30 minutes.

(3) Control reactions were set up at the same time the detection reaction was carried out. including 0 inhibition positive control with no tested compound added and 0 enzyme negative control with no enzyme added. All tests were run in duplicate.

(4) After the enzymatic reaction was completed, 40 µl of a pre-formulated 30% (w/v) trichloroacetic acid solution was added, and reacted at 65° C. for 20 minutes, followed by centrifugation at 12,000 rpm for 15 minutes.

(5) 100 µl of the supernatant after centrifugation was pipetted and added to a 96-well plate. An equal volume of 2% p-dimethylaminobenzaldehyde in glacial acetic acid was added, well mixed, and allowed to stand at room temperature for 10 minutes.

(6) A microplate reader (ELX800NB) was used to detect the color signal of each well with a detection wavelength of 492 nm.

(7) Formula for calculating the enzymatic inhibition rate of the test compound: enzyme activity inhibition rate (%)=(0 inhibition positive control−compound detection well)/(0 inhibition positive control−0 enzyme negative control) *100%. In addition, the enzymatic inhibition rates were calculated for the tested compounds of different concentration gradients, and then the enzymatic half maximal inhibitory concentration ($IC_{50}$) was calculated using the $IC_{50}$ calculator.

According to the above-mentioned method of experiment, the compound of the present disclosure was subjected to in vitro MO enzymatic evaluation under the same condition using the compound NLG919 (CAS: 1402836-58-1) known in the conventional art as a positive control compound (for IDO1 detection, the tested compound concentration was 200 nM). The summary of the data is shown in the table below (Table 1).

TABLE 1

Enzymatic Data of Inhibiting IDO of the Representative Compounds of the Present Disclosure

| Examples | IDO Enzymatic Inhibition Rate (%) (200 nM) | Examples | IDO Enzymatic Inhibition Rate (%) (200 nM) |
|---|---|---|---|
| 7 | 85 | 59 | 83 |
| 17 | 85 | 63 | 90 |
| 23 | 80 | 68 | 87 |
| 26 | 89 | 72 | 73 |
| 33 | 70 | 77 | 82 |
| 37 | 83 | 81 | 85 |
| 39 | 90 | 85 | 65 |
| 41 | 92 | 89 | 68 |
| 43 | 83 | 94 | 84 |
| 46 | 83 | 98 | 81 |
| 48 | 89 | 102 | 85 |
| 50 | 66 | 105 | 84 |
| 57 | 88 | 113 | 75 |
| NLG919 | 61 | | |

As can be seen from the results of the above table, the compounds of the present disclosure have a good IDO enzyme inhibitory activity, and most of them are superior to the control compound NLG919.

According to the above-mentioned method of experiment, the compound of the present disclosure was subjected to an in vitro IDO enzymatic $IC_{50}$ assay using NLG919 as a positive control compound. The summary of the data is shown in the table below (Table 2), and it can be seen that the representative compounds of the present disclosure have lower in vitro IDO $IC_{50}$ values.

TABLE 2

In vitro IDO Enzymatic $IC_{50}$ (nM) of the Representative Compounds of the Present Disclosure

| Examples | $IC_{50}$ (nM) |
|---|---|
| 7 | 55 |
| 59 | 159 |
| 85 | 144 |
| NLG919 | 198 |

EXAMPLE 126

Detection of Inhibitory Activity at the Cellular Level

In addition to constitutive expression of IDO enzymes in immune cells such as myeloid-derived suppressor cells (MDSCs), in many tumor cells, expression of IDO is also up-regulated, or is induced to express by a cytokine such as IFN-γ. In the present disclosure, IFN-γ-induced IDO enzyme expression in HeLa cells were used as a model to detect the IDO enzymatic inhibitory activity of the compound at the cellular level.

Principle of the Experiment

HeLa cells are human cervical cancer cell lines and can up-regulate the expression of endogenous IDO enzymes under the induction of human IFN-γ. The cell supernatant can be subjected to detection of the enzyme-catalyzed product kynurenine by adding the substrate L-tryptophan to the cell culture solution. The cultured HeLa cells were used and were incubated with different concentrations of tested compounds for a designated time after stimulation with human IFN-γ, and then the effect of tested compound treatment on cellular IDO enzyme activity was detected using method of color reaction of the enzyme product and p-dimethylaminohenzaldehyde.

Material and Reagent of the Experiment

Recombinant human IFN-γ cytokine purchased from Sangon Biotech, Phenol red-free DMEM for cell culture purchased from Gibco. Detection reagents such as L-tryptophan (Sangon Biotech, A601911-0050), kynurenine (sigma, K8625-100MG), trichloroacetic acid (Sangon Biotech, A600968-0250), p-dimethylaminoberizaldehyde (Tianjin DaMao Chemical Reagent Factory), 96-well flat bottom plate for cell culture (CORNING, costar 3599).

Process of the Experiment

It was carried out in a 96-well plate according to the routine cell culture experiment procedure.

(1) HeLa cells were inoculated into a 96-well culture plate at an appropriate concentration (about 20,000 cells/well), and after adhesion overnight, phenol red-free DMEM medium containing 200 μM L-tryptopha was used instead, and at the same time, cytokine human IFN-γ 50 ng/ml and tested compound at different concentration gradients (maximum final concentration was 25 μM) were added, and a solvent control (DMSO) and a negative control well without cytokine and L-tryptophan were set up in triplicate. The cells were further cultured for 48 hours and detected.

(2) 200 μl of the supernatant from the culture well was pipetted, 40 μl of a pre-formulated 30% (w/v) trichloroacetic acid solution was added, allowed to react at 65° C. for 20 minutes, and then centrifuged at 12,000 rpm for 15 minutes.

(3) 100 μl of the supernatant after centrifugation was pipetted and added into a 96-well plate, an equal volume of 2% p-dimethylaminobenzaldehyde in glacial acetic acid was added, and they were mixed well and allowed to stand at room temperature for 10 minutes.

(4) A microplate reader (ELX800NB) was used to detect the color signal of each well, and the detection wavelength was 492 nm.

(5) Formula for calculating the enzymatic inhibition rate of the test compound at the cellular level: enzyme activity inhibition rate (%)=(0 inhibition positive control–compound detection well)/(0 inhibition positive control–negative control)*100%. In addition, the cellular enzymatic inhibition rates were calculated for the tested compounds of different concentration gradients, and then the enzymatic half maximal effective concentration ($EC_{50}$) was calculated. using the $EC_{50}$ calculator.

According to the above-mentioned method of experiment, the compound of the present disclosure was subjected to an IDO enzymatic evaluation at the cellular level (the concentration of the tested compound was 1 μM) using NLG919 as a positive control compound. The summary of the data is shown in the table below (Table 3). As can be seen from Table 3, the compounds of the present disclosure have a good IDO inhibitory activity, and most of them are superior to the control compound NLG919.

TABLE 3

Human IDO Inhibitory Rate Data at the Cellular Level of the Representative Compounds of the Present Disclosure

| Examples | IDO Inhibitory Rate (%) (1 μM) | Examples | IDO Inhibitory Rate (%) (1 μM) |
|---|---|---|---|
| 7 | 93 | 68 | 98 |
| 17 | 93 | 72 | 91 |
| 23 | 77 | 77 | 95 |
| 26 | 92 | 81 | 94 |
| 37 | 97 | 85 | 84 |
| 39 | 98 | 89 | 85 |
| 41 | 99 | 94 | 98 |
| 43 | 89 | 98 | 83 |
| 46 | 93 | 102 | 95 |
| 48 | 99 | 105 | 91 |
| 50 | 69 | 109 | 68 |
| 57 | 91 | 113 | 74 |
| 59 | 92 | 124 | 79 |
| 63 | 99 | | |
| NLG919 | 79 | | |

According to the above-mentioned method of experiment, the compound of the present disclosure was subjected to an IDO enzymatic $EC_{50}$ assay at the cellular level using NLG919 as a positive control compound. The summary of the data is shown in the table below (Table 4).

TABLE 4

IDO $EC_{50}$ (nM) of the Representative Compound at the Cellular Level of the Present Disclosure

| Examples | $IC_{50}$ (nM) |
|---|---|
| 7 | 154 |
| 59 | 169 |
| 85 | 312 |
| NLG919 | 430 |

As can be seen from the above-mentioned results, the representative compounds of the present disclosure have lower IDO $EC_{50}$ values at the cellular level, which are superior to the control compound NLG919.

The invention claimed is:

1. A compound of General Formula I,

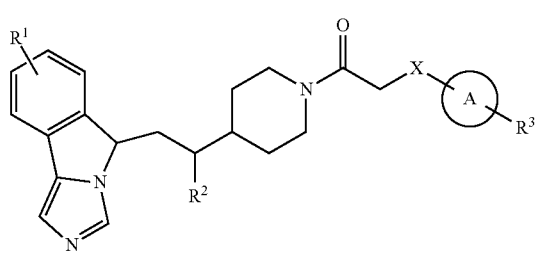

or a pharmaceutically acceptable salt thereof,
wherein
$R^1$ is one or more substituents selected from the group consisting of hydrogen, hydroxyl, cyano, nitro, halogen, $C_{1-6}$ alkyl, $C_{1-6}$ alkoxy, $C_{1-6}$ haloalkyl, $C_{1-6}$ alkylcarbonyl and $C_{1-6}$ alkylamino;
$R^2$ is hydroxyl or amino;

R³ is one or more substituents selected from the group consisting of hydrogen, hydroxyl, cyano, halogen, $C_{1-6}$ alkyl, $C_{1-6}$ alkoxy, $C_{1-6}$ haloalkyl, $C_{1-6}$ alkylcarbonyl and $C_{1-6}$ alkylamino;

X is $NR^4$ or O;

wherein $R^4$ is hydrogen or $C_{1-6}$ alkyl;

ring A is an optionally substituted group selected from the group consisting of: phenyl; 3- to 7-membered saturated or partially unsaturated carbocyclic ring; 8 to 10 membered saturated, partially unsaturated or aromatic bicyclic or tricyclic ring; 5- to 6-membered monocyclic heteroaryl ring having 1 to 4 heteroatoms independently selected from nitrogen, oxygen or sulfur; 4- to 7-membered saturated or partially unsaturated heterocyclic ring having 1 to 3 heteroatoms independently selected from nitrogen, oxygen or sulfur; 7- to 10-membered saturated or partially unsaturated heterocyclic bicyclic or tricyclic ring having 1 to 5 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

2. The compound of General Formula I according to claim 1, wherein $R^1$ is one or more substituents selected from the group consisting of hydrogen, hydroxyl, cyano, nitro, halogen, and $C_{1-6}$ haloalkyl;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen, methyl or ethyl;

ring A is a group selected from the group consisting of: phenyl; 3- to 6-membered saturated carbocyclic ring; 8- to 10-membered aromatic bicyclic or tricyclic ring; 5- to 6-membered monocyclic heteroaryl ring having 1 to 4 heteroatoms independently selected from nitrogen, oxygen or sulfur; 7- to 10-membered saturated or partially unsaturated heterocyclic bicyclic or tricyclic ring having 1 to 5 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

3. The compound of General Formula I according to claim 1, wherein $R^1$ is one or more substituents selected from the group consisting of hydrogen, hydroxyl, cyano, nitro and halogen;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 3- to 6-membered saturated carbocyclic ring; 8- to 10-membered aromatic bicyclic or tricyclic ring; 5- to 6-membered monocyclic heteroaryl ring having 1 to 4 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

4. The compound of General Formula I according to claim 1, wherein $R^1$ is one or more substituents selected from the group consisting of hydrogen, hydroxyl, cyano and nitro;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 8- to 10-membered aromatic bicyclic or tricyclic ring; 5- to 6-membered monocyclic heteroaryl ring having 1 to 4 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

5. The compound of General Formula I according to claim 1, wherein $R^1$ is one or more substituents selected from hydrogen, hydroxyl and cyano;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 5- to 6-membered monocyclic heteroaryl ring having 1 to 4 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

6. The compound of General Formula I according to claim 1, wherein $R^1$ is hydrogen;

$R^2$ is hydroxyl;

$R^3$ is one or more substituents selected from the group consisting of hydrogen, hydroxyl, cyano, nitro, halogen, $C_{1-6}$ alkyl, $C_{1-6}$ alkoxy, and $C_{1-6}$ haloalkyl;

X is $NR^4$;

wherein $R^4$ is hydrogen or methyl;

ring A is a group selected from the group consisting of: phenyl; 5- to 6-membered monocyclic heteroaryl ring having 1 to 4 heteroatoms independently selected from nitrogen, oxygen or sulfur; and 8- to 10-membered heteroaryl bicyclic or tricyclic ring having 1 to 5 heteroatoms independently selected from nitrogen, oxygen or sulfur.

7. The compound of General Formula I according to claim 1, wherein the compound is selected from the group consisting of:

1-(4-(1-hydroxy-2-(5H-imidazo[5,1-a]isoindol-5-yl)ethyl)piperidin-1-yl)-2-phenoxyethyl-1-one;

1-(4-(1-hydroxy-2-(5H-imidazo[5,1-a]isoindol-5-yl)ethyl)piperidin-1-yl)-2-((tetrahydrofuran-3-yl)oxy)ethyl-1-one;

2-((9H-carbazol-3-yl)oxy)-1-(4-(1-hydroxy-2-(5H-imidazo[5,1-a]isoindol-5-yl)ethyl)piperidin-1 -yl)ethyl-1-one;

1-(4-(1-hydroxy-2-(5H-imidazo[5,1-a]isoindol-5-yl)ethyl)piperidin-1-yl)-2-(pyridazine-4-yloxy)ethyl-1-one;

1-(4-(1-hydroxy-2-(5H-imidazo[5,1-a]isoindol-5-yl)ethyl)piperidin-1-yl)-2-(quinolin-6-yloxy)ethyl-1-one;

1-(4-(1-hydroxy-2-(5H-imidazo[5,1-a]isoindol-5-yl)ethyl)piperidin-1-yl)-2-(quinolin-6-yloxy)ethyl-1-one;
1-(4-(1-hydroxy-2-(5H-imidazo[5,1-a]isoindol-5-yl)ethyl)piperidin-1-yl)-2-(pyrrolidine-3-yloxy)ethyl-1-one;
2-((7H-purin-6-yl)oxy)-1-(4-(1-hydroxy-2-(5H-imidazo[5,1-a]isoindol-5-yl)ethyl)piperidin-1-yl)ethyl-1-one;
2-(benzo[d]oxazolin-2-yloxy)-1-(4-(1-hydroxy-2-(5H-imidazo[5,1-a]isoindol-5-yl)ethyl)piperidin-1-yl)ethyl-1-one;
2-(3-chloro-4-fluorophenoxy)-1-(4-(1-hydroxy-2-(5H-imidazo[5,1-a]isoindol1-5-yl)ethyl)piperidin-1-yl)ethyl-1-one;
2-(3-chlorophenoxy)-1-(4-(1-hydroxy-2-(5H-imidazo[5,1-a]isoindol-5-yl)ethyl)piperidin-1-yl)ethyl-1-one;
2-(4-fluorophenoxy)-1-(4-(1-hydroxy-2-(5H-imidazo[5,1-a]isoindol-5-yl)ethyl)piperidin-1-yl)ethyl-1-one;
2-(3,4-dimethylphenoxy)-1-(4-(1-hydroxy-2-(5H-imidazo[5,1-a]isoindol-5-yl)ethyl)piperidin-1-yl)ethyl-1-one;
2-(3-trifluoromethylphenoxy)-1-(4-(1-hydroxy-2-(5H-imidazo[5,1-a]isoindol-5-yl)ethyl)piperidin-1-yl)ethyl-1-one;
2-(cyclohexyloxy)-1-(4-(1-hydroxy-2-(5H-imidazo[5,1-a]isoindol-5-yl)ethyl)piperidin-1-yl)ethyl-1-one;
2-(dibenzo[b,d]furan-2-yloxy)-1-(4-(1-hydroxy-2-(5H-imidazo[5,1-a]isoindol-5-yl)ethyl)piperidin-1-yl)ethyl-1-one;
1-(4-(1-hydroxy-2-(5H-imidazo[5,1-a]isoindol-5-yl)ethyl)piperidin-1-yl)-2-(methyl(phenyl)amino)ethyl-1-one;
2-((3 -chlorophenyl)(methyl)amino)-1-(4-(2-(5H-imidazo[5,1-a]isoindol-5-yl)ethyl)piperidin-1-yl)-ethyl-1-one;
2-((3 -chloro-4-fluorophenyl)(methyl)amino)-1-(4(1-hydroxy-2-(5H-imidazo[5,1-a]isoindol-5-yl)ethyl)piperidin-1-yl)ethyl-1-one;
2-((4-fluorophenyl)(methyl)amino)-1-(4-(1-hydroxy-2-(5H-imidazo[5,1-a]isoindol-5-yl)ethyl)piperidin-1-yl)ethyl-1-one;
2-((3,4-dimethylphenyl)(methyl)amino)-1-(4-(1-hydroxy-2-(5H-imidazo[5,1-a]isoindol-5-yl)ethyl)piperidin-1-yl)ethyl-1-one;
2-(ethyl(phenyl)amino)-1-(4-(1-hydroxy-2-(5H-imidazo[5,1-a]isoindol-5-yl)ethyl)piperidin-1-yl)ethyl-1-one;
1-(4-(1-hydroxy-2-(5H-imidazo[5,1-a]isoindol-5-yl)ethyl)piperidin-1-yl)-2-(phenylamino)ethyl-1-one;
1-(4-(1-hydroxy-2-(5H-imidazo[5,1-a]isoindol-5-yl)ethyl)piperidin-1-yl)-2-(methyl(4-trifluoromethylphenyl)amino)ethyl-1-one;
1-(4-(1-hydroxy-2-(5H-imidazo[5,1-a]isoindol-5-yl)ethyl)piperidin-1-yl)-2-(methyl(3-trifluoromethylphenyl)amino)ethyl-1-one;
2-((4-cyanophenyl)(methyl)amino)-1-4-(1-hydroxy-2-(5H-imidazo[5,1-a]isoindol-5-yl)ethyl)piperidin-1-yl)ethyl-1-one;
2-((3 -methoxyphenyl)(methyl)amino)-1-(4-(1-hydroxy-2-(5H-imidazo[5,1-a]isoindol-5-yl)ethyl)piperidin-1-yl)ethyl-1-one;
1-(4-(1-hydroxy-2-(5H-imidazo[5,1-a]isoindol-5-yl)ethyl)piperidin-1-yl)-2-(methyl(4-nitrophenyl)amino)ethyl-1-one;
1-(4-(1-hydroxy-2-(5H-imidazo[5,1-a]isoindol-5-yl)ethyl)piperidin-1-yl)-2-(methyl(pyridin-2-yl)amino)ethyl-1-one;
1-(4-(1-hydroxy-2-(5H-imidazo[5,1-a]isoindol-5-yp-ethyl)piperidin-1-yl)-2-(methyl(quinolin-6-yl)amino)ethyl-1-one;
1-(4-(1-hydroxy-2-(5H-imidazo[5,1-a]isoindol-5-yl)ethyl)piperidin-1-yl)-2-(methyl(7H-purin-6-yl)amino)ethyl-1-one; and
2-(dibenzo[b,d]furan-3-yl(methyl)amino)-1-(4-(1-hydroxy-2-(5H-imidazo[5,1-a]isoindol-5-yl)ethyl)piperidin-1-yl)ethyl-1-one.

8. A method of preparing the compound of General Formula I according to claim 1,

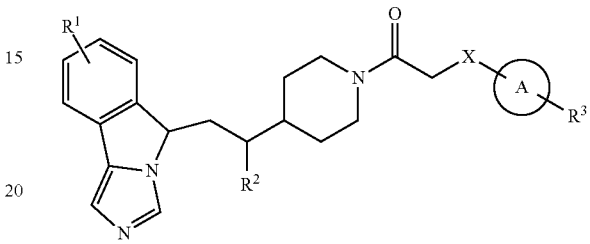

including reacting a compound of Formula C

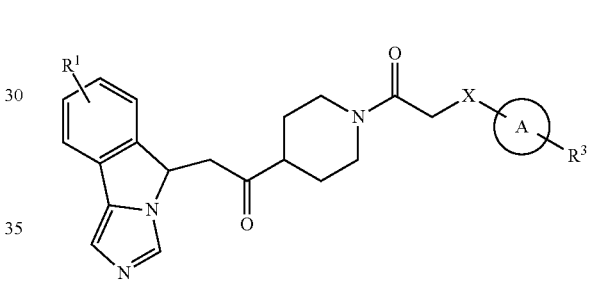

under an action of an organic solvent and a reducing agent to form the compound of General Formula I, wherein
$R^1$, $R^2$, $R^3$, X and A are as defined according to claim 1.

9. The method according to claim 8, wherein the reducing agent is selected from the group consisting of $NaBH_4$, $KBH_4$, $NaBH(OAc)_3$, $KBH(OAc)_3$ and $NaBH_3CN$.

10. The method according to claim 8, wherein the organic solvent is selected from methanol, ethanol, tetrahydrofuran.

11. A compound of Formula C:

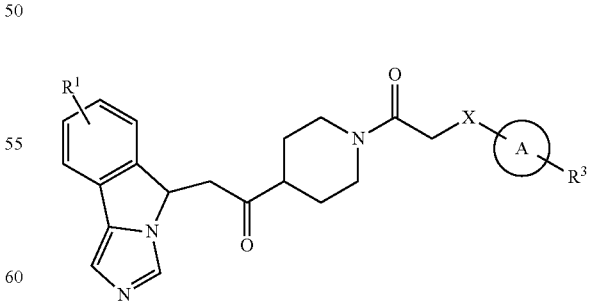

wherein $R^1$, $R^3$, X and A are as defined according to claim 1.

12. A method of preparing the compound of Formula C according to claim 11, including coupling a compound of Formula A

A

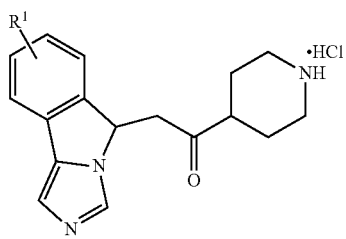

with a compound of Formula B

B

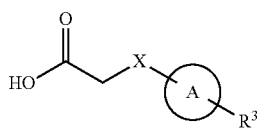

under an action of an organic solvent and a coupling reagent to form a compound of Formula C, wherein $R^1$, $R^3$, X and A are as defined according to claim 1.

13. The method according to claim 12, wherein the coupling reagent is selected from the group consisting of 1-ethyl-3-(3-dimethylaminopropyl)carbodiimide (EDC), N,N'-dicyclohexylcarbodiimide (DCC), N,N'-carbonyldiimidazole (CDI), and O-(7-azabenzotriazole)-N,N,N',N'-tetramethylurea hexafluorophosphate (HATU).

14. The method according to claim 12, wherein the organic solvent is selected from the group consisting of benzene, toluene, tetrahydrofuran, dioxane, dichloromethane, chloroform, and N,N'-dimethylformamide.

15. The method according to claim 8, wherein the method includes using the compound of Formula C according to claim 11 as an intermediate.

16. A pharmaceutical composition comprising the compound according to claim 1 and an optional pharmaceutical excipient.

17. A method for inhibiting indoleamine 2,3-dioxygenase (IDO), comprising using the compound according to claim 1.

18. A method for treating cancer, eye disease, autoimmune disease, psychological disorder, depression and anxiety, comprising using the compound according to claim 1.

19. A fluorescent label, spin label, heavy-metal label or isotope label of the compound according to claim 1.

* * * * *